(12) United States Patent
Ahn

(10) Patent No.: US 8,618,324 B2
(45) Date of Patent: *Dec. 31, 2013

(54) COMPOSITION AND METHOD FOR MAKING OLIGO-BENZAMIDE COMPOUNDS

(75) Inventor: Jung-Mo Ahn, Richardson, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 256 days.

This patent is subject to a terminal disclaimer.

(21) Appl. No.: 12/048,197

(22) Filed: Mar. 13, 2008

(65) Prior Publication Data

US 2009/0012141 A1 Jan. 8, 2009

Related U.S. Application Data

(60) Provisional application No. 60/894,580, filed on Mar. 13, 2007.

(51) Int. Cl.
*C07K 5/02* (2006.01)

(52) U.S. Cl.
USPC .............................. 562/453; 562/553; 560/46

(58) Field of Classification Search
USPC .................................... 562/453, 553; 560/46
See application file for complete search history.

(56) References Cited

U.S. PATENT DOCUMENTS

| 5,212,203 A | 5/1993 | Shroot et al. |
| 5,929,114 A | 7/1999 | Domagala et al. |
| 2005/0261346 A1 | 11/2005 | Zhu et al. |

OTHER PUBLICATIONS

International Search Report and Written Opinion for PCT/US2008/056920 dated Aug. 1, 2008.
International Search Report and Written Opinion for PCT/US2008/056918 dated Sep. 10, 2008.
Ahn, et al., "Facile synthesis of benzamides to mimic an alpha helix," Tetrahedron Letters (2007), 48:3543-3547.
Konig, et al., "Solid-Phase Synthesis of Oligo(p-benzamide) Foldamers," Organnic Letters (2006), 8:1819-1822.
Konig, et al., "Supramolecular PEG-co-Oligo(p-benzamide)s Prepared on a Peptide Synthezier," J Am Chem Soc (2007), published on Web Dec. 23, 2006, 129:704-708.
Tanatani, et al., "Helical Structures of N-Alkylated Poly(p-benzamide)s," J Am Chem Soc (2005), 127:8553-8561.
Ahn, J.-M., et al., "A new approach to search for the bioactive conformation of glucagon: positional cyclization scanning." J. Med. Chem. (2001), 44:3109-3116.
Ahn, J.-M., et al., "Development of potent truncated glucagon antagonists." J. Med. Chem. (2001), 44:1372-1379.
Ahn, J.-M., et al., "Peptidomimetics and peptide backbone modifications." Mini-Reviews in Medicinal Chemistry (2002), 2:463-473.
Bulotta, et al., "ACultured pancreatic ductal cells undergo cell cycle re-distribution and beta-cell-like differentiation in response to glucagon-like peptide-1." J. Mol. Endocrinol. (2002), 29:347-360.

Burgess, K., et al., "Solid-phase syntheses of β-turn analogues to mimic or disrupt protein-protein interactions". Acc. Chem. Res. (2001), 34:826-835.
Cavaghan, M. K., et al., "Interactions between insulin resistance and insulin secretion in the development of glucose intolerance." J. Clin. Invest. (2000), 106:329-333.
Chang, L. L., et al., "Substituted imidazoles as glucagon receptor antagonists." Bioorg. Med. Chem. Lett. (2001), 11:2549-2553.
Chapuis, H. P., et al., "Shorter puromycin analog synthesis by means of an efficient Staudinger-Vilarrasa coupling." Tetrahedron (2006), 62:12108-12115.
Chen, D., et al., "A nonpeptidic agonist of glucagon-like peptide 1 receptors with efficacy in diabetic db/db mice." Proc. Natl. Acad. Sci. U.S.A. (2007), 104:943-948.
Defronzo, R. A., et al., "Effects of exenatide (exendin-4) on glycemic control and weight over 30 weeks in metformin-treated patients with type 2 diabetes." Diabetes Care (2005), 28:1092-1100.
Drucker, D. J., et al., "The incretin system: glucagon-like peptide-1 receptor agonists and dipeptidyl peptidase-4 inhibitors in type 2 diabetes." Lancet (2006), 368:1696-1705.
Edwards, C. M. B., et al., "Exendin-4 reduces fasting and postprandial glucose and decreases energy intake in healthy volunteers." Am. J. Physiol. Endocrinol. Metab. (2001), 281:E155-E161.
Egan, J. M., et al., "GLP-1 receptor agonists are growth and differentiation factors for pancreatic islet beta cells." Diabetes/Metab. Res. Rev. (2003), 19:115-123.
Elbronds, B., et al., "Pharmacokinetics, pharmacodynamics, safety, and tolerability of a single-dose of NN2211, a long-acting glucagon-like peptide 1 derivative, in healthy male subjects." Diabetes Care (2002), 25:1398-1404.
Ernst, J. T., et al., "Design and application of an α-helixmimetic scaffold based on an oligoamide-foldamer strategy: antagonism of the Bak BH3/Bcl-xl complex." Agnew. Chem. Int. Ed. (2003), 42:535-539.
Hoare, S. R. J., et al., "Mechanisms of peptide and nonpeptide ligand binding to class B G-proteincoupled receptors." Drug Discovery Today (2005), 10:417-427.
Hruby, V. J., et al., "Design in topographical space of peptide and peptidomimetic ligands that affect behavior a chemist's glimpse at the mind-body problem." Acc. Chem. Res. (2001), 34:389-397.
Jacoby, E., et al., "Biphenyls as potential mimetics of protein α-helix." Bioorg. Med. Chem. Lett. (2002), 12:891-893.
Knudsen, L. B., et al., "Glucagon-like peptide-1: the basis of a new class of treatment for type 2 diabetes." J. Med. Chem. (2004), 47:4128-4134.
Knudsen, L. B., et al., "Small-molecule agonists for the glucagon-like peptide 1 receptor." Proc. Natl. Acad. Sci. U.S.A. (2007), 104:937-942.
Kolterman, O. G., et al., "Synthetic exendin-4 (exenatide) significantly reduces postprandial and fasting plasma glucose in subjects with type 2 diabetes." J. Clin. Endocrinol. Metab. (2003), 88:3082-3089.

(Continued)

*Primary Examiner* — David Lukton
(74) *Attorney, Agent, or Firm* — Parker Highlander PLLC

(57) ABSTRACT

The present invention includes compound compositions and methods of making compounds that include an oligo-benzamide compound having at least two optionally substituted benzamides.

10 Claims, 78 Drawing Sheets

(56) References Cited

OTHER PUBLICATIONS

Ling, A., et al., "Identification of alkylidene hydrazides as glucagon receptor antagonists." J. Med. Chem. (2001), 44:3141-3149.

Madsen, P., et al., "Optimization of alkylidene hydrazide based human glucagon receptor antagonists. Discovery of the highly potent and orally available 3-cyano-4-hydroxybenzoic acid [1-(2,3,5,6-tetramethylbenzyl)-1H-indol-4-ylmethylene]hydrazide." J. Med. Chem. (2002), 45:5755-5775.

Mahato, R. I., et al., "Emerging trends in oral delivery of peptide and protein drugs." Critical Reviews in Therapeutic Drug Carrier Systems (2003), 20:153-214.

Murphy, K. G.; "Nonpeptidic glucagon-like peptide 1 receptor agonists: A magic bullet for diabetes?" Proc. Natl. Acad. Sci. U.S.A. (2007), 104:689-690.

Neidigh, J. W., et al., "Exendin-4 and glucagon-likepeptide-1: NMR structural comparisons in the solution and micelle-associated states." Biochemistry (2001), 40:13188-13200.

Oguri, H., et al., "Design and synthesis of a trans-fused polycyclic ether skeleton as an a-helix mimetic scaffold." Tetrahedron Lett. (2005), 46:2179-2183.

Orner, B. P., et al., "Toward proteomimetics: Terphenyl derivatives as structural and functional mimics of extended regions of an α-helix." J. Am. Chem. Soc. (2001), 123:5382-5383.

Peczuh, M. W., et al., "Peptide and protein recognition by designed molecules." Chem. Rev. (2000), 100:2479-2494.

Perry, T. A.,et al., "The glucagon-like peptides: a double-edged therapeutic sword?" Trends Pharmacol. Sci. (2003), 24:377-383.

Rickard, D. J., et al., "Intermittent treatment with parathyroid hormone (PTH) as well as a non-peptide small molecule agonist of the PTH1 receptor inhibits adipocyte differentiation in human bone marrow stromal cells." Bone (2006), 39:1361-1372.

Runge, S., et al., "Different domains of the glucagon and glucagon-like peptide-1 receptors provide the critical determinants of ligand selectivity." Br. J. Pharmacol. (2003), 138:787-794.

Souers, A. J., et al., "β-Turn mimetic library synthesis: scaffolds and applications." Tetrahedron (2001), 57:7431-7448.

Stoffers, D. A., et al., "Insulinotropic glucagon-like peptide 1 agonists stimulate expression of homeodomain protein IDX-1 and increase islet size in mouse pancreas." Diabetes (2000), 49:741-748.

Tibaduiza, E. C., et al., "A small molecule ligand of the glucagon-like peptide 1 receptor targets its amino-terminal hormone binding domain." J. Biol. Chem. (2001), 276:37787-37793.

Toft-Nielsen, M. B., et al., "Determinants of the effectiveness of glucagon-like peptide-1 in type 2 diabetes." J. Clin. Endocrinol. Metab. (2001), 86:3853-3860.

Vilsboll, T., et al., "No reactive hypoglycaemia in type 2 diabetic patients after subcutaneous administration of GLP-1 and intravenous glucose." Diabetic Med. (2001), 18:144-149.

Zander, M., et al., "Effect of 6-week course of glucagon-like peptide 1 on glycaemic control, insulin sensitivity, and beta-cell fuction in type 2 diabetes: a parallel-group study." Lancet (2002), 359:824-830.

Zhang, B. B., et al., "New approaches in the treatment of type 2 diabetes." Curr. Opin. Chem. Biol. (2000), 4:461-467.

Database CAPLUS on STN, Acc. No. 1998:159344, Gambacorti-Passerini et al., "Inhibition of the ABL kinase activity blocks the proliferation of BCR/ABL+ leukemic cells and induces apoptosis," *Blood Cells, Molecules & Diseases*, 23(3):380-394, 1997 (abstract only).

Office Action issued in U.S. Appl. No. 13/559,388, mailed May 2, 2013.

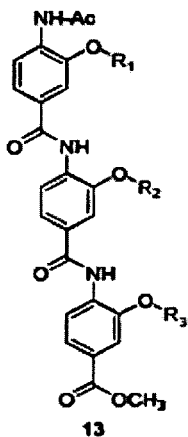
FIGURE 3A
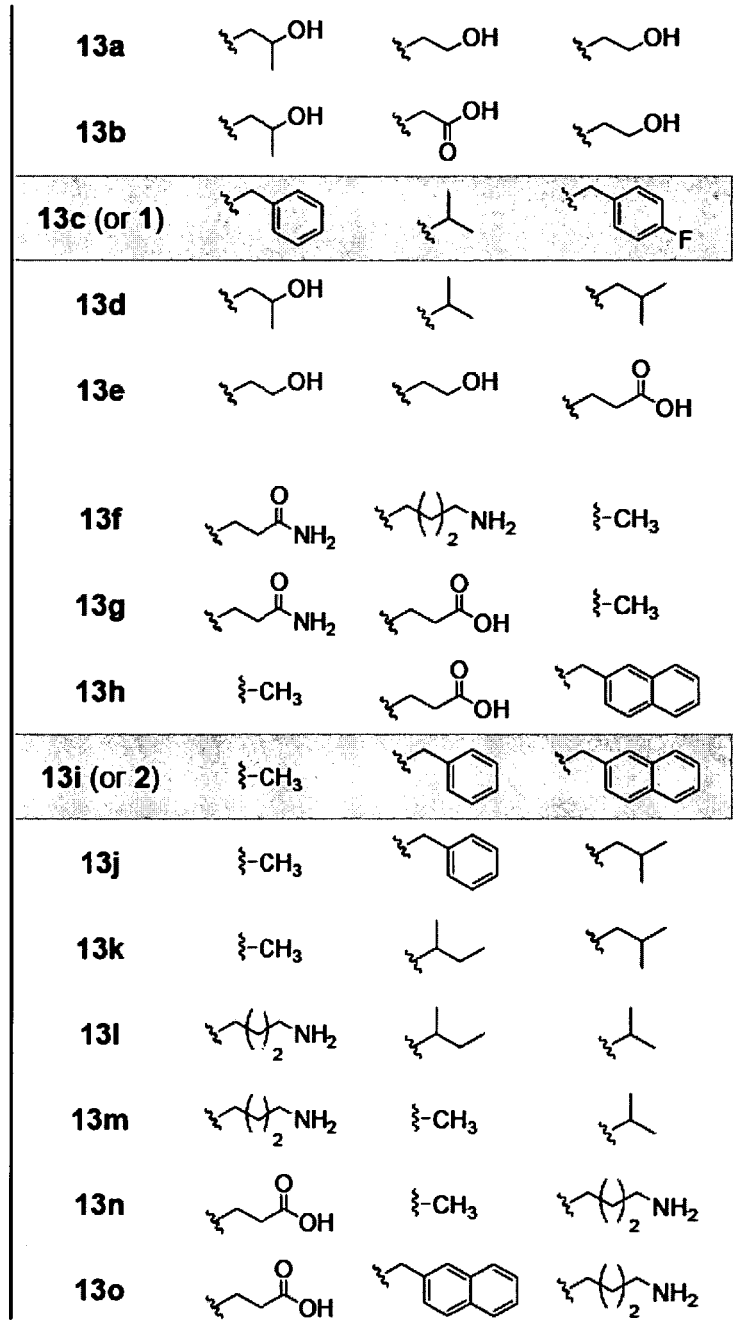
FIGURE 3B
FIGURE 3

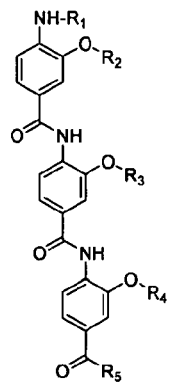

Structure:

FIG. 13A

| Compound No. | R1 | R2 | R3 | R4 | R5 |
|---|---|---|---|---|---|
| 101 | Ac | benzyl | isopropyl | 4-F-benzyl | OMe |
| 102 | Ac | phenethyl | isopropyl | 4-F-benzyl | OMe |
| 103 | Ac | pentafluorobenzyl | isopropyl | 4-F-benzyl | OMe |
| 104 | Ac | 4-F-benzyl | isopropyl | 4-F-benzyl | OMe |
| 105 | Ac | 4-OH-phenethyl | isopropyl | 4-F-benzyl | OMe |
| 106 | Ac | 2-naphthylmethyl | isopropyl | 4-F-benzyl | OMe |
| 107 | Ac | 1-naphthylethyl | isopropyl | 4-F-benzyl | OMe |
| 108 | Ac | thiophen-3-ylethyl | isopropyl | 4-F-benzyl | OMe |
| 109 | Ac | imidazol-4-ylethyl | isopropyl | 4-F-benzyl | OMe |
| 110 | Ac | benzyl | -CH₃ | 4-F-benzyl | OMe |
| 111 | Ac | benzyl | sec-butyl | 4-F-benzyl | OMe |

FIG. 13A (cont.)

| | | | | | |
|---|---|---|---|---|---|
| 112 | Ac | benzyl | n-butyl | 4-F-benzyl | OMe |
| 113 | Ac | benzyl | isobutyl | 4-F-benzyl | OMe |
| 114 | Ac | benzyl | cyclohexylmethyl | 4-F-benzyl | OMe |
| 115 | Ac | benzyl | cyclopropyl | 4-F-benzyl | OMe |
| 116 | Ac | benzyl | 4-F-benzyl | 4-F-benzyl | OMe |
| 117 | Ac | benzyl | benzyl | benzyl | OMe |
| 118 | Ac | benzyl | isopropyl | benzyl | OMe |
| 119 | Ac | benzyl | isopropyl | pentafluorobenzyl | OMe |
| 120 | Ac | benzyl | isopropyl | 4-OH-phenethyl | OMe |
| 121 | Ac | benzyl | isopropyl | 2-naphthylmethyl | OMe |
| 122 | Ac | benzyl | isopropyl | 1-naphthylmethyl | OMe |
| 123 | Ac | benzyl | isopropyl | thiophenyl-methyl | OMe |
| 124 | Ac | benzyl | isopropyl | imidazolyl-ethyl | OMe |
| 125 | Ac | imidazolyl-ethyl | imidazolyl-ethyl | imidazolyl-ethyl | OMe |
| 126 | Ac | imidazolyl-ethyl | isopropyl | 4-OH-phenethyl | OMe |
| 127 | Ac | imidazolyl-ethyl | isobutyl | 4-OH-phenethyl | OMe |
| 128 | Ac | benzyl | phenethyl | phenethyl | OMe |
| 129 | Ac | benzyl | pentafluorobenzyl | pentafluorobenzyl | OMe |
| 130 | Ac | -CH$_3$ | -CH$_3$ | -CH$_3$ | OMe |

FIG. 13A (cont.)

| # | | | | | |
|---|---|---|---|---|---|
| 131 | Ac | isobutyl | isobutyl | isobutyl | OMe |
| 132 | Ac | isopropyl-CH | isopropyl-CH | isopropyl-CH | OMe |
| 133 | Ac | n-butyl | n-butyl | n-butyl | OMe |
| 134 | Ac | CH₂CH₂OH | CH₂CH₂OH | CH₂CH₂OH | OMe |
| 135 | Ac | CH₂CH₂OH | CH₂CH₂OH | CH₂CH₂COOH | OMe |
| 136 | Ac | CH₂CH₂COOH | (CH₂)₂NH₂ | CH₂CH₂COOH | OMe |
| 137 | Ac | (CH₂)₂NH₂ | CH₂CH₂COOH | (CH₂)₂NH₂ | OMe |
| 138 | Ac | CH(CH₃)OH | CH₂CH₂COOH | (CH₂)₂NH₂ | OMe |
| 139 | Ac | CH₂CH₂OH | CH₂CH₂COOH | (CH₂)₃NHC(NH)NH₂ | OMe |
| 140 | Ac | CH₂CH₂COOH | (CH₂)₃NHC(NH)NH₂ | CH₂CH₂COOH | OMe |
| 141 | Ac | (CH₂)₃NHC(NH)NH₂ | (CH₂)₃NHC(NH)NH₂ | (CH₂)₃NHC(NH)NH₂ | OMe |
| 142 | Ac | CH₂-imidazole | CH₂CH₂-Ph | CH₂CH₂COOH | OMe |
| 143 | Ac | CH₂-Ph | CH₂CH₂COOH | CH₂-(4-F-Ph) | OMe |
| 144 | Ac | CH₂-Ph | CH₂CH₂COOH | CH₂CH₂-(4-OH-Ph) | OMe |
| 145 | Ac | -CH₃ | CH₂-Ph | CH₂-naphthyl | OMe |
| 146 | Ac | -CH₃ | CH₂CH₂-Ph | CH₂-naphthyl | OMe |
| 147 | Ac | -CH₃ | CH₂-(4-F-Ph) | CH₂-naphthyl | OMe |
| 148 | Ac | -CH₃ | CH₂-2-naphthyl | CH₂-2-naphthyl | OMe |
| 149 | Ac | -CH₃ | CH₂-1-naphthyl | CH₂-2-naphthyl | OMe |
| 150 | Ac | -CH₃ | CH₂-C₆F₅ | CH₂-2-naphthyl | OMe |

| 152 | Ac | §-CH₃ |  |  | OMe |
| 153 | Ac | §-CH₃ |  |  | OMe |
| 154 | Ac | §-CH₃ |  |  | OMe |
| 155 | Ac | §-CH₃ |  |  | OMe |
| 156 | Ac | §-CH₃ |  |  | OMe |
| 157 | Ac | §-CH₃ |  |  | OMe |
| 158 | Ac | §-CH₃ |  |  | OMe |
| 159 | Ac |  |  |  | OMe |
| 160 | Ac |  |  |  | OMe |

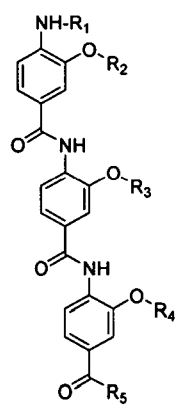

Structure:

FIG. 13B

| Compound No. | R1 | R2 | R3 | R4 | R5 |
|---|---|---|---|---|---|
| 161 | His-Gly | benzyl | isopropyl | 4-fluorobenzyl | OMe |
| 162 | His-Gly | phenethyl | isopropyl | 4-fluorobenzyl | OMe |
| 163 | His-Gly | pentafluorobenzyl | isopropyl | 4-fluorobenzyl | OMe |
| 164 | His-Gly | 4-fluorobenzyl | isopropyl | 4-fluorobenzyl | OMe |
| 165 | His-Gly | 4-hydroxyphenethyl | isopropyl | 4-fluorobenzyl | OMe |
| 166 | His-Gly | 2-naphthylmethyl | isopropyl | 4-fluorobenzyl | OMe |
| 167 | His-Gly | 1-naphthylmethyl | isopropyl | 4-fluorobenzyl | OMe |
| 168 | His-Gly | 3-thienylethyl | isopropyl | 4-fluorobenzyl | OMe |
| 169 | His-Gly | imidazolylethyl | isopropyl | 4-fluorobenzyl | OMe |
| 170 | His-Gly | benzyl | -CH₃ | 4-fluorobenzyl | OMe |
| 171 | His-Gly | benzyl | sec-butyl | 4-fluorobenzyl | OMe |
| 172 | His-Gly | benzyl | n-butyl | 4-fluorobenzyl | OMe |

| 173 | His-Gly |  |  |  | OMe |
| 174 | His-Gly |  |  |  | OMe |
| 175 | His-Gly |  |  |  | OMe |
| 176 | His-Gly |  |  |  | OMe |
| 177 | His-Gly |  |  |  | OMe |
| 178 | His-Gly |  |  |  | OMe |
| 179 | His-Gly |  |  |  | OMe |
| 180 | His-Gly |  |  |  | OMe |
| 181 | His-Gly |  |  |  | OMe |
| 182 | His-Gly |  |  |  | OMe |
| 183 | His-Gly |  |  |  | OMe |
| 184 | His-Gly |  |  |  | OMe |
| 185 | His-Gly |  |  |  | OMe |
| 186 | His-Gly |  |  |  | OMe |
| 187 | His-Gly |  |  |  | OMe |
| 188 | His-Gly |  |  |  | OMe |
| 189 | His-Gly |  |  |  | OMe |

FIG. 13B (cont.)

| # | | R1 | R2 | R3 | R4 |
|---|---|---|---|---|---|
| 190 | His-Gly | -CH₃ | -CH₃ | -CH₃ | OMe |
| 191 | His-Gly | isobutyl | isobutyl | isobutyl | OMe |
| 192 | His-Gly | isopropyl | isopropyl | isopropyl | OMe |
| 193 | His-Gly | n-butyl | n-butyl | n-butyl | OMe |
| 194 | His-Gly | -CH₂CH₂OH | -CH₂CH₂OH | -CH₂CH₂OH | OMe |
| 195 | His-Gly | -CH₂CH₂OH | -CH₂CH₂OH | -(CH₂)₃COOH | OMe |
| 196 | His-Gly | -(CH₂)₃COOH | -(CH₂)₄NH₂ | -(CH₂)₃COOH | OMe |
| 197 | His-Gly | -(CH₂)₄NH₂ | -(CH₂)₃COOH | -(CH₂)₄NH₂ | OMe |
| 198 | His-Gly | -CH(OH)CH₃ | -(CH₂)₃COOH | -(CH₂)₄NH₂ | OMe |
| 199 | His-Gly | -CH₂CH₂OH | -(CH₂)₃COOH | -(CH₂)₃NHC(NH)NH₂ | OMe |
| 200 | His-Gly | -(CH₂)₃COOH | -(CH₂)₃NHC(NH)NH₂ | -(CH₂)₃COOH | OMe |
| 201 | His-Gly | -(CH₂)₃NHC(NH)NH₂ | -(CH₂)₃NHC(NH)NH₂ | -(CH₂)₃NHC(NH)NH₂ | OMe |
| 202 | His-Gly | -CH₂-imidazole | -CH₂-phenyl | -(CH₂)₃COOH | OMe |
| 203 | His-Gly | -CH₂-phenyl | -(CH₂)₃COOH | -CH₂-(4-F-phenyl) | OMe |
| 204 | His-Gly | -CH₂-phenyl | -(CH₂)₃COOH | -CH₂CH₂-(4-OH-phenyl) | OMe |
| 205 | His-Gly | -CH₃ | -CH₂-phenyl | -CH₂-naphthyl | OMe |
| 206 | His-Gly | -CH₃ | -CH₂CH₂-phenyl | -CH₂-naphthyl | OMe |
| 207 | His-Gly | -CH₃ | -CH₂-(4-F-phenyl) | -CH₂-naphthyl | OMe |
| 208 | His-Gly | -CH₃ | -CH₂-naphthyl | -CH₂-naphthyl | OMe |

FIG. 13B (cont.)

| | | | | | |
|---|---|---|---|---|---|
| 209 | His-Gly | -CH₃ | 1-naphthylmethyl | 2-naphthylmethyl | OMe |
| 210 | His-Gly | -CH₃ | pentafluorobenzyl | 2-naphthylmethyl | OMe |
| 212 | His-Gly | -CH₃ | benzyl | pentafluorobenzyl | OMe |
| 213 | His-Gly | -CH₃ | benzyl | 1-naphthylmethyl | OMe |
| 214 | His-Gly | -CH₃ | 1-naphthylmethyl | 1-naphthylmethyl | OMe |
| 215 | His-Gly | -CH₃ | phenethyl | 1-naphthylmethyl | OMe |
| 216 | His-Gly | -CH₃ | sec-butyl | isopropyl | OMe |
| 217 | His-Gly | -CH₃ | 2-(3-thienyl)ethyl | 2-naphthylmethyl | OMe |
| 218 | His-Gly | -CH₃ | 2-(3-thienyl)ethyl | 1-naphthylmethyl | OMe |
| 219 | His-Gly | 4-fluorobenzyl | 4-fluorobenzyl | 4-fluorobenzyl | OMe |
| 220 | His-Gly | 2-naphthylmethyl | 2-naphthylmethyl | 2-naphthylmethyl | OMe |

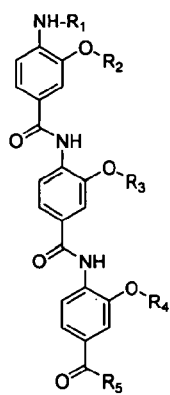

Structure:

FIG. 13C

| Compound No. | R1 | R2 | R3 | R4 | R5 |
|---|---|---|---|---|---|
| 221 | His | benzyl | isopropyl | 4-F-benzyl | OMe |
| 222 | His | phenethyl | isopropyl | 4-F-benzyl | OMe |
| 223 | His | pentafluorobenzyl | isopropyl | 4-F-benzyl | OMe |
| 224 | His | 4-F-benzyl | isopropyl | 4-F-benzyl | OMe |
| 225 | His | 4-OH-phenethyl | isopropyl | 4-F-benzyl | OMe |
| 226 | His | 2-naphthylmethyl | isopropyl | 4-F-benzyl | OMe |
| 227 | His | 1-naphthylmethyl | isopropyl | 4-F-benzyl | OMe |
| 228 | His | 3-thienylethyl | isopropyl | 4-F-benzyl | OMe |
| 229 | His | imidazolylethyl | isopropyl | 4-F-benzyl | OMe |
| 230 | His | benzyl | -CH₃ | 4-F-benzyl | OMe |
| 231 | His | benzyl | sec-butyl | 4-F-benzyl | OMe |
| 232 | His | benzyl | n-butyl | 4-F-benzyl | OMe |

FIG. 13C (cont.)

| | | | | | |
|---|---|---|---|---|---|
| 233 | His | benzyl | isopropyl | 4-F-benzyl | OMe |
| 234 | His | benzyl | cyclohexylmethyl | 4-F-benzyl | OMe |
| 235 | His | benzyl | cyclopropyl | 4-F-benzyl | OMe |
| 236 | His | benzyl | 4-F-benzyl | 4-F-benzyl | OMe |
| 237 | His | benzyl | benzyl | benzyl | OMe |
| 238 | His | benzyl | isobutyl | benzyl | OMe |
| 239 | His | benzyl | isopropyl | pentafluorobenzyl | OMe |
| 240 | His | benzyl | isopropyl | 4-OH-phenethyl | OMe |
| 241 | His | benzyl | isopropyl | 2-naphthylmethyl | OMe |
| 242 | His | benzyl | isopropyl | 1-naphthylmethyl | OMe |
| 243 | His | benzyl | isopropyl | thienylethyl | OMe |
| 244 | His | benzyl | isopropyl | imidazolylethyl | OMe |
| 245 | His | imidazolylethyl | imidazolylethyl | imidazolylethyl | OMe |
| 246 | His | imidazolylethyl | isopropyl | 4-OH-phenethyl | OMe |
| 247 | His | imidazolylethyl | isobutyl | 4-OH-phenethyl | OMe |
| 248 | His | benzyl | phenethyl | phenethyl | OMe |
| 249 | His | benzyl | pentafluorobenzyl | pentafluorobenzyl | OMe |
| 250 | His | −CH₃ | −CH₃ | −CH₃ | OMe |
| 251 | His | isopropyl | isopropyl | isopropyl | OMe |

FIG. 13C (cont.)

| | | | | | |
|---|---|---|---|---|---|
| 252 | His | isobutyl | isobutyl | isobutyl | OMe |
| 253 | His | n-butyl | n-butyl | n-butyl | OMe |
| 254 | His | CH₂CH₂OH | CH₂CH₂OH | CH₂CH₂OH | OMe |
| 255 | His | CH₂CH₂OH | CH₂CH₂OH | (CH₂)₃COOH | OMe |
| 256 | His | (CH₂)₃COOH | (CH₂)₄NH₂ | (CH₂)₃COOH | OMe |
| 257 | His | (CH₂)₄NH₂ | (CH₂)₃COOH | (CH₂)₄NH₂ | OMe |
| 258 | His | CH₂CH(OH)CH₃ | (CH₂)₃COOH | (CH₂)₄NH₂ | OMe |
| 259 | His | CH₂CH₂OH | (CH₂)₃COOH | (CH₂)₃NHC(=NH)NH₂ | OMe |
| 260 | His | (CH₂)₃COOH | (CH₂)₃NHC(=NH)NH₂ | (CH₂)₃COOH | OMe |
| 261 | His | (CH₂)₃NHC(=NH)NH₂ | (CH₂)₃NHC(=NH)NH₂ | (CH₂)₃NHC(=NH)NH₂ | OMe |
| 262 | His | CH₂-imidazole | CH₂CH₂-Ph | (CH₂)₃COOH | OMe |
| 263 | His | CH₂-Ph | (CH₂)₃COOH | CH₂-(4-F-Ph) | OMe |
| 264 | His | CH₂-Ph | (CH₂)₃COOH | CH₂CH₂-(4-OH-Ph) | OMe |
| 265 | His | -CH₃ | CH₂-Ph | CH₂-(2-naphthyl) | OMe |
| 266 | His | -CH₃ | CH₂CH₂-Ph | CH₂-(2-naphthyl) | OMe |
| 267 | His | -CH₃ | CH₂-(4-F-Ph) | CH₂-(2-naphthyl) | OMe |
| 268 | His | -CH₃ | CH₂-(2-naphthyl) | CH₂-(2-naphthyl) | OMe |
| 269 | His | -CH₃ | CH₂-(1-naphthyl) | CH₂-(2-naphthyl) | OMe |
| 270 | His | -CH₃ | CH₂-(pentafluorophenyl) | CH₂-(2-naphthyl) | OMe |

| # | | | | | |
|---|---|---|---|---|---|
| 272 | His | §-CH₃ |  |  | OMe |
| 273 | His | §-CH₃ |  |  | OMe |
| 274 | His | §-CH₃ |  |  | OMe |
| 275 | His | §-CH₃ |  |  | OMe |
| 276 | His | §-CH₃ |  |  | OMe |
| 277 | His | §-CH₃ |  |  | OMe |
| 278 | His | §-CH₃ |  |  | OMe |
| 279 | His |  |  |  | OMe |
| 280 | His |  |  |  | OMe |

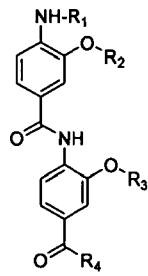

Structure:

FIG. 13D

| Compound No. | R1 | R2 | R3 | R4 |
|---|---|---|---|---|
| 281 | His | benzyl | 4-F-benzyl | OMe |
| 282 | His | phenethyl | 4-F-benzyl | OMe |
| 283 | His | pentafluorobenzyl | 4-F-benzyl | OMe |
| 284 | His | 4-F-benzyl | 4-F-benzyl | OMe |
| 285 | His | 4-OH-phenethyl | 4-F-benzyl | OMe |
| 286 | His | 2-naphthylmethyl | 4-F-benzyl | OMe |
| 287 | His | 1-naphthylmethyl | 4-F-benzyl | OMe |
| 288 | His | 3-thienylethyl | 4-F-benzyl | OMe |
| 289 | His | imidazolylethyl | 4-F-benzyl | OMe |
| 290 | His | -CH3 | 4-F-benzyl | OMe |
| 291 | His | isopropyl | 4-F-benzyl | OMe |
| 292 | His | sec-butyl | 4-F-benzyl | OMe |
| 293 | His | n-butyl | 4-F-benzyl | OMe |
| 294 | His | isobutyl | 4-F-benzyl | OMe |

| | | | | |
|---|---|---|---|---|
| 295 | His |  |  | OMe |
| 296 | His |  |  | OMe |
| 297 | His |  |  | OMe |
| 298 | His |  |  | OMe |
| 299 | His |  |  | OMe |
| 300 | His |  |  | OMe |
| 301 | His |  |  | OMe |
| 302 | His |  |  | OMe |
| 303 | His |  |  | OMe |
| 304 | His |  |  | OMe |
| 305 | His |  |  | OMe |
| 306 | His |  |  | OMe |
| 307 | His |  |  | OMe |
| 308 | His |  |  | OMe |
| 309 | His |  |  | OMe |
| 310 | His |  -CH$_3$ |  -CH$_3$ | OMe |
| 311 | His |  |  | OMe |
| 312 | His |  |  | OMe |
| 313 | His |  |  | OMe |
| 314 | His |  |  | OMe |

FIG. 13D (cont.)

| # | | R1 | R2 | R3 |
|---|---|---|---|---|
| 315 | His | 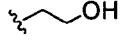 ethanol | 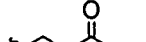 propanoic acid | OMe |
| 316 | His |  propanoic acid |  propanoic acid | OMe |
| 317 | His | 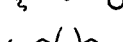 (CH2)2NH2 | 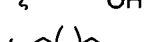 (CH2)2NH2 | OMe |
| 318 | His | 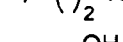 isopropanol | 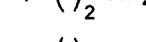 (CH2)2NH2 | OMe |
| 319 | His |  ethanol | 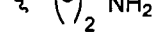 guanidinyl propyl | OMe |
| 320 | His |  propanoic acid | 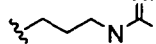 propanoic acid | OMe |
| 321 | His |  guanidinyl propyl |  guanidinyl propyl | OMe |
| 322 | His |  imidazole ethyl |  propanoic acid | OMe |
| 323 | His |  benzyl |  4-F-benzyl | OMe |
| 324 | His | 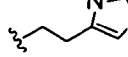 benzyl | 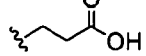 4-OH-phenethyl | OMe |
| 325 | His | -CH3 | 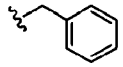 benzyl | OMe |
| 326 | His | -CH3 | 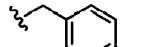 pentafluorobenzyl | OMe |
| 327 | His | -CH3 | 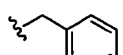 4-F-benzyl | OMe |
| 328 | His | -CH3 | 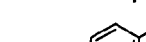 4-OH-phenethyl | OMe |
| 329 | His | -CH3 |  2-naphthylmethyl | OMe |
| 330 | His | -CH3 | 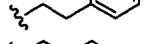 1-naphthylethyl | OMe |
| 332 | His | -CH3 |  thienyl ethyl | OMe |
| 333 | His | -CH3 | 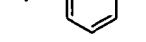 imidazole ethyl | OMe |

| 334 | His |  |  | OMe |
| 335 | His |  |  | OMe |
| 336 | His | ⌇-CH₃ |  | OMe |
| 337 | His |  |  | OMe |
| 338 | His | ⌇-CH₃ |  | OMe |
| 339 | His |  |  | OMe |
| 340 | His |  |  | OMe |

Structure: 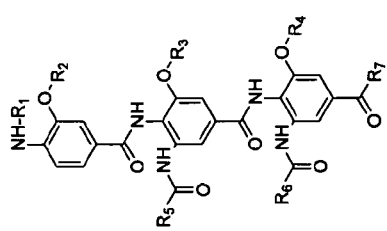

| Compound No. | R1 | R2 | R3 | R4 | R5 | R6 | R7 |
|---|---|---|---|---|---|---|---|
| 501 | Ac | benzyl | iPr | 4-F-benzyl | 3-hydroxypropyl | 4-F-benzyl | OMe |
| 502 | Ac | phenethyl | iPr | 4-F-benzyl | 3-hydroxypropyl | 4-F-benzyl | OMe |
| 503 | Ac | pentafluorobenzyl | iPr | 4-F-benzyl | 3-hydroxypropyl | 4-F-benzyl | OMe |
| 504 | Ac | 4-F-benzyl | iPr | 4-F-benzyl | 3-hydroxypropyl | 4-F-benzyl | OMe |
| 505 | Ac | 4-OH-phenethyl | iPr | 4-F-benzyl | 3-hydroxypropyl | 4-F-benzyl | OMe |
| 506 | Ac | 2-naphthylmethyl | iPr | 4-F-benzyl | 3-hydroxypropyl | 4-F-benzyl | OMe |

| | | | | | |
|---|---|---|---|---|---|
| 547 | Ac | ⸨-CH₃ | | | OMe |
| 548 | Ac | ⸨-CH₃ | | | OMe |
| 549 | Ac | ⸨-CH₃ | | | OMe |
| 550 | Ac | ⸨-CH₃ | | | OMe |
| 552 | Ac | ⸨-CH₃ | | | OMe |
| 553 | Ac | ⸨-CH₃ | | | OMe |
| 554 | Ac | ⸨-CH₃ | | | OMe |
| 555 | Ac | ⸨-CH₃ | | | OMe |
| 556 | Ac | ⸨-CH₃ | | | OMe |

| | | | | | | |
|---|---|---|---|---|---|---|
| 566 | His-Gly | naphthalen-2-ylmethyl | isobutyl | 4-fluorobenzyl | 3-hydroxypropyl | 4-fluorobenzyl | OMe |
| 567 | His-Gly | naphthalen-1-ylmethyl | isobutyl | 4-fluorobenzyl | 3-hydroxypropyl | 4-fluorobenzyl | OMe |
| 568 | His-Gly | thiophen-3-ylmethyl | isobutyl | 4-fluorobenzyl | 3-hydroxypropyl | 4-fluorobenzyl | OMe |
| 569 | His-Gly | imidazolylmethyl | isobutyl | 4-fluorobenzyl | 3-hydroxypropyl | 4-fluorobenzyl | OMe |
| 570 | His-Gly | benzyl | methyl | 4-fluorobenzyl | 3-hydroxypropyl | 4-fluorobenzyl | OMe |
| 571 | His-Gly | benzyl | isobutyl | 4-fluorobenzyl | 3-hydroxypropyl | 4-fluorobenzyl | OMe |
| 572 | His-Gly | benzyl | sec-butyl | 4-fluorobenzyl | 3-hydroxypropyl | 4-fluorobenzyl | OMe |
| 573 | His-Gly | benzyl | isobutyl | 4-fluorobenzyl | 3-hydroxypropyl | 4-fluorobenzyl | OMe |
| 574 | His-Gly | benzyl | cyclohexyl | 4-fluorobenzyl | 3-hydroxypropyl | 4-fluorobenzyl | OMe |
| 575 | His-Gly | benzyl | cyclopropyl | 4-fluorobenzyl | carboxypropyl | 4-fluorobenzyl | OMe |
| 576 | His-Gly | benzyl | 4-fluorobenzyl | 4-fluorobenzyl | carboxypropyl | 4-fluorobenzyl | OMe |
| 577 | His-Gly | benzyl | benzyl | phenyl | carboxypropyl | cyclopropyl | OMe |
| 578 | His-Gly | benzyl | isobutyl | phenyl | carboxypropyl | benzyl | OMe |

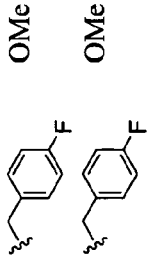

| | | | | | |
|---|---|---|---|---|---|
| 617 | His-Gly | ⸹-CH₃ | thiophen-3-yl-propyl | naphthalen-2-yl-ethyl | C(=O)NH₂ propyl | naphthalen-2-yl-methyl-OMe |
| 618 | His-Gly | ⸹-CH₃ | thiophen-3-yl-propyl | naphthalen-1-yl-ethyl | C(=O)NH₂ propyl | naphthalen-1-yl-methyl-OMe |
| 619 | His-Gly | 4-F-benzyl | 4-F-benzyl | 4-F-benzyl | CH(OH)ethyl | 4-F-benzyl-OMe |
| 620 | His-Gly | naphthalen-2-yl-ethyl | naphthalen-2-yl-ethyl | naphthalen-2-yl-ethyl | CH(OH)ethyl | naphthalen-2-yl-methyl-OMe |

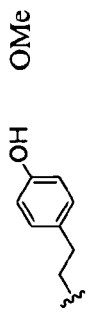

FIG. 13H (cont.)

Structure:

| Compound No. | R1 | R2 | R3 | R4 | R5 | R6 | R7 | R8 | R9 |
|---|---|---|---|---|---|---|---|---|---|
| 701 | Ac | CH2-Ph | iPr | CH2-C6H4-F | Gly | -CH3 | CH2-Ph | CH2-Naphthyl | OMe |

FIG. 13I (cont.)

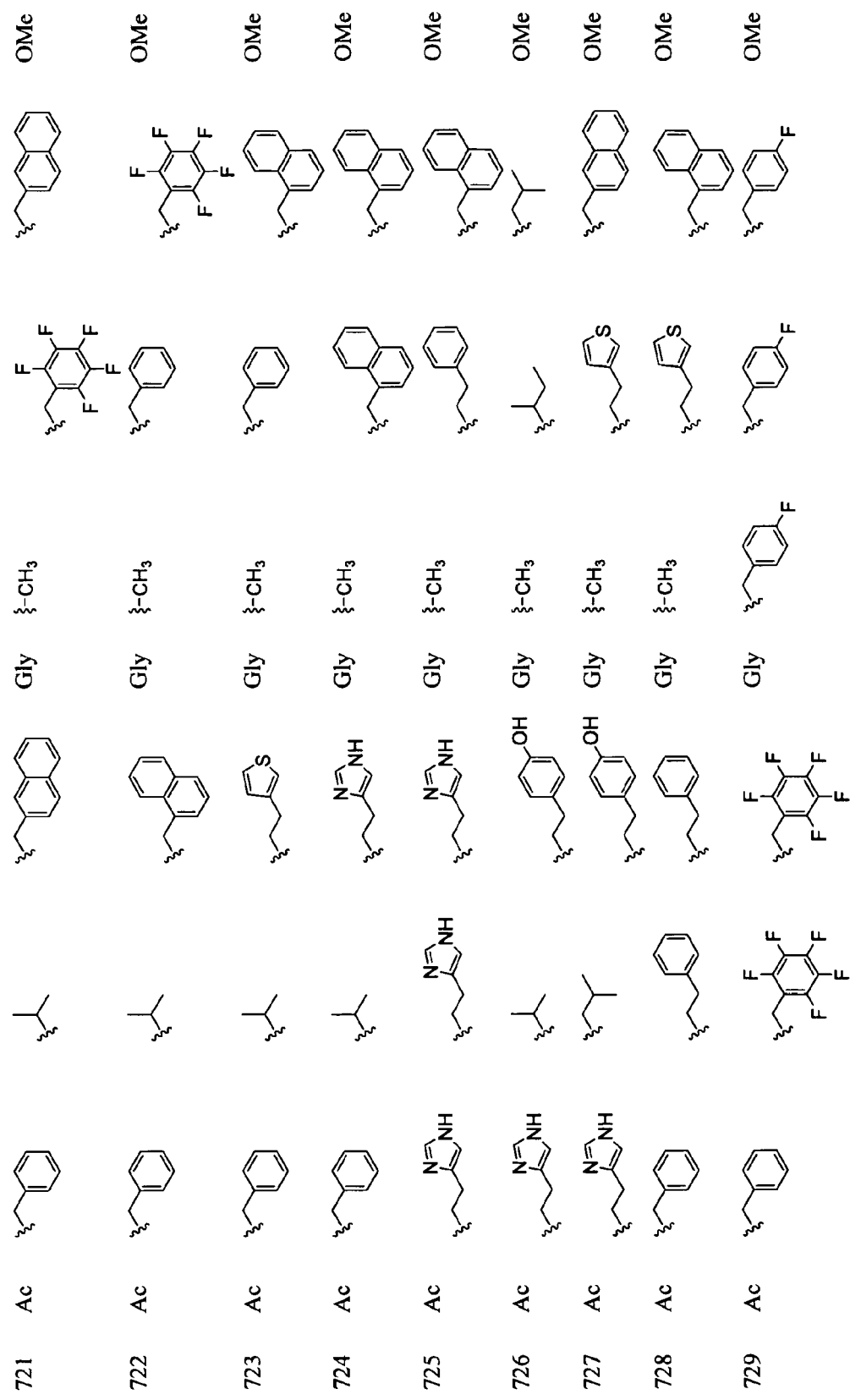

| Comp No. | R1 | R2 | R3 | R4 | R5 | R6 | R7 | R8 | R9 |
|---|---|---|---|---|---|---|---|---|---|
| 901 | His | benzyl | isopropyl | 4-fluorobenzyl | Gly | -CH₃ | benzyl | 2-naphthylmethyl | OMe |

SEQUENCE LISTING

<160> NUMBER OF SEQ ID NOS: 1

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

COMPOSITION AND METHOD FOR MAKING OLIGO-BENZAMIDE COMPOUNDS

CROSS-REFERENCE TO RELATED APPLICATIONS

This application claims priority to U.S. Provisional Application Ser. No. 60/894,580 filed Mar. 13, 2007, the contents of which is incorporated by reference herein in its entirety.

TECHNICAL FIELD OF THE INVENTION

The present invention relates in general to the field of peptidomimetics and specifically to compositions of matter, kits and methods of making oligo-benzamide peptidomimetic compounds.

BACKGROUND OF THE INVENTION

Without limiting the scope of the invention, its background is described in connection with compositions and methods of making the compositions that mimic peptides and proteins, using oligo-benzamide compositions. Proteins are one of the essential components for all living organisms and are utilized to maintain and regulate nearly all critical cellular functions—from intercellular communication to cell death. For their actions, proteins interact with diverse molecules, and among them protein-protein complex formation is an essential theme through which many regulatory processes like modulation of enzymatic activity, signal transduction, and apoptosis, are initiated or inhibited. Therefore, small molecules that inhibit protein-protein or protein-peptide interaction have been actively pursued in an attempt to develop potential therapeutic agents. Conventional methods for identifying such inhibitors include the preparation and screening of chemical libraries to discover lead compounds although often with little success.

SUMMARY OF THE INVENTION

The present inventor recognized that a rational design approach provides a compelling alternative to conventional methods. The present inventor recognized that based on a structural knowledge of the interface of protein complexes. The present inventor recognized that α-helix mimetics may be used to modulate protein-protein, protein-peptide interaction or other interactions. In particular, synthetic scaffolds that mimic key elements found in the interface can potentially lead to develop potent small molecule modulators. The present inventor recognized that the mimetics can be used to interact with complexes of various types. For example the mimetics can be used to interact with a peptide receptor, a hormone receptor, a drug receptor, chemical complexes, an enzyme, enzyme complexes, and other types of interactions. The present inventor also recognized that the mimetics may be used to interact with cellular proteins, surface proteins and protein complexes.

The present inventor recognized a need for stable small molecules possessing the capability to modulate protein functions without the limitations of the peptide structure. The present invention provides a class of small molecules that are stable and capable of interacting with other molecules or proteins but lacking the limitations of the peptide structure. These small molecules include α-helix mimetics that represent helical segments in the target molecules.

The oligo-benzamide peptidomimetic compound includes at least two optionally substituted benzamides, with each of the substituted benzamides having one or more substitutions on a benzene ring. The oligo-benzamide peptidomimetic compound modulates protein-protein, protein-peptide, or protein-drug interaction to exert a variety of physiological consequences.

Another embodiment of the present invention is the addition of a third optionally substituted benzamide connected to one of the at least two optionally substituted benzamides, and the third optionally substituted benzamide may include one or more substitutions on a benzene ring. The present invention also provides an oligo-benzamide peptidomimetic compound that includes at least two optionally substituted benzamides with one or more substitutions on a benzene ring.

The present invention also provides a peptidomimetic compound that at least partially modulates a protein including peptide receptors, enzymes, and cellular proteins. The peptidomimetic compound includes a tris-benzamide peptidomimetic, three optionally substituted benzamides and one or more substituted groups attached to each of the substituted benzamides individually by a chemical bond including ether, thioether, amine, aminde, carbamate, urea, and carbon-carbon (single, double, and triple) bonds.

The present invention provides a method for treating a subject that would benefit from modulating a protein including peptide receptors, enzymes, and cellular proteins by administering to the subject an oligo-benzamide peptidomimetic compound comprising more than two optionally substituted benzamides and one or more substituted groups attached to each of the substituted benzamides individually by a chemical bond including ether, thioether, amine, amide, carbamate, urea, and carbon-carbon (single, double, and triple) bonds. The pharmaceutical peptidomimetic compound may be adapted for oral, dermatological, transdermal or parenteral administration.

The subject proteins include peptides that may be either locally produced or may be generated elsewhere in the body and are transported to the target tissue via the blood stream. Binding of the peptide to a cognate receptor modulates a wide range of cellular functions such as intracellular signaling, growth, apoptosis, secretion, differentiation, electrical excitation or inhibition, gene expression, and many others.

Endogenous peptide ligands which act on peptide receptors typically have a distinct tertiary structure that enables these molecules to selectively recognize receptors with high affinity and to modulate their functions. One defining structural feature of such peptides are α-helices, i.e. structures in which the amino acid side chains are placed in a circular orientation with a characteristic angle of 100° between adjacent residues. The subject proteins also include enzymes, cellular proteins, and other proteins that are not involved in a peptide hormone-mediated signal transduction.

The present invention provides a pharmaceutical composition that includes a therapeutically effective amount of an oligo-benzamide compound or a salt, a solvate, or a derivative thereof having an oligo-benzamide compound and one or more pharmaceutically acceptable carriers. The oligo-benzamide compound includes more than two optionally substituted benzamides (e.g., substituted and/or non-substituted benzamides) and one or more substituted groups attached to each of the substituted benzamides individually by a chemical bond including ether, thioether, amine, amide, carbamate, urea, and carbon-carbon (single, double, and triple) bonds.

The present invention provides a peptidomimetic compound having the formulas:

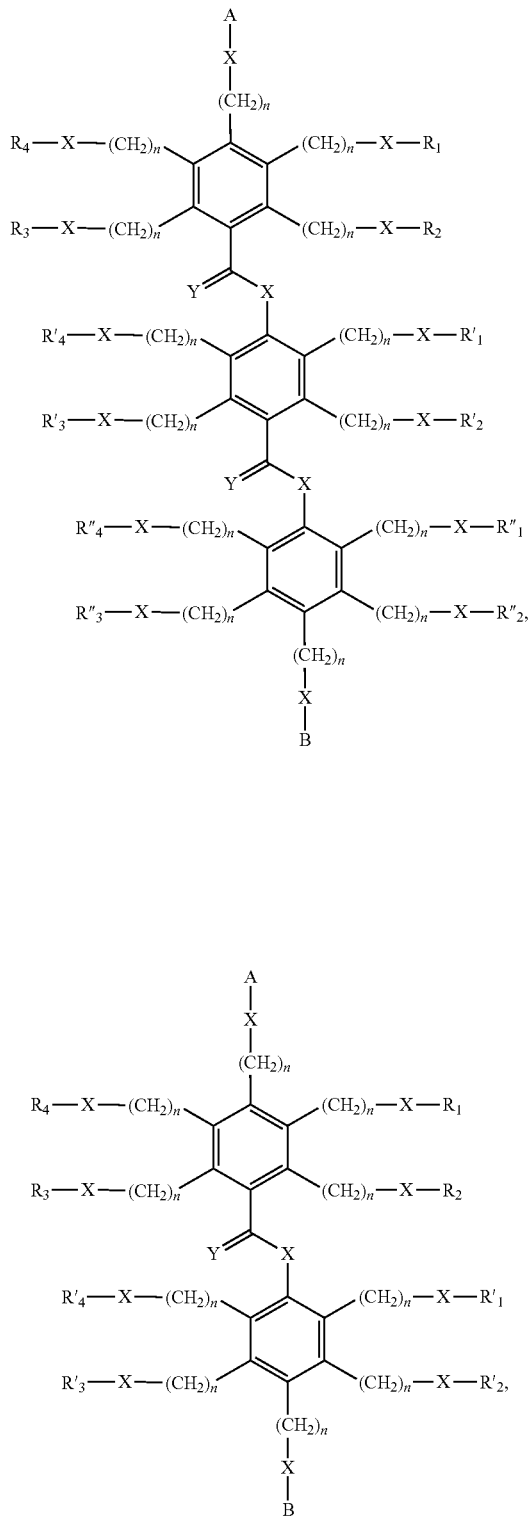

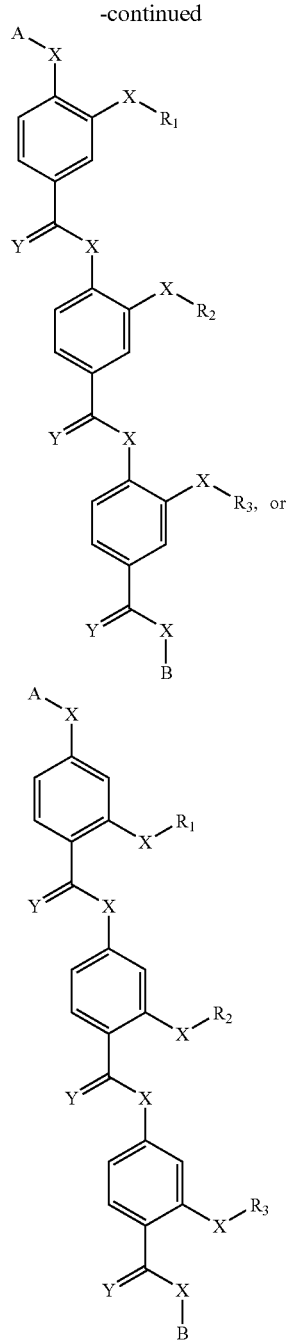

The present invention provides an oligo-benzamide peptidomimetic compound containing at least two optionally substituted benzamides. Each of the optionally substituted benzamides may be optionally substituted on the benzene ring with one or more substitutions.

BRIEF DESCRIPTION OF THE DRAWINGS

For a more complete understanding of the features and advantages of the present invention, reference is now made to the detailed description of the invention along with the accompanying figures and in which:

FIGS. 3A and 3B are images that illustrate various additional peptidomimetic compounds of the present invention that represent one α-helical face of a peptide;

DETAILED DESCRIPTION OF THE INVENTION

Figures 1A, 1B, 1C, 1D, 1E:
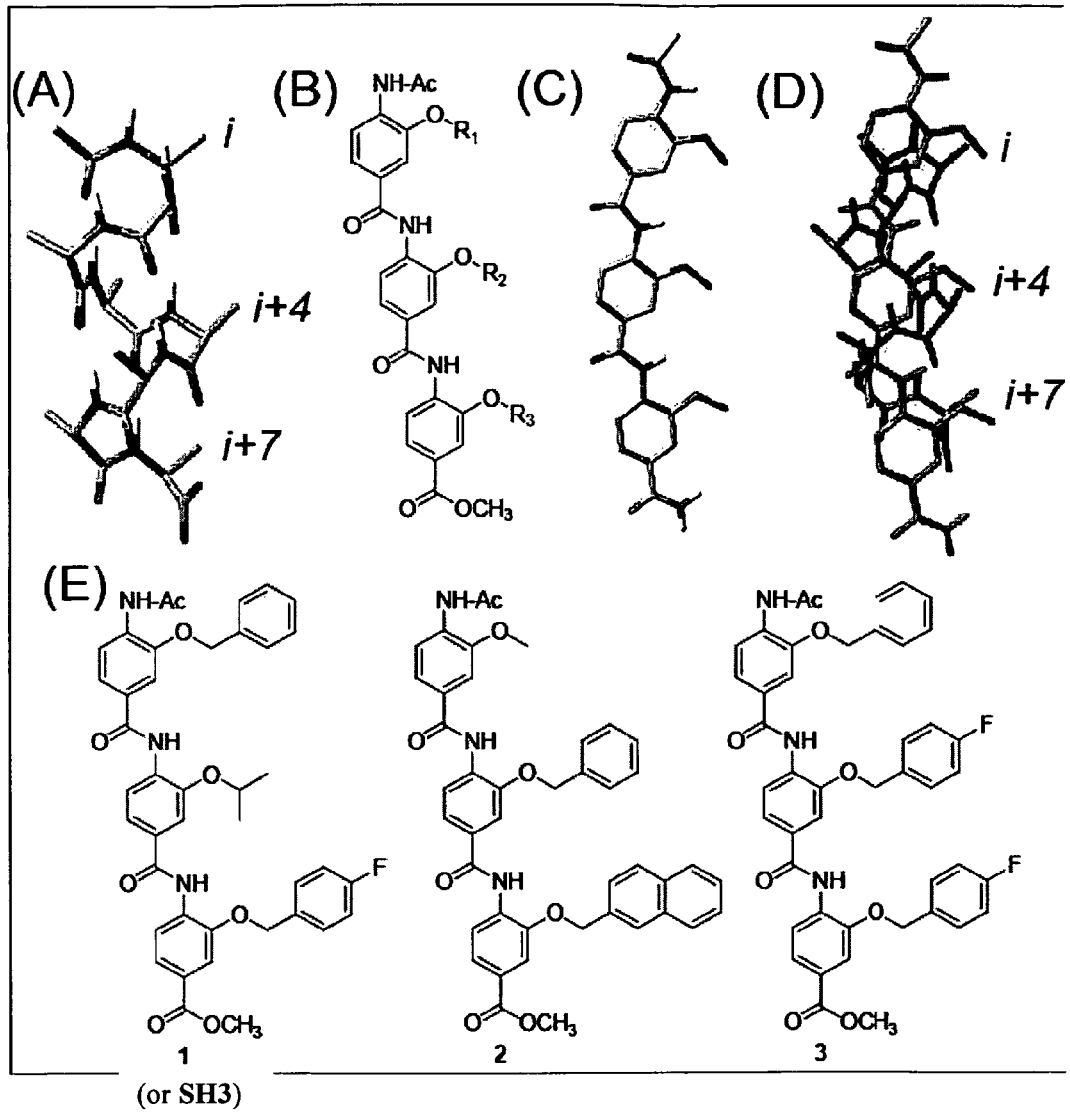
FIGS. 1A-1E are images of the structure of α-helix peptidomimetic compounds that represent one α-helical face of a peptide.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "Alkyl" denotes branched or unbranched hydrocarbon chains, having between about 1-20 carbons, with "lower Alkyl" denoting branched or unbranched hydrocarbon chains, having between about 1-10 carbons. Non-limiting examples include methyl, ethyl, propyl, n-propyl, isopropyl, butyl, n-butyl, sec-butyl, isobutyl, t-butyl, 1-methylpropyl, pentyl, isopentyl, sec-pentyl, 2-methylpentyl, hexyl, heptyl, octyl, nonyl, decyl, octadecyl and so on. Alkyl includes cycloalkyl, such as cyclopropyl, cyclobutyl, cyclopentyl, and cyclohexyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino, and the like to form alkyl groups such as trifluoro methyl, 3-hydroxyhexyl, 2-carboxypropyl, 2-fluoroethyl, carboxymethyl, cyanobutyl and the like.

As used herein, the term "Aryl" denotes a chain of carbon atoms which form at least one aromatic ring having between about 4-20 carbon atoms, such as phenyl, naphthyl, biphenyl, anthracenyl, pyrenyl, tetrahydronaphthyl, and so on, any of which may be optionally substituted. Aryl also includes arylalkyl groups such as benzyl, phenethyl, and phenylpropyl. Aryl includes a ring system containing an optionally substituted 5 or 6-membered carbocyclic aromatic ring, said system may be bicyclic, polycyclic, bridge, and/or fused. The system may include rings that are aromatic, or partially or completely saturated. Examples of ring systems include phenyl, naphtyl, biphenyl, anthracenyl, pyrenyl, imidazolyl, triazolyl, tetraazolyl, oxazolyl, thiophenyl, pyridyl, pyrrolyl, furanyl, quinolyl, quinolinyl, indenyl, pentalenyl, 1,4-dihydronaphthyl, indanyl, benzimidazolyl, benzothiophenyl, indolyl, benzofuranyl, isoquinolinyl, and so on. The group may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, carboxamidyl, alkoxycarbonyl, carbamyl, alkyl, alkenyl, alkynyl, nitro, amino, alkoxy, amido, imino, imido, guanidino, hydrazido, aminoxy, alkoxyamino and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, aminophenyl, amidophenyl, thiazolylphenyl, oxazolylphenyl, imidazolylphenyl, imidazolylmethylphenyl, and the like.

As used herein, the term "Alkenyl" includes optionally substituted straight chain and branched hydrocarbons having between about 1-50 carbons as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbons having a mixture of double bonds and triple bonds, such as 2-penten-4-ynyl, are grouped as alkynyls herein. Alkenyl includes cycloalkenyl. Cis and trans or (E) and (Z) forms are included within the invention. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "Alkynyl" includes optionally substituted straight chain and branched hydrocarbons having between about 1-50 carbons as above with at least one carbon-carbon triple bond (sp). Alkynyls include ethynyl, propynyls, butynyls, and pentynyls. Hydrocarbons having a mixture of double bonds and triple bonds, such as 2-penten-4- ynyl, are grouped as alkynyls herein. Alkynyl does not include cycloalkynyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, carboxamidyl, alkoxycarbonyl, carbamoyl, alkyl, alkenyl, alkynyl, nitro, amino, alkoxy, amido, imino, imido, guanidino, hydrazido, aminoxy, alkoxyamino and the like to form alkyl groups such as trifluoro methyl, 3-hydroxyhexyl, 2-carboxypropyl, 2-fluoroethyl, carboxymethyl, cyanobutyl and the like.

As used herein, the term "Alkoxy" includes an optionally substituted straight chain or branched alkyl group having between about 1-50 carbons with a terminal oxygen linking the alkyl group to the rest of the molecule. Alkoxy includes methoxy, ethoxy, propoxy, isopropoxy, butoxy, t-butoxy, pentoxy and so on. Alkyoxy also includes any substituted alkyl group connected by an ether linkage, such as aminobutoxy, carboxyethoxy, hydroxyethoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

As used herein, the term "pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

As used herein, the term "Pharmaceutically Acceptable Salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically Acceptable Salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention provides an oligo-benzamide peptidomimetic compound as illustrated includes 2 or 3 optionally substituted benzamides, the number of optionally substituted benzamides may be 4, 5, 6, 7, 8, 9, 10 or more. In addition, linkages between the optionally substituted benzamides may be varied as necessary including ester, thioester, thioamide, trans-ethylene, ethyl, methyloxy, methylamino, hydroxyethyl, carbamate, urea, imide, hydrozido, aminoxy, or other linkages known to the skilled artisan. And, the oligobenzamide peptidomimetic compound may be attached to amino acids, oligopeptides, optionally substituted alkyl, or other structures known to the skilled artisan.

The substitutions on the substituted benzamide are generally on a benzene ring and may be on the 2, 3, 4, 5, or 6 position of each of the benzene rings. The substitutions may be at the same position on each of the benzamide rings but may also be at different positions on each of the benzene rings. The one or more substitutions may include any necessary functional groups to achieve the desired effect. For example, the one or more substitutions are connected to the benzamide ring by a chemical linkage including ether, thioether, amine, amide, carbamate, urea, and carbon-carbon (single, double, and triple) bonds, and the one or more substitutions comprise one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, carboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The present invention also provides an oligo-benzamide peptidomimetic compound that includes at least two optionally substituted benzamides, with each of the substituted benzamides having one or more substitutions on a benzene ring. The one or more substitutions are individually attached to the benzene rings of the oligo-benzamide peptidomimetic compound by a chemical linkage including ether, thioether, amine, amide, carbamate, urea, and carbon-carbon (single, double, and triple) bonds. The one or more substitutions generally include one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof.

The substitutions may be on a single first face of the oligo-benzamide peptidomimetic compound to form an α-helix oligo-benzamide peptidomimetic compound or on two faces of the oligo-benzamide peptidomimetic compound to form an amphiphilic α-helix oligo-benzamide peptidomimetic compound.

A third optionally substituted benzamide with one or more optional substitutions on a benzene ring may be connected to one of the at least two optionally substituted benzamides. The present invention also provides an oligo-benzamide peptidomimetic compound having one or more substitutions on a first face and a second face of the oligo-benzamide peptidomimetic compound, wherein an amphiphilic α-helix oligo-benzamide peptidomimetic is formed. The one or more substitutions are at one or more positions of the oligo-benzamide peptidomimetic selected from an i position, an i+2 position, an i+3 position, an i+4 position, an i+5 position, and an i+7 position of a target peptide hormone. For example, one of the one or more substitutions correspond to an i position, one of the one or more substitutions correspond to an i+3 position or an i+4 position, and one of the one or more substitutions correspond to an i+7 position of a target peptide hormone.

The pharmaceutical peptidomimetic composition includes a therapeutically effective amount of an oligo-benzamide peptidomimetic compound or a salt, a solvent, or a derivative thereof based on an oligo-benzamide peptidomimetic compound, and one or more pharmaceutically acceptable carriers. For example, the tris-benzamide peptidomimetic compound includes three optionally substituted benzamides and one or more substituted groups attached to each of the substituted benzamides individually by a chemical linkage including ether, thioether, amine, amide, carbamate, urea, and carbon-carbon (single, double, and triple) bonds. The pharmaceutical peptidomimetic composition may also include one or more additional active ingredients, diluents, excipients, active agents, lubricants, preservatives, stabilizers, wetting agents, emulsifiers, salts for influencing osmotic pressure, buffers, colorings, flavorings, aromatic substances, penetration enhancers, surfactants, fatty acids, bile salts, chelating agents, colloids and combinations thereof. The pharmaceutical peptidomimetic compound may be adapted for oral, dermatological, transdermal or parenteral administration, in the form of a solution, a emulsions, a liposome-containing formulation, a tablet, a capsule, a gel capsule, a liquid syrup, a soft gel, a suppository, an enema, a patch, an ointment, a lotion, a cream, a gel, a drop, a spray, a liquid or a powder.

The present invention provides peptidomimetic compounds having the formulas:

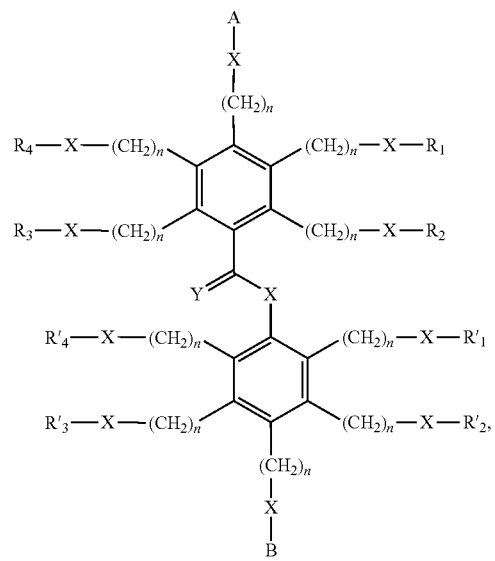

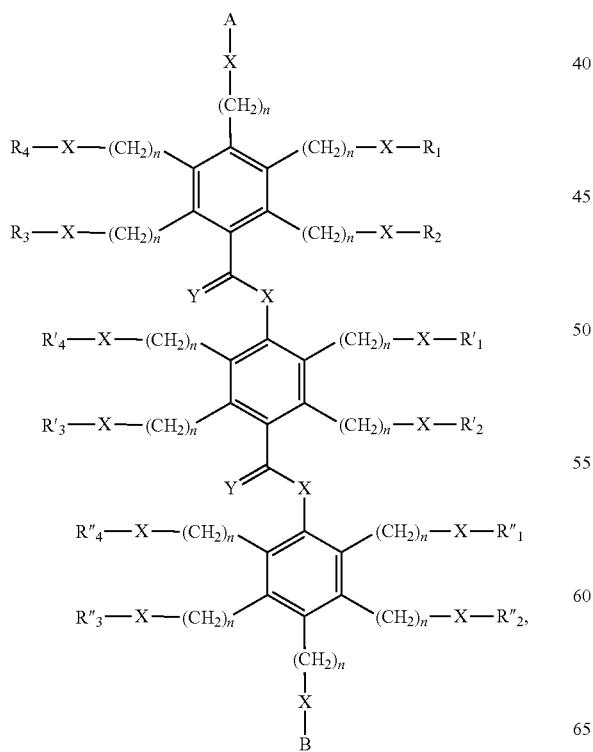

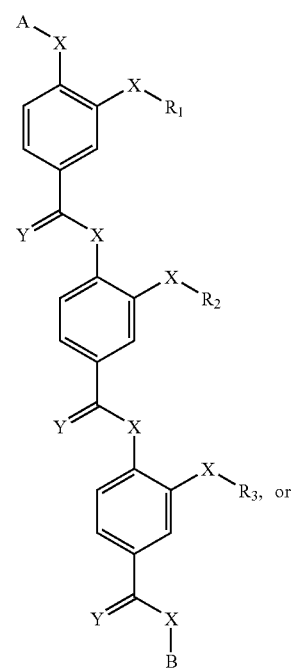

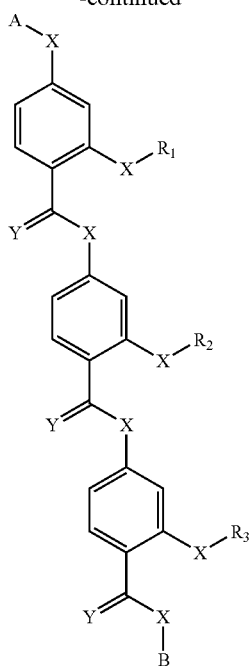

wherein each of the formulas may be substituted as follows. X may independently be a C, a N, a O, a S, a H, —CH$_2$CH$_2$—, —CH=CH—, —C≡C—, —NH—, —NR—, —NH—NH—, —NH(CH$_2$)$_n$NH, —NR(CH$_2$)$_n$NR'— —NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof, and Y may be independently a N, a O, a 5 or 2 H's. And, n is 0, 1, 2, 3, 4, 5, 6, 7 etc.

R1, R2, R3, R4, R'1, R'2, R'3, R'4, R"1, R"2, R"3, and R"4, comprise independently a H, optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkyl-alkyl, arylthio, alkylthio, alkylsulfinyl, alkylsulfonyl, arylsulfonyl, arylsulfinyl, caboxamido, carbamoyl, carboxyl, carbonyl, alkoxycarbonyl, halogen, haloalkyl, haloalkoxy, heteroayl, heterocyclic ring, arylheterocyclic ring, heterocyclic compounds, amido, imido, guanidino, hydrazido, aminoxy, alkoxyamino, alkylamido, urea, carboxylic ester, thioether, carboxylic acid, phosphoryl groups, polycyclic aromatic substituted with a OH, NH$_2$, SH, F, Cl, Br, I, NHR, NRR', CN$_3$H$_4$, a N, a O, a S, a H, or combination thereof.

Alternatively, R1, R2, R3, R4, R'1, R'2, R'3, R'4, R"1, R"2, R"13, and R"14 may be one or more of the following:

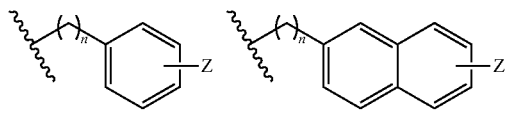

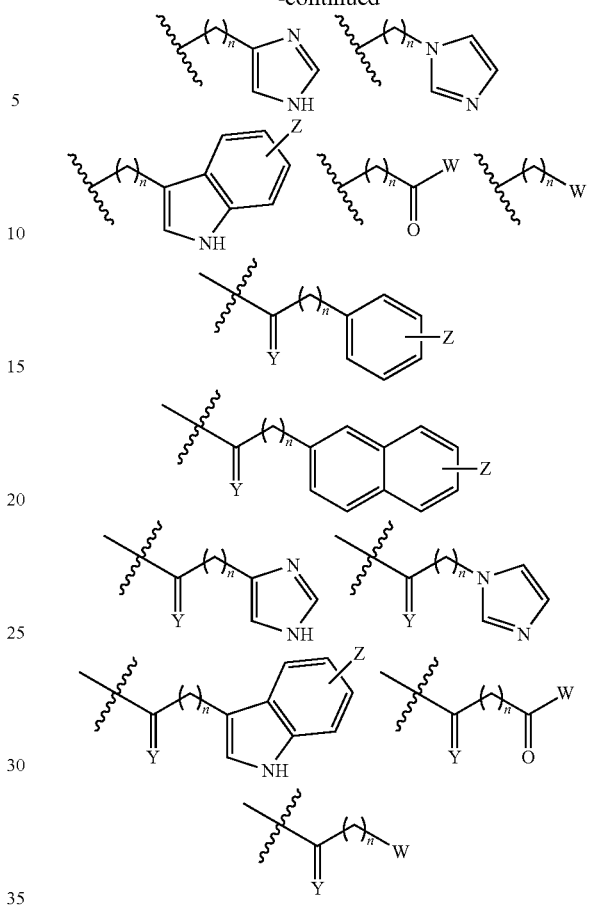

where Z is an OH, NH$_2$, SH, F, Cl, Br, I. W is an OH, an OR, a NH$_2$, a NHR, a NRR'(R, R' are alkyl groups), and an imine (C(NH)R$_1$R$_2$. For example, when R$_1$ is a NH$_2$ and R$_2$ is a NH the imine is actually a guanidine group), and n is 0, 1, 2, 3, 4, 5, 6, 7 etc.

"A" may be a substituent (R1, R2, R3, R4, R'1, R'2, R'3, R'4, R"1, R"2, R"3, or R"4), an acetyl, a Boc (t-butoxycarbonyl), a Fmoc (9-fluorenylmethoxycarbonyl), a Cbz (benzyloxycarbonyl), an Aloc (allyloxycarbonyl), an alkyl group, an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, dipeptide, tripeptide, tetrapeptide, pentapeptide, oligopeptide.

In addition "A" may be a linker as seen below

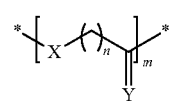

connected to a substituent (R1, R2, R3, R4, R'1, R'2, R'3, R'4, R"1, R"2, R"3, or R"4), an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, dipeptide, tripeptide, tetrapeptide, pentapeptide, oligopeptide.

"B" may be a substituent (R1, R2, R3, R4, R'1, R'2, R'3, R'4, R"1, R"2, R"3, or R"4), an alanine, an arginine, an asparagine, an aspartic acid, a cysteine, a glutamic acid, a glutamine, a glycine, a histidine, an isoleucine, a leucine, a lysine, a methionine, a phenylalanine, a proline, a serine, a threonine, a tryptophan, a tyrosine, a valine, an alkyl group, dipeptide, tripeptide, tetrapeptide, pentapeptide, oligopeptide.

In addition "B" may be a dipeptide which has greater than 50% sequence homology to a portion of the GLP-1 sequence SEQ. ID. NO.: 1, a tripeptide which has greater than 50% sequence homology to a portion of the GLP-1 sequence SEQ. ID. NO.: 1, a tetrapeptide which has greater than 50% sequence homology to a portion of the GLP-1 sequence SEQ. ID. NO.: 1, a pentapeptide which has greater than 50% sequence homology to a portion of the GLP-1 sequence SEQ. ID. NO.: 1, an oligopeptide which consists of no greater than 30 amino acids and has greater than 50% sequence homology to a portion of the GLP-1 sequence SEQ. ID. NO.: 1, connected to compounds M1 to M12 of FIG. 15, or 19A to 19B of FIG. 19. In addition "B" may be a linker as seen below

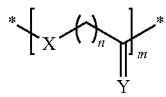

connected to a substituent (R1, R2, R3, R4, R'1, R'2, R'3, R'4, R"1, R"2, R"3, or R"4), an alkyl group, or one or more compounds M1 to M12 of FIG. 15, or 19A to 19B of FIG. 19.

The present invention provides an oligo-benzamide peptidomimetic compound having the formula:

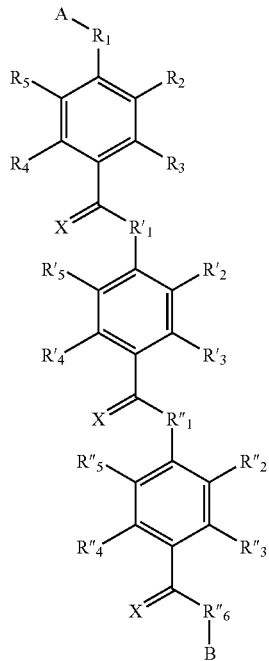

wherein R2, R3, R4, R5, R'2, R'3, R'4, R'5, R"2, R"13, R"14, and R"15 independently comprise a H, one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, urea groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof, R1, R'1, R"1 independently comprise a C, a N, a O, a S, a H, —CH$_2$CH$_2$—, —CH═CH—, —C≡C—, —NH—, —NR—, —NH—NH—, —NH(CH$_2$)$_n$NH, —NR(CH$_2$)$_n$NR'— —NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof, X comprises a N, a O, a S or 2 Hs; R"6 comprises a C, a N, a O, a S, a H, —CH$_2$CH$_2$—, —CH═CH—, —C≡C—, —NH—, —NR—, —NH—NH—, —NH(CH$_2$)$_n$NH, —NR(CH$_2$)$_n$NR'— —NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof, "A" comprises an acetyl, Boc, 9-fluorenylmethyl carbamate, Cbz, Aloc, an amino acid, an amino acid analogue, an artificial amino acid, a dipeptide, a tripeptide, a tetrapeptide, a pentapeptide, a peptide sequence of between 2 and 30 amino acids, a linker of 1-20 amino acids, a linker of an optionally substituted lower alkyl, a linker of an optionally substituted C1-C7 alkyl or a combination thereof, and "B" comprises an optionally substituted lower alkyl, an optionally substituted C1-C7 alkyl, an amino acid, an amino acid analogue, an artificial amino acid, a dipeptide, a tripeptide, a tetrapeptide, or a pentapeptide; a peptide sequence of between 2 and 30 amino acids; a linker of 1-20 amino acids, C1-C7 alkyl or combination thereof, which may also be connected to one or more compounds M1 to M 12 of FIG. 15, or 19A to 19B of FIG. 19.

Figure 10:
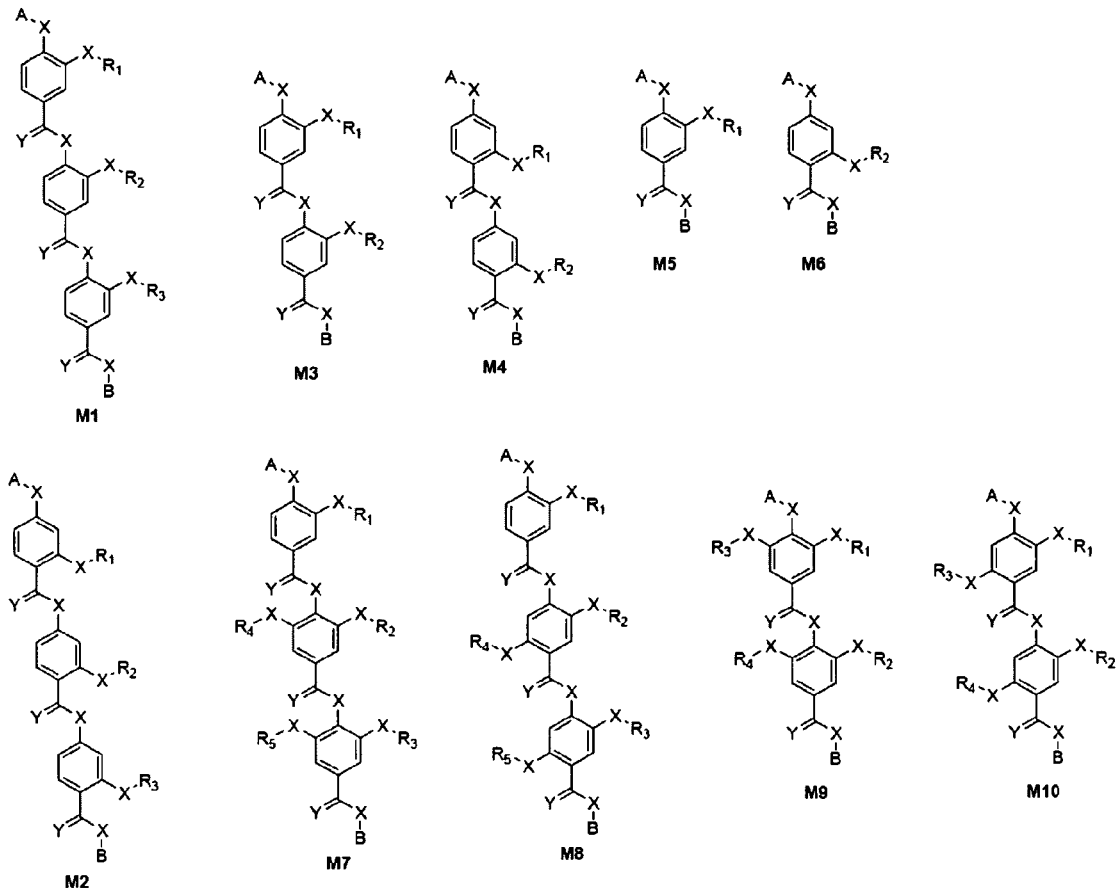
FIG. 10 is an image of various optionally substituted oligobenzamide α-helix peptidomimetic compounds.
Figure 10:
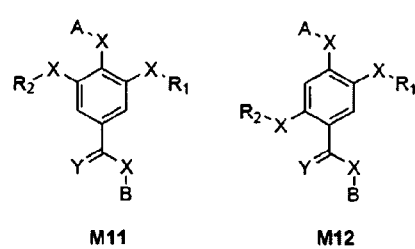
Figure 14:
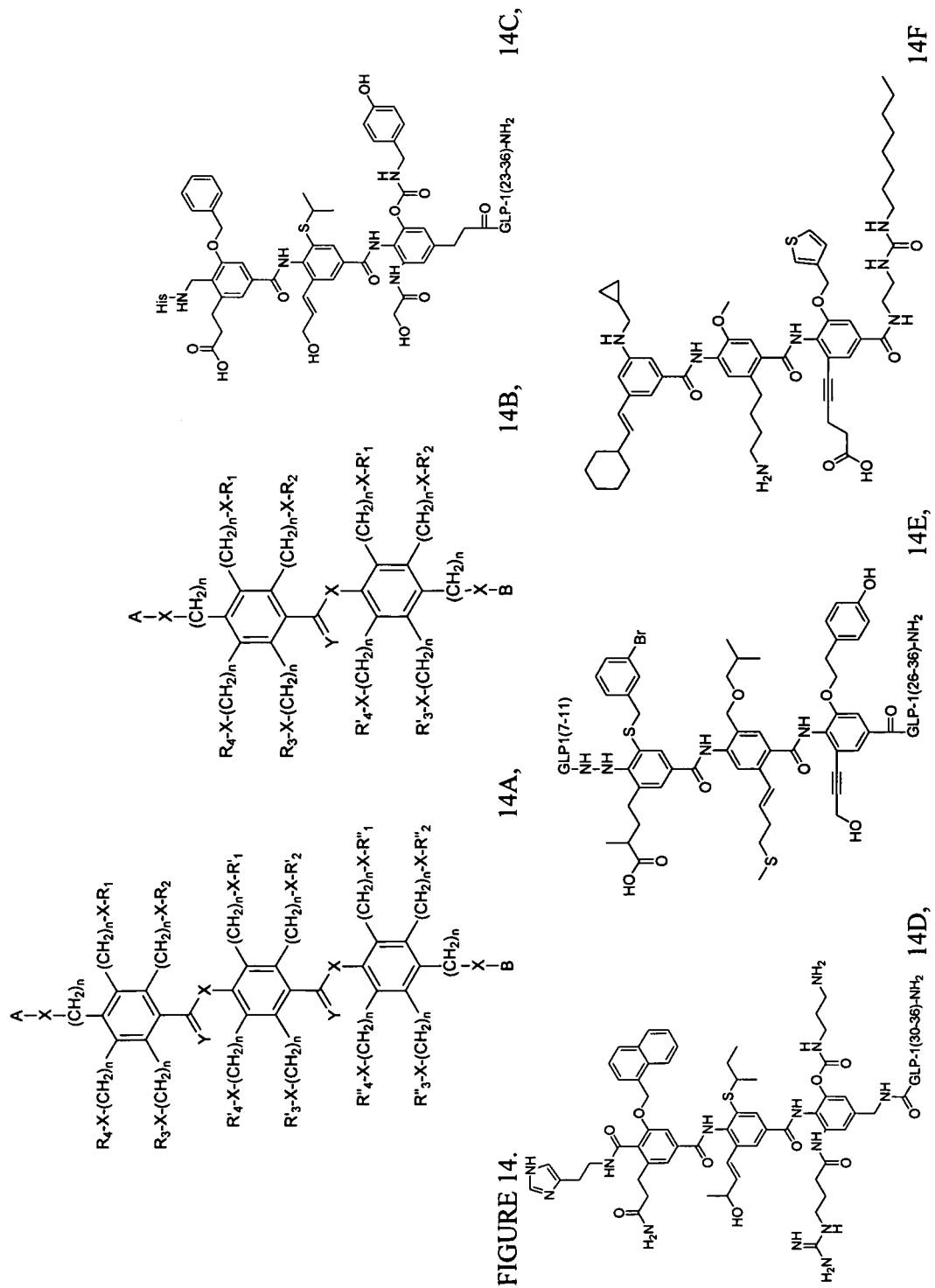
FIGS. 14A-14F are structures of another subset of the α-helix mimetics compounds described in the current invention.

One example includes a peptidomimetic compound having the formula:

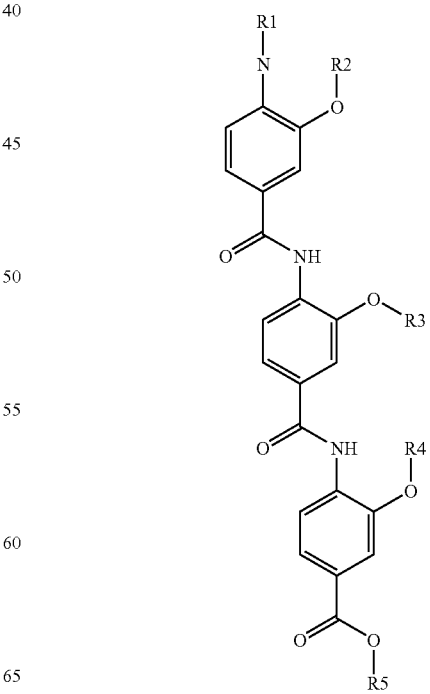

wherein R1, R2, R3, R4 and R5 individually comprise a C, a N, a O, a S, a H, one or more optionally substituted alkyl groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, urea groups, carboxylic ester groups, thioethers groups, carboxylic acids, phosphoryl groups or combination thereof, an acetyl, a Boc (t-butoxycarbonyl), a Fmoc (9-fluorenylmethoxycarbonyl), a Cbz (benzyloxycarbonyl), an Aloc (allyloxycarbonyl), an amino acid, an amino acid analogue, an artificial amino acid, a dipeptide, a tripeptide, a tetrapeptide, a pentapeptide, a linker of 1-20 amino acids, a linker of an optionally substituted lower alkyl, a linker of an optionally substituted C1-C7 alkyl, a polycyclic aromatic substituted with a OH, a $NH_2$, a SH, a F, a Cl, a Br, a I, a NHR, a NRR', a guanidine ($CN_3H_4$), a N, a 0, a S, a H, a peptide sequence of between 2 and 30 amino acids, a linker of 1-20 amino acids, an optionally substituted C1-C7 alkyl or a combination thereof, which may also be connected to one or more compounds M1 to M12 of FIG. 10 or 14A to 14B of FIG. 14. One specific example includes an R1 that is an acetyl group, R2 that is a benzyl group, R3 and R4 that are 4-fluorobenzyl groups, and R5 that is a methyl group; or where R1 is a t-butoxycarbonyl group, R2 is a methyl group, R3 is a benzyl group, R4 is a 2-naphthylmethyl group, and R5 is a methyl group.

The present invention provides synthetic molecules which present the essential functionalities of corresponding peptide ligands in the proper three dimensional orientation that enables specific receptor interactions, leading to either stimulation or inhibition of receptor-mediated functions.

Peptidomimetics (also known as peptide mimetics) are small organic compounds which lack the peptide backbone of native peptides. Despite this modification, they still retain an ability to interact with corresponding receptors or enzymes by presenting essential chemical functionalities (i.e., pharmacophores) in characteristic three-dimensional patterns which are complimentary to the target proteins.[52,53] Thereby, peptidomimetics potentially combine the advantages of peptides (e.g., high efficacy and selectivity, low side effects) and small organic molecules (e.g., high enzymatic stability and oral bioavailability).

To mimic α-helices, the present invention provides a new scaffold, oligo-benzamide, that is rigid in structure and place and orient substituents as an α-helix does. Substitution on the rigid tris-benzamide, for instance, allowed easy placement of three functional groups ($R_{1-3}$) corresponding to the side chains of amino acids found at the i, i+4, and i+7 positions of an ideal α-helix, representing one helical face as shown in FIG. 1. Furthermore, the present inventors have developed a facile synthetic route to prepare a number of tris-benzamides to represent α-helical segments of target proteins.

FIGS. 1A-1E are images of the structure of α-helix peptidomimetic compounds. FIG. 1A is an image of the structure of the α-helix peptidomimetic compounds, FIG. 1B is an image of the general structure of the α-helix peptidomimetic compounds, FIG. 1C is an image of the energy-minimized structure of an α-helix peptidomimetic compound, FIG. 1D is an image of the superimposition of the structure of an α-helix peptidomimetic (orange) with an α-helix (green), and FIG. 1E is an image of the structures of the α-helix peptidomimetic compounds 1, 2 and 3.

As seen in FIG. 1B the substitution on the oligo-benzamide structure allows the placement of three functional groups corresponding to the amino acids at the i, i+4, and i+7 positions, representing one face of a helix as can be seen in FIG. 1A. The structure of the designed α-helix mimetic compounds was analyzed by molecular modeling using MacroModel[80] (version 9, Schrödinger, New York, N.Y.). A Monte Carlo conformational search was carried out (5,000 steps) using a MM3 force fields[81] implemented into the software. The energy-minimized structure is seen in FIG. 1C and demonstrates that the three functional groups in the mimetic overlap well with the corresponding side chains of a helix seen in FIG. 1D.

Figure 2:
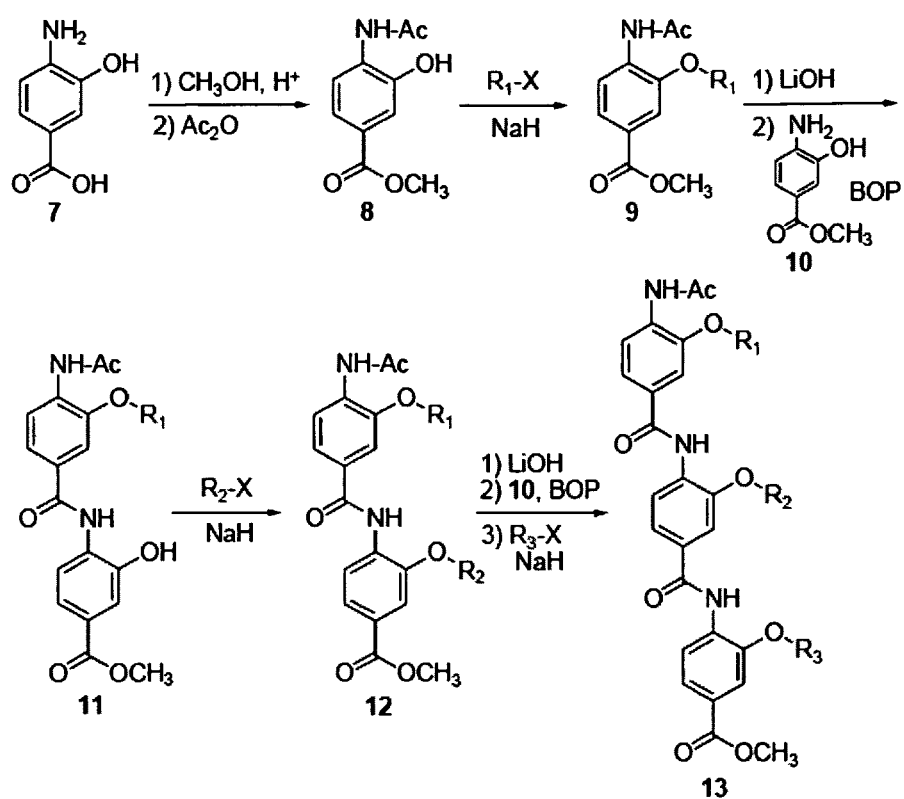
FIG. 2 is a synthesis scheme for the preparation of peptidomimetic compounds of the present invention that represent one α-helical face of a peptide.

FIG. 2 is a synthesis scheme to prepare α-helix mimetic compounds of the present invention. For example, fifteen α-helix mimetic compounds were made starting with a 4-amino-3-hydroxybenzoic acid compound 7, which was converted to an N-Ac protected methyl ester compound 8. Various alkyl groups were introduced to the hydroxyl group using a variety of alkyl halides and a base (e.g., NaH) known to the skilled artisan. After the alkylation reaction, the methyl ester compound 9 was hydrolyzed using a base (like LiOH), and methyl 4-amino-3-hydroxybenzoate compound 10 was coupled to the free benzoic acid using a coupling reagent (like BOP), resulting in a benzamide compound II containing one alkyl group corresponding to the i position of a helix. These steps were repeated to synthesize oligo-benzamide compounds.

FIGS. 3A and 3B are images that illustrate various α-helix mimetic compounds of the present invention. FIG. 3A provides the basic structure indicating the modification locations R1, R2 and R3, which may be substituted with various groups to provide different characteristics. For example, FIG. 3B is a table of the substitutions at R1, R2 and R3 and provides the structures of the α-helix mimetic compounds 13A-13O. The alkylation and coupling reactions were repeated to place two other functional groups corresponding to the i+3 (or i+4) and i+7 positions, to prepare the α-helix mimetic compounds 13A-13O.

Given an α-helix has 3.6 residues per turn, the amino acids on the same helical face are at the i, i+3 (or i+4) and i+7 positions. By considering this spatial arrangement given by the α-helix mimetic compound 13, five α-helix mimetic compounds can be designed from the N-terminal helical segment and ten α-helix mimetic compounds can be designed from the C-terminal helical segment as seen in FIG. 3B.

Figure 4:
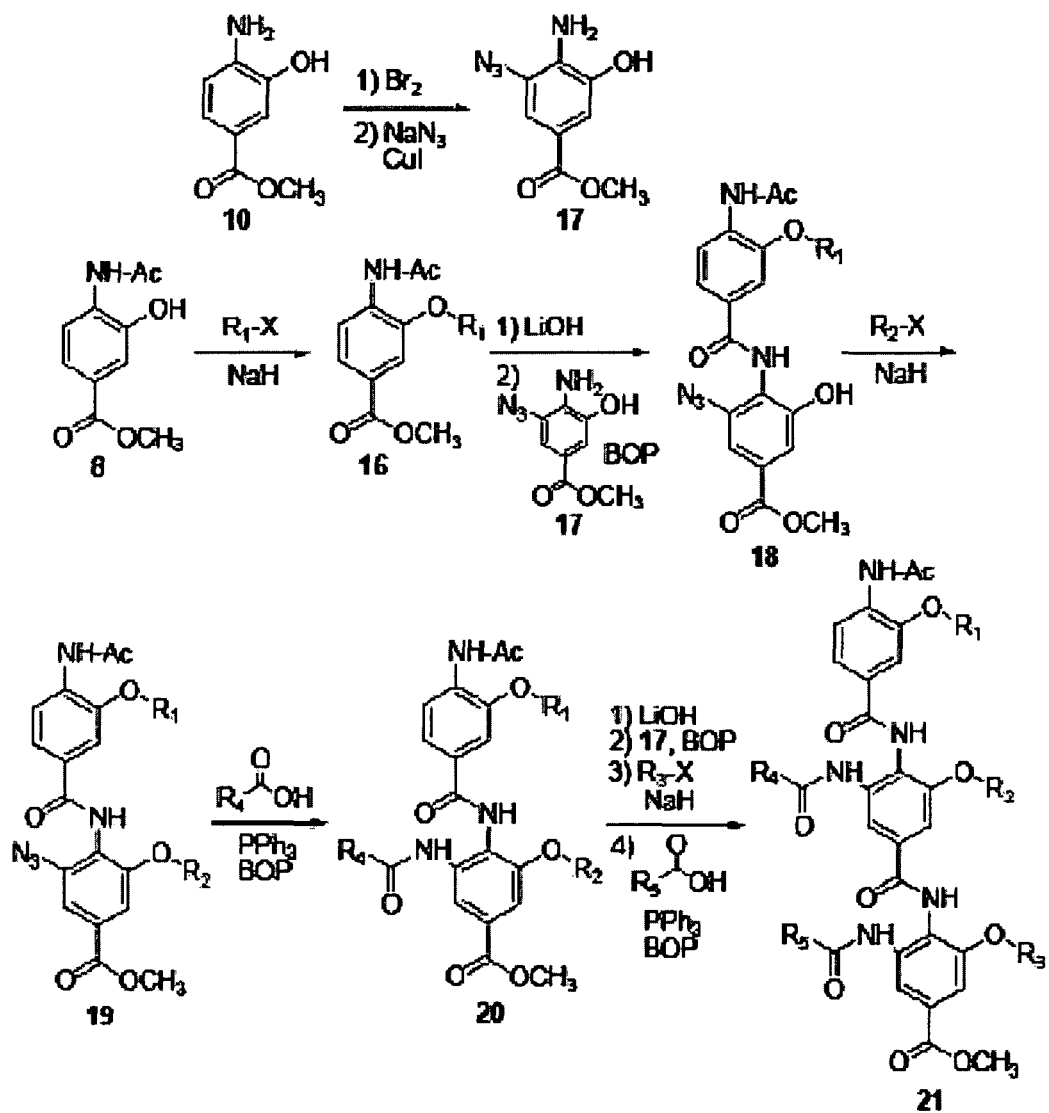
FIG. 4 is a scheme for the synthesis of peptidomimetic compounds of the present invention that represent two α-helical faces of a peptide.

FIG. 4 is a synthetic scheme for the preparation of amphiphilic α-helix mimetics of the present invention. The present invention provides amphiphilic α-helix mimetic compounds that present functional groups on both helical faces by modifying a benzamide scaffold and using a 3-azido-4-amino-5-hydroxybenzoic acid as a building block as seen in FIG. 4. The hydroxyl group at the 5-position carries a functional group corresponding to the side chain at the i+3 (or i+4) or i+7 position on one face of a helix, and the azide at the 3-position is converted to an amine to hold the functional group corresponding to the side chain at the i+2 or i+5 position on the opposite face of the helix.

In FIG. 4, the synthesis of amphiphilic α-helix mimetics started with bromination of methyl 3-hydroxy-4-aminobenzoate compound 10 followed by displacement with an azide.

An alkylation reaction using methyl N-Ac-4-amino-3-hydroxybenzoate compound 8 and a variety of alkyl halides and a base (like NaH) introduced a functional group corresponding to the i position of the α-helix. The methyl ester compound 16 was hydrolyzed by a base (like LiOH), and the methyl 3-azido-4-amino-5-hydroxybenzoate compound 17 was coupled with BOP. A second alkylation reaction added a functional group to the free 5-hydroxyl group corresponding to the i+3 (or i+4) position. A Staudinger coupling reaction using a suitable carboxylic acid and PPh$_3$ was used to place a functional group at the i+2 position.[84] Besides the Staudinger reaction, other cross-coupling reactions like Suzuki, Stille, Heck, Sonogashira reactions were used to place a functional group at the i+2 position. These steps were repeated to introduce functional groups corresponding to the i+7 and i+5 positions in order to complete the synthesis and to produce amphiphilic α-helix mimetic compounds The incorporated hydrophilic functional groups not only results in a higher potency but also in a higher solubility in water. Corresponding compounds therefore require less organic solvent.

Figures 5A, 5B:
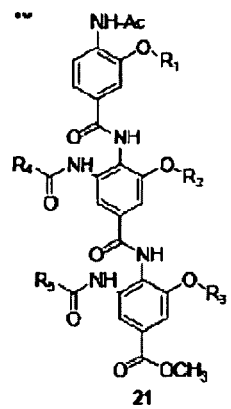
FIGS. 5A and 5B illustrate the structures of various additional peptidomimetic compounds of the present invention that represent two α-helical faces of a peptide.

FIGS. 5A and 5B illustrate the structures of amphiphilic α-helix mimetic compounds of the present invention. The general amphiphilic α-helix mimetic structure is given in FIG. 5A and includes groups R1, R2 and R3 on one face and groups R4 and R5 on another face of the α-helix. FIG. 5B is a table of some of the possible substitutions for groups R1, R2, R3, R4 and R5 of the general amphiphilic α-helix mimetic compound given in FIG. 5A. The resulting amphiphilic α-helix mimetic compounds 21A-21J were analyzed by molecular modeling using MacroModel[80] (version 9, Schrodinger, New York, N.Y.), and the five functional groups in the energy-minimized structure were found to be superimposed well on the corresponding side chain groups of an ideal α-helix.

One example of the chemical synthesis of the present invention is shown herein; however, the skilled artisan will be able to modify the synthetic scheme to create different functional groups and create the same product using different materials. $^1$H- and $^{13}$C-NMR spectra were recorded on a JEOL Model DELTA-270 (270 MHz) spectrometer. Tetramethylsilane (TMS) was used as the internal standard and the chemical shifts are listed in ppm. Data are expressed as follows: chemical shift (δ), multiplicity (s, singlet; d, doublet; dd, doublet of doublet; t, triplet; q, quartet; br s, broad singlet; m, multiplet), coupling constants (Hz). HRMS (FAB) were measured on JEOL HX-110 sector (EB). Silica gel used for column chromatography was Silica Gel Standard Grade (Sorbent Technologies, 230-400 mesh).

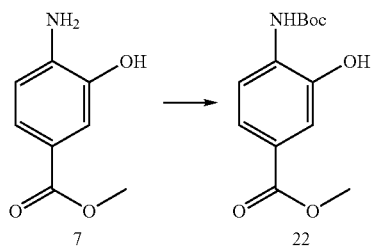 [SMILES: COC(=O)c1ccc(N)c(O)c1 ; COC(=O)c1ccc(NC(=O)OC(C)(C)C)c(O)c1]

A solution of methyl 4-amino-3-hydroxy benzoate compound 7 (5 g, 30.0 mmol) and triethylamine (4.6 ml) in 100 ml CH$_2$Cl$_2$ was added drop-wise to a solution of di-tert-butyl dicarbonate (7.2 g, 32.9 mmol) in 20 ml CH$_2$Cl$_2$ at room temperature. After additional stirring for 12 hours at room temperature, the mixture was poured into water and extracted with CH$_2$Cl$_2$ (3×20 ml). The combined organic layers were washed with brine, dried over Na$_2$SO$_4$, filtered and concentrated under reduced pressure. The residue was purified by column chromatography (n-Hex/Ethyl Acetate (EA)=9/1 to n-Hex/EA=4/1) to give 7.2 g of compound 22 (90%). $^1$H NMR (270 MHz, CDCl$_3$) δ 1.56 (s, 9H), 3.85 (s, 3H), 4.21 (br s, 2H), 6.74 (d, 1H, J=8.42 Hz), 7.73 (dd, 1H, J=8.42, 1.97 Hz), 7.81 (d, 1H, J=1.97 Hz). $^{13}$C NMR (68 MHz, CDCl$_3$) δ 27.7, 51.9, 84.2, 115.4, 119.9, 124.1, 128.7, 137.2, 143.1, 151.3, 166.6. HRMS (FAB): calcd for C$_{13}$H$_{18}$NO$_5$ (M+H)$^+$ 268.1185, found 268.1190.

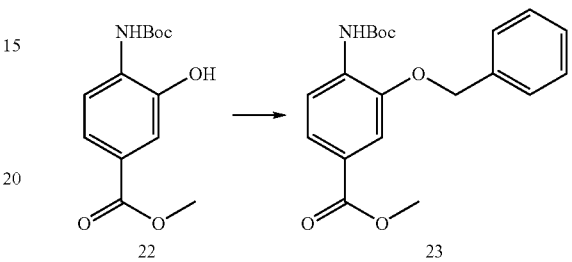

A solution of phenol compound 22 (0.20 g, 0.75 mmol) and NaH (33 mg in 60% oil, 0.82 mmol) in 10 ml dry DMF was stirred for 0.5 hours at room temperature and benzyl bromide (0.15 g, 0.82 mmol) was added slowly. The mixture was stirred for an additional hour and poured into water and extracted with ethyl acetate (3×20 ml). The combined organic layers were washed with brine, dried over Na$_2$SO$_4$, filtered, and concentrated under reduced pressure. The residue was purified by column chromatography (n-Hex/EA=9/1 to n-Hex/EA=4/1) to give 0.22 g of compound 23 (83%). $^1$H NMR (270 MHz, CDCl$_3$) δ 1.52 (s, 9H), 3.89 (s, 3H), 5.16 (s, 2H), 7.27 (br s, 1H), 7.35-7.45 (m, 5H), 7.62 (d, 1H, J=1.73 Hz), 7.69 (d, 1H, J=8.40, 1.73 Hz), 8.20 (d, 1H, J=8.40 Hz). $^{13}$C NMR (68 MHz, CDCl$_3$) δ 28.4, 52.1, 71.1, 81.2, 112.3, 117.1, 123.7, 123.8, 128.0, 128.6, 128.9, 133.1, 136.1, 146.1, 152.4, 166.9. HRMS (FAB): calculated for C$_{20}$H$_{24}$NO$_5$ (M+H)$^+$ 358.1654, found 358.1664.

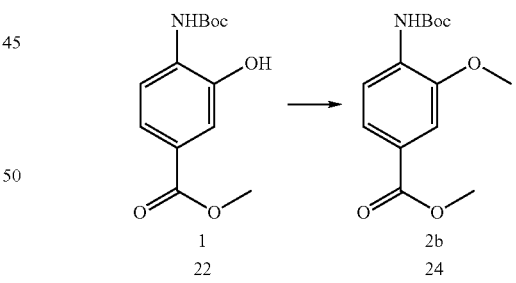

A solution of phenol compound 22 (0.2 g, 0.75 mmol) and NaH (33 mg in 60% oil, 0.82 mmol) in 10 ml dry DMF was stirred for 0.5 hour at room temperature and iodomethane (0.12 g, 0.82 mmol) was added slowly and the mixture was stirred for an additional hour. The mixture was diluted with water and extracted with ethyl acetate (3×20 ml). The combined organic layer was washed with brine, dried over Na$_2$SO$_4$, filtered, and concentrated under reduced pressure. The residue was purified by column chromatography (n-Hex/EA=19/1) to give 0.18 g of compound 24 (86%). $^1$H NMR (270 MHz, CDCl$_3$) δ 1.53 (s, 9H), 3.89 (s, 3H), 3.92 (s, 3H), 7.28 (br s, 1H), 7.51 (d, 1H, J=1.73 Hz), 7.67 (dd, 1H, J=8.42, 1.73 Hz), 8.17 (d, 1H, J=8.42 Hz). $^{13}$C NMR (68 MHz, CDCl$_3$) δ 28.4, 52.0, 55.9, 81.0, 110.7, 116.8, 123.5, 123.7, 132.7, 146.9, 152.5, 167.0. HRMS (FAB): calculated for C$_{14}$H$_{20}$NO$_5$ (M+H)$^+$ 282.1341, found 282.1336.

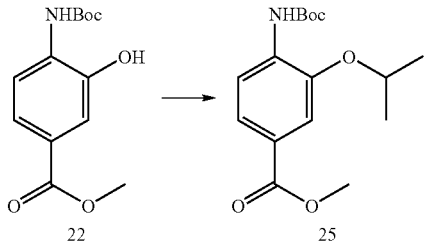 [SMILES: COC(=O)c1ccc(NC(=O)OC(C)(C)C)c(O)c1 ; COC(=O)c1ccc(NC(=O)OC(C)(C)C)c(OC(C)C)c1]

A solution of phenol compound 22 (0.2 g, 0.75 mmol) and NaH (33 mg in 60% oil, 0.82 mmol) were mixed in 10 ml dry DMF and stirred for 0.5 hours at room temperature. Then 2-bromopropane (0.22 g, 1.8 mmol) was added slowly and the mixture was stirred for an additional 24 hours, diluted with water and extracted with ethyl acetate (3×20 ml). The combined organic layer was washed with brine, dried over Na$_2$SO$_4$, filtered, and concentrated under reduced pressure. The residue was purified by column chromatography (n-Hex/EA=19/1) to give 0.18 g of compound 25 (78%). 1H NMR (270 MHz, CDCl$_3$) δ 1.40 (d, 6H, J=6.18 Hz), 1.55 (s, 9H), 3.89 (s, 3H), 4.70 (septet, 1H, J=6.18 Hz), 7.52 (d, 1H, J=1.73 Hz), 7.63 (dd, 1H, J=8.42, 1.73 Hz), 8.17 (d, 1H, J=8.42 Hz). 13C NMR (68 MHz, CDCl$_3$) δ 22.1, 28.4, 52.0, 71.4, 81.0, 113.0, 116.9, 123.2, 123.6, 133.6, 145.0, 152.4, 167.0. HRMS (FAB): calculated for C16H24NO5 (M+H)+ 310.1654, found 310.1668.

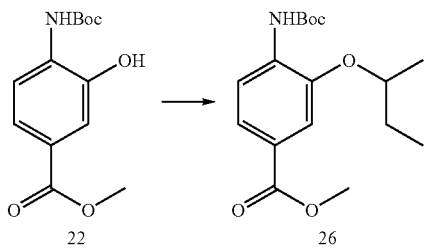 [SMILES: COC(=O)c1ccc(NC(=O)OC(C)(C)C)c(O)c1 ; CCC(C)Oc1cc(C(=O)OC)ccc1NC(=O)OC(C)(C)C]

A solution of phenol compound 22 (0.2 g, 0.75 mmol) and NaH (33 mg in 60% oil, 0.82 mmol) was stirred in 10 ml dry DMF for 0.5 hour at room temperature and then 2-bromobutane (0.25 g, 1.8 mmol) was added slowly. The mixture was stirred for an additional 24 hours, diluted with water, extracted with ethyl acetate (3×20 ml), the combined organic layer was washed with brine, dried over Na$_2$SO$_4$, filtered, and concentrated under reduced pressure. The residue was purified by column chromatography (n-Hex/EA=19/1) to give 0.18 g of compound 26 (73%). $^1$H NMR (270 MHz, CDCl$_3$) δ 1.00 (t, 3H, J=7.40), 1.34 (d, 3H, J=6.18 Hz), 1.54 (s, 9H), 1.62-1.90 (m, 2H), 3.89 (s, 3H), 4.46 (sextet, 1H, J=6.18 Hz), 7.51 (d, 1H, J=1.73 Hz), 7.64 (dd, 1H, J=8.40, 1.73 Hz), 8.17 (d, 1H, J=8.40 Hz). $^{13}$C NMR (68 MHz, CDCl$_3$) δ 9.9, 19.3, 28.4, 29.2, 52.0, 76.5, 81.0, 113.1, 117.0, 123.2, 123.6, 133.6, 145.2, 152.5, 167.0. HRMS (FAB): calculated for C$_{17}$H$_{26}$NO$_5$ (M+H)$^+$ 324.1811, found 324.1810.

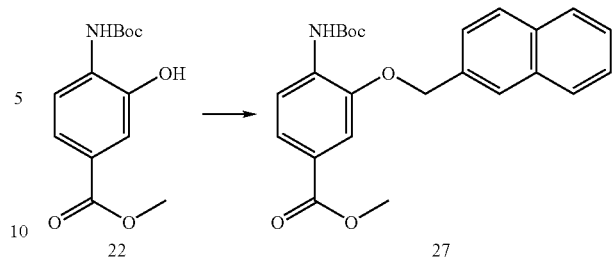

A solution of phenol compound 22 (0.2 g, 0.75 mmol) and NaH (33 mg in 60% oil, 0.82 mmol) was stirred in 10 ml dry DMF for 0.5 hours at room temperature and 2-bromomethylnaphtalene (0.18 g, 0.82 mmol) was added slowly. The mixture was stirred for an additional hour. The mixture was diluted with water, extracted with ethyl acetate (3×20 ml), and the combined organic layer was washed with brine, dried over Na$_2$SO$_4$, filtered and concentrated under reduced pressure. The residue was purified by column chromatography (n-Hex/EA=10/1 to n-Hex/EA=4/1) to give 0.25 g of compound 27 (82%). $^1$H NMR (270 MHz, CDCl$_3$) δ 1.50 (s, 9H), 3.87 (s, 3H), 5.30 (s, 2H), 7.30 (br s, 1H), 7.48-7.57 (m, 3H), 7.65-7.73 (m, 2H), 7.82-7.94 (m, 4H), 8.22 (d, 1H, J=8.40 Hz). $^{13}$C NMR (68 MHz, CDCl$_3$) δ 28.4, 52.1, 71.3, 81.2, 112.4, 117.1, 123.8, 123.9, 125.5, 126.5, 126.6, 127.1, 127.9, 128.1, 128.8, 133.1, 133.3, 133.5, 146.2, 152.4, 166.9. HRMS (FAB): calculated for C$_{24}$H$_{26}$NO$_5$ (M+H)$^+$ 408.1811, found 408.1833.

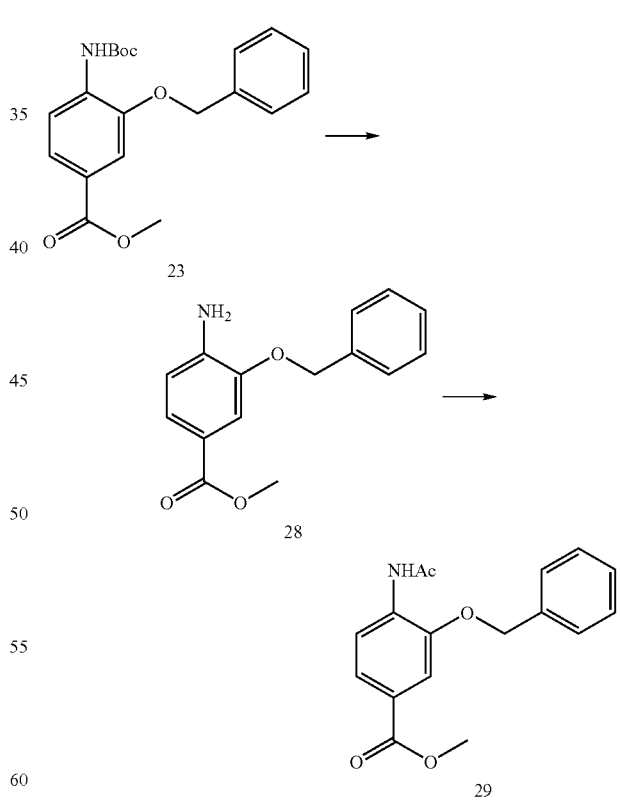

To a solution of compound 23 (2 g, 5.60 mmol) in 16 ml CH$_2$Cl$_2$, 4 ml trifluoroacetic acid was added in an ice-water bath. The reaction solution was stirred at room temperature for 2 hours and the excess trifluoroacetic acid and CH$_2$Cl$_2$ were removed under reduced pressure. The residue was dissolved in CH₂Cl₂, washed with saturated NaHCO₃ and brine and dried over Na₂SO₄. The organic layer was concentrated under reduced pressure to give the corresponding aniline, which was used in the next step without purification. A solution of aniline and DMAP (68 mg, 0.56 mmol) in acetic anhydride was stirred at room temperature for 12 hours. The reaction mixture was poured into water and extracted with CH₂Cl₂. The organic layer was washed with 1N HCl, water, and saturated NaHCO₃ solution, dried and concentrated to give compounds 28 and 29. The mixture was purified by column chromatography (n-Hex/EA=4/1 to n-Hex/EA=2/1) to give 1.62 g of compound 29 (97%). ¹H NMR (270 MHz, CDCl₃) δ 2.17 (s, 3H), 3.89 (s, 3H), 5.16 (s, 2H), 7.36-7.46 (m, 5H), 7.65 (d, 1H, J=1.73 Hz), 7.69 (dd, 1H, J=8.40, 1.73 Hz), 7.92 (br s, 1H), 8.48 (d, 1H, J=8.67 Hz). ¹³C NMR (68 MHz, CDCl₃) δ 25.1, 52.2, 71.3, 112.4, 118.9, 123.8, 125.0, 128.0, 128.7, 128.9, 132.4, 135.9, 146.4, 166.7, 168.5. HRMS (FAB): calculated for C₁₇H₁₈NO₄ (M+H)⁺ 300.1236, found 300.1235.

Compound 29 (1.62 g, 5.68 mmol) was dissolved in 1N NaOH (10 ml)/MeOH (20 ml)/THF (40 ml) and stirred at 60° C. for 2 hours. Methanol and THF were carefully concentrated and the mixture was acidified with 1N HCl, and the suspension was extracted with ethyl acetate, dried over Na₂SO₄ and evaporated under reduced pressure to give the corresponding acid, which was used in the next step without purification. The solution of acid, DMF (cat.) and SOCl₂ (2.7 g, 22.7 mmol) in 20 ml THF was heated at 60° C. for 2 hours. After the reaction mixture was cooled, the reaction mixture was concentrated under reduced pressure. The residue was dissolved in CH₂Cl₂ and cooled at 0° C. To this acid chloride DIPEA (5.14 g, 39.8 mmol) and methyl 4-amino-3-hydroxybenzoate compound 7 (1.42 g, 8.51 mmol) were added and stirred at room temperature for 2 hours. The reaction mixture was concentrated under reduced pressure and the residue was purified by column chromatography (n-Hex/EA=2/1 to n-Hex/EA=1/1) to give 2.02 g of compound 30 (82% in three steps). ¹H NMR (270 MHz, CDCl₃) δ 2.20 (s, 3H), 3.85 (s, 3H), 4.11 (br s, 2H), 5.20 (s, 2H), 6.80 (d, 1H, J=8.91 Hz), 7.36-7.47 (m, 5H), 7.74-7.82 (m, 3H), 7.88 (dd, 1H, J=8.42, 1.73 Hz), 7.99 (br s, 1H), 8.56 (d, 1H, J=8.42 Hz). ¹³C NMR (68 MHz, CDCl₃) δ 25.2, 51.9, 71.4, 112.9, 115.6, 119.0, 120.3, 123.5, 124.59, 124.63, 128.0, 128.8, 128.9, 129.0, 133.4, 135.7, 136.9, 143.3, 146.5, 164.1, 166.6, 168.7. HRMS (FAB): calculated for C₂₄H₂₃N₂O₆ (M+H)⁺ 435.1556, found 435.1568.

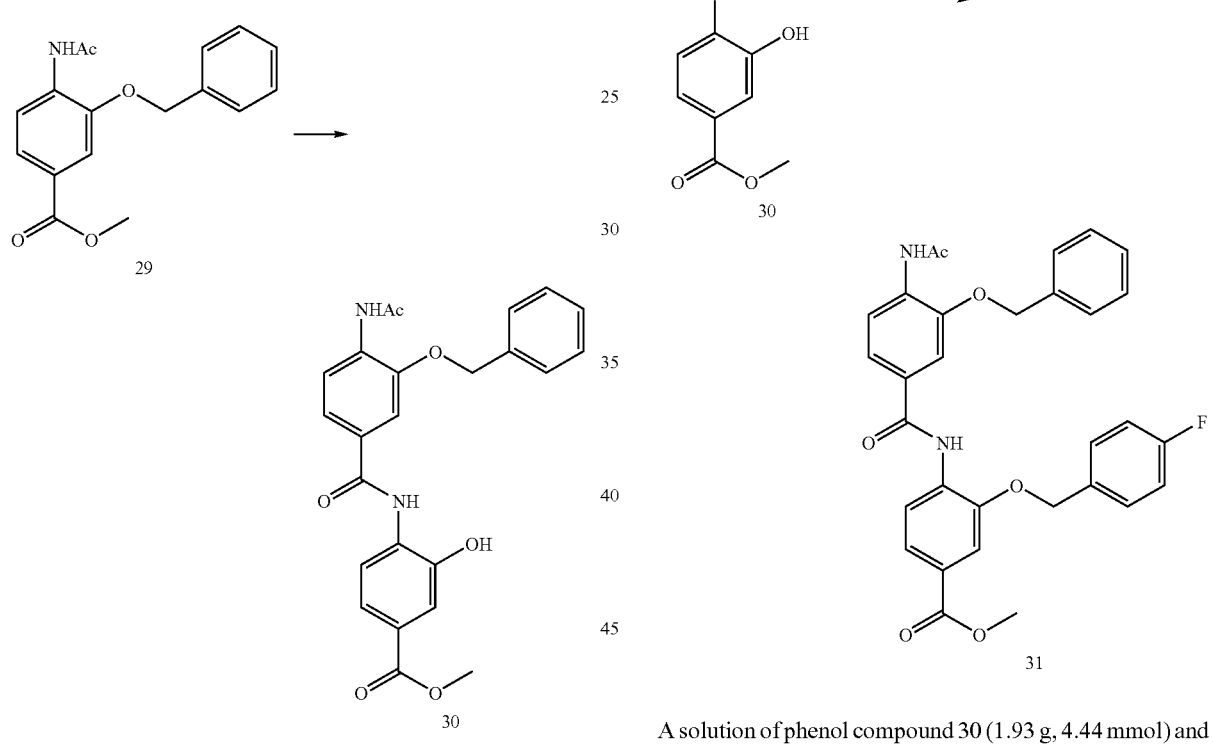

A solution of phenol compound 30 (1.93 g, 4.44 mmol) and NaH (0.20 g in 60% oil, 4.88 mmol) in 50 ml dry DMF was stirred for 0.5 hour at room temperature and then 4-fluorobenzyl bromide (1.01 g, 5.33 mmol) was added slowly. The mixture was stirred for an additional 2 hours, diluted with water, and extracted with ethyl acetate (3×40 ml). The combined organic layer was washed with brine, dried (Na₂SO₄) and concentrated under reduced pressure. The residue was purified by column chromatography (n-Hex/EA=4/1 to n-Hex/EA=2/1) to give 1.86 g of compound 31 (77%). ¹H NMR (270 MHz, CDCl₃) δ 2.18 (s, 3H), 3.91 (s, 3H), 5.11 (s, 2H), 5.17 (s, 2H), 7.09 (t, 2H, J=8.42 Hz), 7.27 (dd, 1H, J=8.64, 1.73 Hz), 7.35-7.48 (m, 7H), 7.57 (d, 1H, J=1.73 Hz), 7.67 (d, 1H, J=1.73 Hz), 7.75 (dd, 1H, J=8.42, 1.73 Hz), 8.46 (d, 1H, J=8.42 Hz), 8.62 (d, 1H, J=8.64 Hz), 8.72 (br s, 1H). ¹³C NMR (68 MHz, CDCl₃) δ 25.1, 52.2, 70.8, 71.3, 111.0, 112.4, 116.0 (d, J=21.3 Hz), 118.8, 119.1, 119.6, 124.1, 125.1, 128.0, 128.8, 129.0, 129.4, 129.8 (d, J=8.3 Hz), 131.7, 132.5, 135.7, 146.7, 147.1, 162.9 (d, J=248.1 Hz), 164.5, 166.7, 168.6. HRMS (FAB): calculated for $C_{31}H_{28}FN_2O_6$ (M+H)$^+$ 543.1931, found 543.1942.

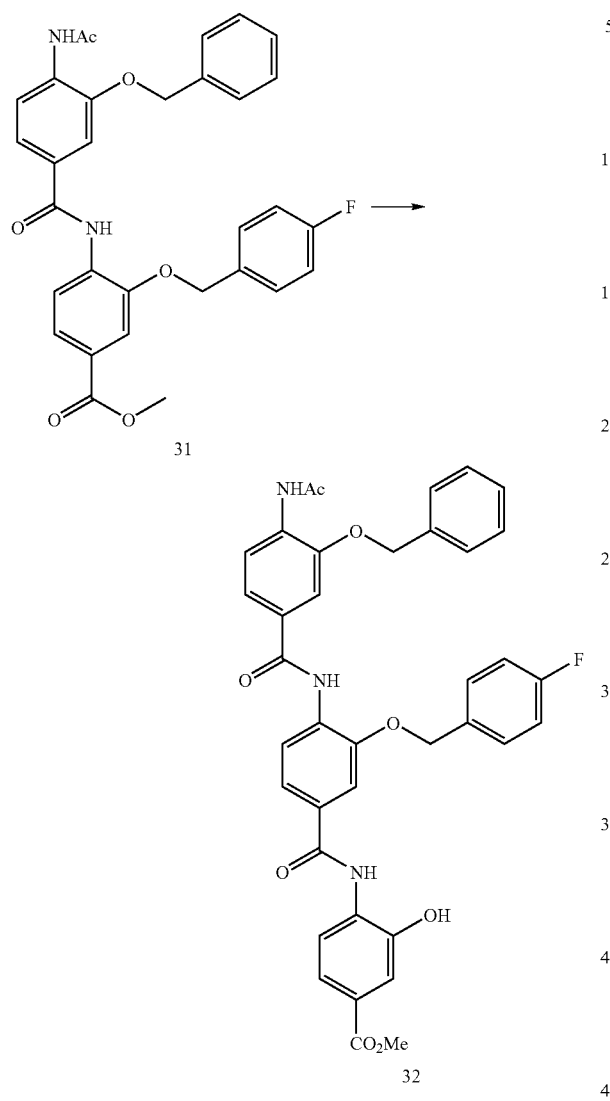

Dimer compound 31 (1.86 g, 3.43 mmol) was dissolved in 1N NaOH (10 ml)/MeOH (20 ml)/THF (40 ml) and heated at 60° C. for 2 hours. Methanol and THF were carefully concentrated and the mixture was acidified with 1N HCl, and the suspension was extracted with ethyl acetate, dried over $Na_2SO_4$ and evaporated under reduced pressure to give the corresponding acid, which was used in the next step without purification. The solution of acid, BOP (1.92 g, 4.11 mmol) and DIPEA (1.11 g, 8.57 mmol) in $CH_2Cl_2$ was stirred at 0° C. for 0.5 hour. Methyl 4-amino-3-hydroxybenzoate compound 7 (0.57 g, 2.86 mmol) was added and stirred at room temperature for 2 hours. The mixture was poured into water and extracted with $CH_2Cl_2$ (3×40 ml), and the combined organic layer was washed with brine, dried over $Na_2SO_4$, filtered, and concentrated under reduced pressure. The residue was purified by column chromatography (dichloromethane/ethyl ether=19/1) to give 1.72 g of compound 32 (74% in two steps). $^1$H NMR (270 MHz, CDCl$_3$) δ 2.19 (s, 3H), 3.85 (s, 3H), 4.15 (br s, 2H), 5.19 (s, 2H), 5.20 (s, 2H), 6.82 (d, 2H, J=8.88 Hz), 7.10 (t, 2H, J=8.65 Hz), 7.30 (dd, 1H, J=8.40, 1.73 Hz), 7.34-7.50 (m, 7H), 7.59 (d, 1H, J=1.73 Hz), 7.75-7.81 (m, 3H), 7.88 (m, 1H), 8.48 (d, 1H, J=8.40 Hz), 8.70 (d, 1H, J=8.40 Hz), 8.79 (br s, 1H). $^{13}$C NMR (68 MHz, CDCl$_3$) δ 25.1, 51.9, 70.9, 71.3, 111.1, 112.9, 115.6, 116.1 (d, J=21.8 Hz), 119.0, 119.1, 119.6, 120.4, 123.6, 124.7, 124.8, 128.0, 128.8, 129.0, 129.3, 129.8 (d, J=8.3 Hz), 131.5 (d, J=3.6 Hz), 131.8, 133.5, 135.7, 136.9, 143.2, 146.9, 147.1, 162.7 (d, J=216.4 Hz), 164.1, 164.5, 166.6, 168.6. HRMS (FAB): calculated for $C_{38}H_{33}FN_3O_8$ (M+H)$^+$ 678.2252, found 678.2262.

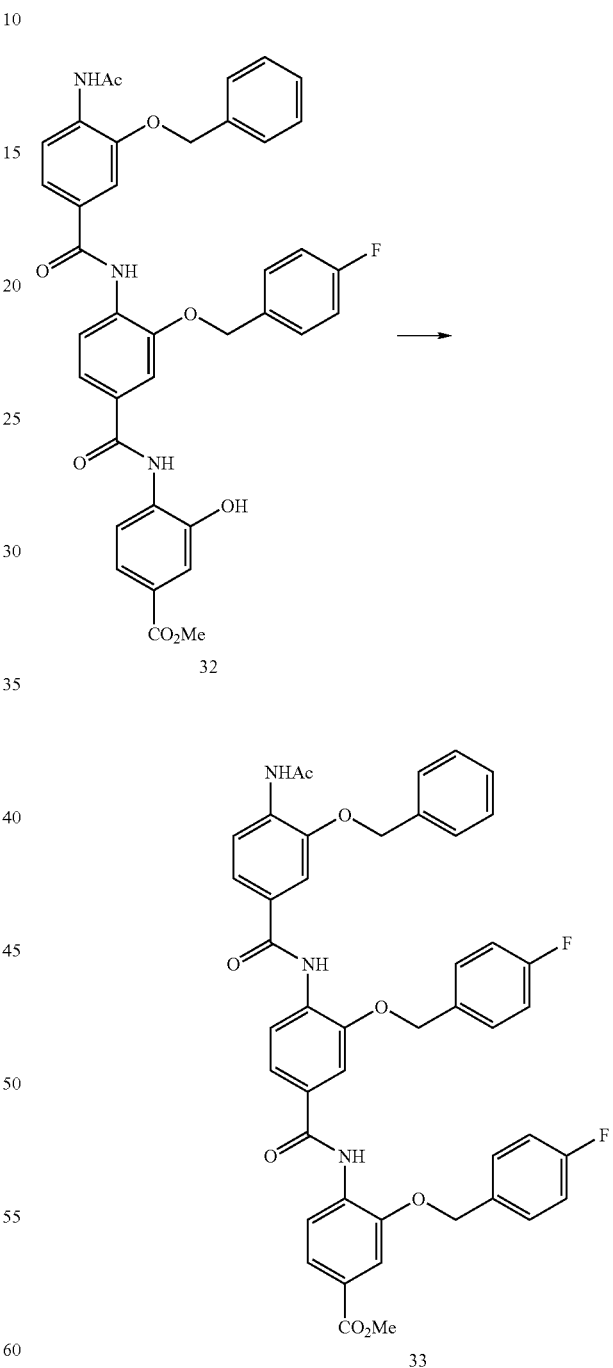

A solution of phenol compound 32 (1.72 g, 2.54 mmol) and NaH (0.11 g in 60% oil, 2.79 mol) in 50 ml dry DMF was stirred for 0.5 hours at room temperature and then 4-fluorobenzyl bromide (3.05 mmol) was added slowly. The mixture was stirred for an additional 2 hours. The mixture was diluted with water and extracted into ethyl acetate (3×40 ml). The combined organic layer was washed with brine, dried (Na2SO4) and concentrated under reduced pressure. The residue was purified by column chromatography (dichloromethane/ethyl ether=19/1) to give 1.20 g of compound 33 (61%). 1H NMR (270 MHz, DMSO-d6) δ 2.15 (s, 3H), 3.86 (s, 3H), 5.23 (s, 2H), 5.27 (s, 2H), 5.29 (s, 2H), 7.12-7.74 (m, 19H), 8.03-8.15 (m, 3H), 9.34 (br s, 1H), 9.51 (br s, 1H), 9.59 (br s, 1H) 13C NMR (68 MHz, CDCl3) δ 24.6, 52.7, 70.1, 70.6, 112.4, 112.5, 113.6, 115.8 (d, J=21.8 Hz), 120.8, 120.9, 121.8, 123.0, 123.1, 123.4, 126.5, 128.0, 128.5, 129.0, 130.0, 130.3 (d, J=7.8 Hz), 131.2, 131.5, 132.0, 132.7, 133.38, 133.42, 133.48, 137.2, 148.6, 149.9, 150.1, 162.4 (d, J=243.4 Hz), 164.9, 166.4, 169.5. HRMS (FAB): calculated for C45H38F2N3O8 (M+H)+ 786.2627, found 786.2598.

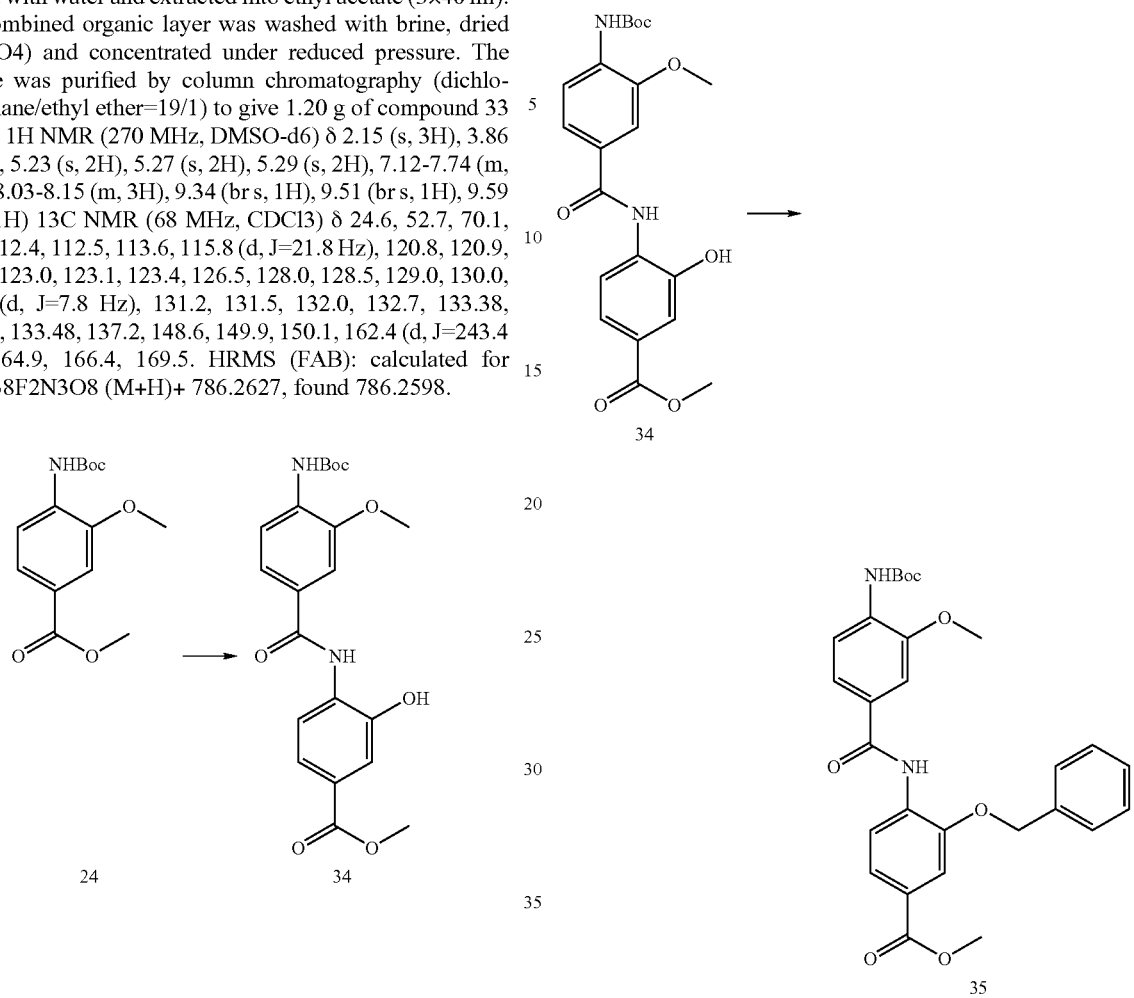

Compound 24 (2 g, 7.11 mmol) was dissolved in 1N NaOH (10 ml)/MeOH (20 ml)/THF (40 ml) and heated at 60° C. for 2 hours. Methanol and THF were carefully concentrated and the mixture was acidified with 1N HCl. The suspension was extracted with ethyl acetate, dried over Na2SO4 and evaporated under reduced pressure to give the corresponding acid, which was used in the next step without purification. The solution of acid, DMF (cat.) and SOCl2 (3.38 g, 28.4 mmol) in 20 ml THF was heated at 60° C. for 2 hours. The reaction mixture was cooled and concentrated under reduced pressure. The residue was dissolved in CH2Cl2 and cooled at 0° C. To this acid chloride DIPEA (9.19 g, 71.1 mmol) and methyl 4-amino-3-hydroxybenzoate compound 7 (1.42 g, 8.53 mmol) were added and stirred at room temperature for 2 hours. The reaction mixture was concentrated under reduced pressure and purified by column chromatography (n-Hex/EA=4/1 to n-Hex/EA=2/1) to give 2.28 g of compound 34(77% in three steps). 1H NMR (270 MHz, CDCl3) δ 1.55 (s, 3H), 3.84 (s, 3H), 3.95 (s, 3H), 4.16 (br s, 2H), 6.80 (d, 1H, J=8.88 Hz), 7.37 (br s, 1H), 7.63 (d, 1H, J=1.73 Hz), 7.74-7.82 (m, 2H), 7.85 (dd, 1H, J=8.42, 1.73 Hz), 8.56 (d, 1H, J=8.67 Hz). 13C NMR (68 MHz, CDCl3) δ 28.4, 51.8, 56.1, 81.3, 111.2, 115.6, 116.9, 120.2, 122.1, 124.4, 124.7, 128.8, 133.8, 137.0, 143.4, 147.1, 152.3, 164.4, 166.6. HRMS (FAB): calculated for C21H25N2O7 (M+H)+ 417.1662, found 417.1645.

A solution of compound 34 (2.28 g, 5.48 mmol) and NaH (0.24 g in 60% oil, 6.02 mol) in 50 ml dry DMF was stirred for 0.5 hour at room temperature and benzyl bromide (1.13 g, 6.57 mmol) was added slowly. The mixture was stirred for an additional 2 hours, diluted with water and extracted with ethyl acetate (3×40 ml). The combined organic layer was washed with brine, dried (Na2SO4) and concentrated under reduced pressure. The residue was purified by column chromatography (n-Hex/EA=4/1 to n-Hex/EA=2/1) to give 2.21 g of compound 35 (80%). 1H NMR (270 MHz, CDCl3) δ 1.54 (s, 3H), 3.84 (s, 3H), 3.92 (s, 3H), 5.20 (s, 2H), 7.24-7.52 (m, 8H), 7.71 (d, 1H, J=1.73 Hz), 7.77 (dd, 1H, J=8.42, 1.73 Hz), 8.13 (d, 1H, J=8.42 Hz), 8.65 (d, 1H, J=8.67 Hz), 8.78 (br s, 1H). 13C NMR (68 MHz, CDCl3) δ 28.4, 52.2, 55.9, 71.5, 81.1, 109.3, 112.3, 117.0, 118.6, 119.6, 124.0, 125.0, 128.0, 128.1, 128.8, 129.0, 132.0, 132.7, 135.9, 146.9, 147.5, 152.4, 164.7, 166.8. HRMS (FAB): calculated for C28H31N2O7 (M+H)+ 507.2131, found 507.2133.

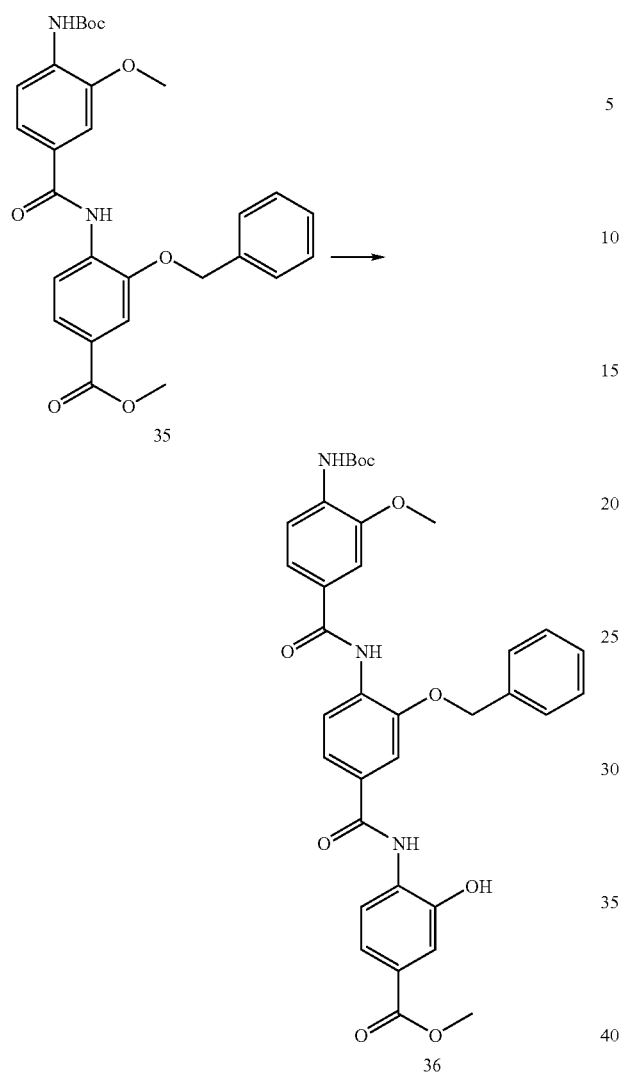

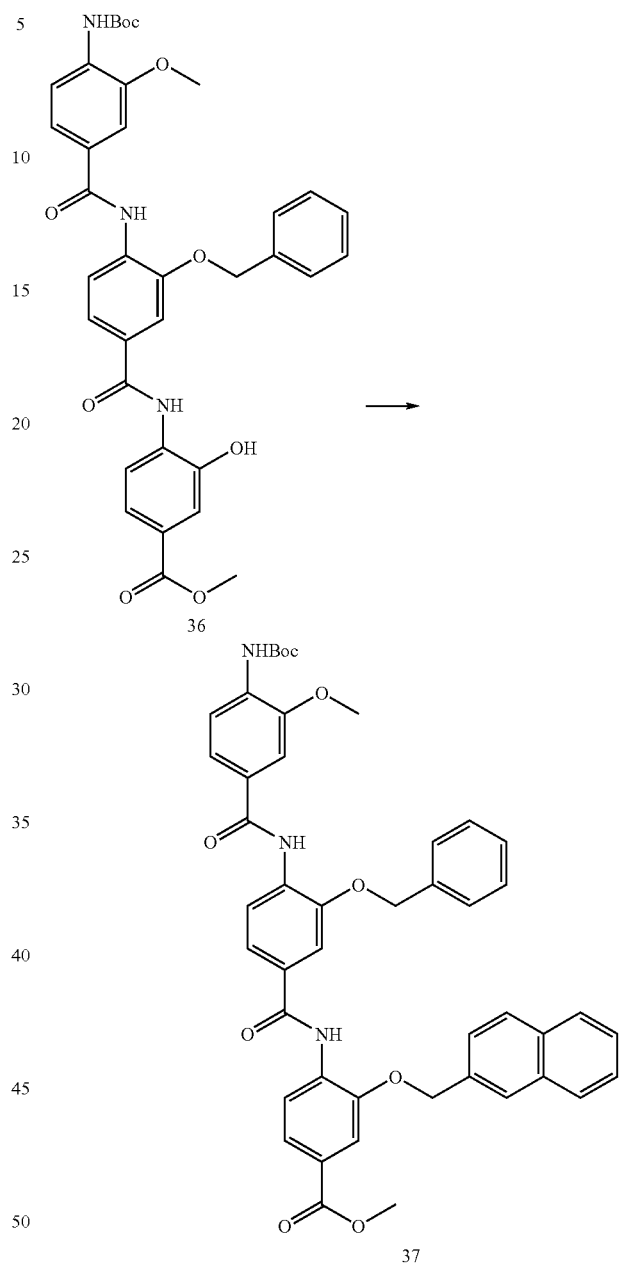

Compound 35 (2.21 g, 4.49 mmol) was dissolved in 1N NaOH (10 ml)/MeOH (20 ml)/THF (40 ml) and heated at 60° C. for 2 hours. Methanol and THF were carefully concentrated and the mixture was acidified with 1N HCl. The suspension was extracted with ethyl acetate, dried over Na2SO4 and evaporated under reduced pressure to give the corresponding acid, which was used in the next step without purification. The solution of acid, DMF (cat.) and SOCl2 (2.14 g, 17.9 mmol) in 20 ml THF was refluxed for 2 hours. The reaction mixture was cooled and concentrated under reduced pressure. The residue was dissolved in CH2Cl2 and cooled at 0° C. To this acid chloride, DIPEA (5.80 g, 44.9 mmol) and methyl 4-amino-3-hydroxybenzoate 5 (0.90 g, 5.38 mmol) were added and stirred at room temperature for 2 hours. The reaction mixture was concentrated under reduced pressure and purified by column chromatography (n-Hex/EA=9/1 to n-Hex/EA=2/1) to give 2.19 g of compound 36 (76% in three steps). 1H NMR (270 MHz, CDCl3) δ 1.55 (s, 3H), 3.86 (s, 6H), 5.24 (s, 3H), 6.82 (d, 1H, J=6.87 Hz), 7.78-7.86 (m, 3H), 7.69 (dd, 1H, J=8.67, 1.73 Hz), 8.15 (d, 1H, J=8.42 Hz), 8.73 (d, 1H, J=8.64 Hz), 8.85 (br s, 1H). 13C NMR (68 MHz, CDCl3) δ 28.4, 51.9, 55.9, 71.6, 81.2, 109.3, 112.8, 115.6, 117.0, 118.8, 119.6, 120.2, 123.4, 124.7, 124.8, 127.9, 128.0, 128.9, 129.0, 132.2, 133.6, 135.7, 136.9, 143.4, 147.0, 147.5, 152.4, 164.2, 164.7, 166.6. HRMS (FAB): calculated for C35H36N3O9 (M+H)+ 642.2452, found 642.2432.

A solution of trimer compound 36 (2.19 g, 3.41 mmol) and NaH (0.15 g in 60% oil, 3.75 mmol) in 50 ml dry DMF was stirred for 0.5 hour at room temperature. 2-bromomethyl naphthalene (0.91 g, 4.10 mmol) was added slowly to the solution. The solution was stirred for an additional 2 hours, diluted with water and extracted with ethyl acetate (3×40 ml). The combined organic layer was washed with brine, dried (Na$_2$SO$_4$) and concentrated under reduced pressure. The residue was purified by column chromatography (n-Hex/EA=4/1 to n-Hex/EA=1/1) to give 2.29 g of compound 37 (86%). $^1$H NMR (270 MHz, CDCl$_3$) δ 1.55 (s, 3H), 3.82 (s, 3H), 3.91 (s, 3H), 5.03 (s, 2H), 5.37 (s, 2H), 7.22-7.60 (m, 13H), 7.74-7.94 (m, 6H), 8.11 (d, 1H, J=8.40 Hz), 8.58 (d, 1H, J=8.40 Hz), 8.66 (d, 1H, J=8.40 Hz), 8.70 (br s, 1H), 8.84 (br s, 1H). $^{13}$C NMR (68 MHz, CDCl$_3$) δ 28.5, 52.4, 56.0, 71.5, 71.9, 81.3, 109.3, 110.8, 112.6, 117.1, 118.9, 119.0, 119.8, 120.2, 124.2, 125.3, 126.8, 126.9, 127.2, 128.1, 128.2, 129.0, 129.1, 129.4, 132.1, 132.2, 132.8, 133.4, 133.5, 135.9, 147.1, 147.5, 147.6, 152.6, 164.6, 164.8, 166.9. HRMS (FAB): calculated for C46H44N3O9 (M+H)+ 782.3078, found 782.3065.

The synthesis of benzamides includes an alkylation reaction to place a functional group corresponding to an amino acid in a helix. The reaction is given below:

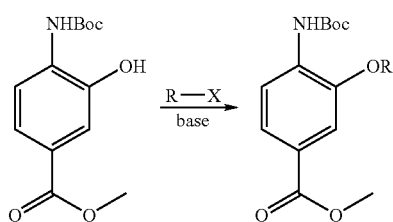

The hydroxyl group in methyl 4-(t-butoxycarbonylamino)-3-hydroxybenzoate was reacted with a series of alkyl halides in the presence of bases as described in Table 1.

| Product | R—X | Reaction Condition | Yield (%)$^a$ |
|---------|-----|--------------------|---------------|
| 2a | benzyl-Br | K$_2$CO$_3$ (1.2 eq), acetone, reflux, 24 h | 33 |
| 2a | benzyl-Br | NaH (1.1 eq), DMF, rt, 1.5 h | 83 |
| 2a | benzyl-Br | NaH (1.1 eq), THF, reflux, 2.5 h | 53 |
| 2a | benzyl-Br | NaOMe (1.2 eq), DMF, rt, 1.5 h | 73 |
| 2a | benzyl-Br | NaOMe (1.2 eq), THF, reflux, 2.5 h | 72 |
| 2a | benzyl-Br | DBU (5 eq), DMF, rt, 12 h | 19 |
| 2b | CH$_3$I | NaH (1.1 eq), DMF, rt, 1.5 h | 86 |
| 2c | isopropyl-Br | NaH (1.1 eq), DMF, rt, 24 h | 78 |
| 2d | sec-butyl-Br | NaH (1.1 eq), DMF, rt, 24 h | 73 |
| 2e | 2-naphthylmethyl-Br | NaH (1.1 eq), DMF, rt, 1.5 h | 83 |

Several bases and solvents were screened to optimize the reaction condition and the use of NaH in DMF at room temperature resulted in high yield. Sodium methoxide also provided good yield and less byproducts than NaH, whereas K$_2$CO$_3$ and a hindered organic base, 1,8-diazabicyclo[5.4.0]undec-7-ene (DBU) were found to be inefficient. As a solvent, DMF appears to be more effective than THF since the benzylation in THF required refluxing even with the most efficient base found (NaH), whereas DMF provided higher yield at much lower ambient temperature. The alkylation reaction was carried out with various alkyl halides under the optimized reaction condition, resulting in the desired products in high yield (70-80%). Methyl and benzyl halides mimicking Ala and Phe, respectively, gave slightly better yields compared to aliphatic alkyl halides, such as 2-bromopropane and 2-bromobutane representing Val and Ile, respectively. 2-Naphthylmethyl group was introduced in an attempt to replace the indole side chain of Trp. The coupling reaction was per-formed using an unalkylated hydroxybenzoate instead of the alkylated. Using SOCl₂ or BOP as a coupling reagent, the alkoxybenzamide was synthesized in high yield (70-80%), and a subsequent alkylation produced the desired dialkoxybenzamide which possesses two functional groups in a helix.

Figure 6:
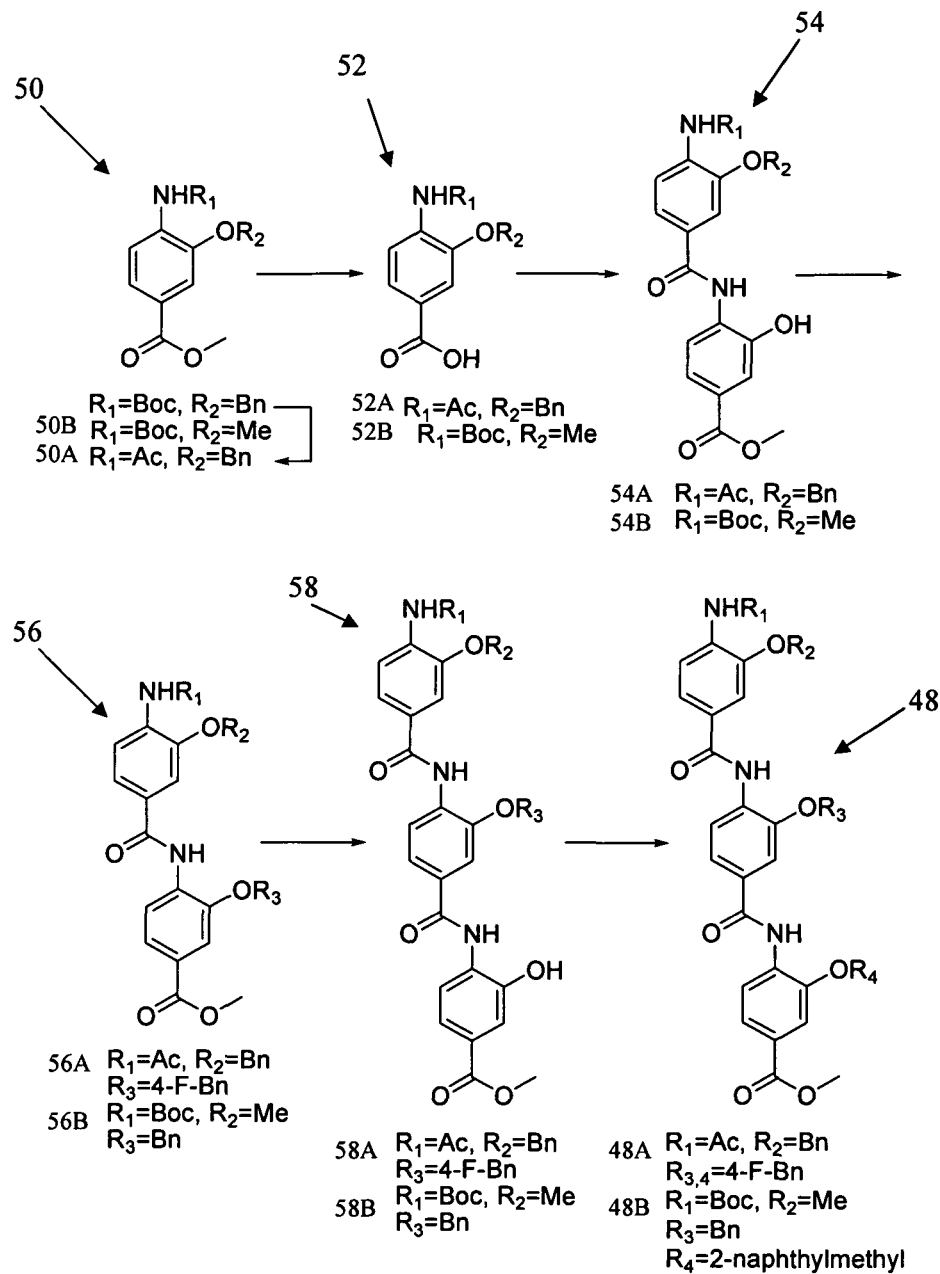
FIG. 6 is a scheme for the synthesis of additional α-helix peptidomimetic compounds.

FIG. 6 is a scheme for the synthesis of two tris-benzamides 48A and 48B, where tris-benzamides 48A includes a R1 that is an Acetyl (Ac) group, R2 is a Benzyl (Bn) group and R3 and R4 are 4-fluorobenzyl groups and tris-benzamides 48B includes a R1 is a t-butoxycarbonyl (Boc) group, R2 is a Methyl (Me) group and R3 is a Benzyl (Bn) group and R4 is a 2-naphthylmethyl.

After the alkylation of the hydroxybenzoate compound 50, the methyl ester was hydrolyzed using NaOH, and methyl 4-amino-3-hydroxybenzoate was coupled to the benzoic acid (compound 52A where R1 is an Acetyl (Ac) group and R2 as a Benzyl (Bn) group and compound 52B where R1 as a t-butyloxycarbonyl (Boc) group and R as a Methyl (Me) group) using SOCl₂, resulting in a bis-benzamide containing one alkyl group (compound 54A where R1 as an Acetyl (Ac) group and R2 as a Benzyl (Bn) group and compound 54B where R1 as a t-butyloxycarbonyl (Boc) group and R2 as a Methyl (Me) group) corresponding to the i position of a helix. The alkylation and coupling reactions were repeated twice to place two other functional groups corresponding to the i+4 (or i+3) and i+7 positions as seen in compound 56A where R1 is an Acetyl (Ac) group, R2 is a Benzyl (Bn) group and R3 is a 4-fluorobenzyl group; compound 56B where R1 is a t-butyloxycarbonyl (Boc) group, R2 is a Methyl (Me) group and R3 is a Benzyl (Bn) group; compound 58A where R1 is an Acetyl (Ac) group, R2 is a Benzyl (Bn) group and R3 is a 4-fluorobenzyl group; and compound 58B where R1 is a t-butoxycarbonyl (Boc) group, R2 is a Methyl (Me) group and R3 is a Benzyl (Bn) group.

Figures 7A, 7B, 7C:
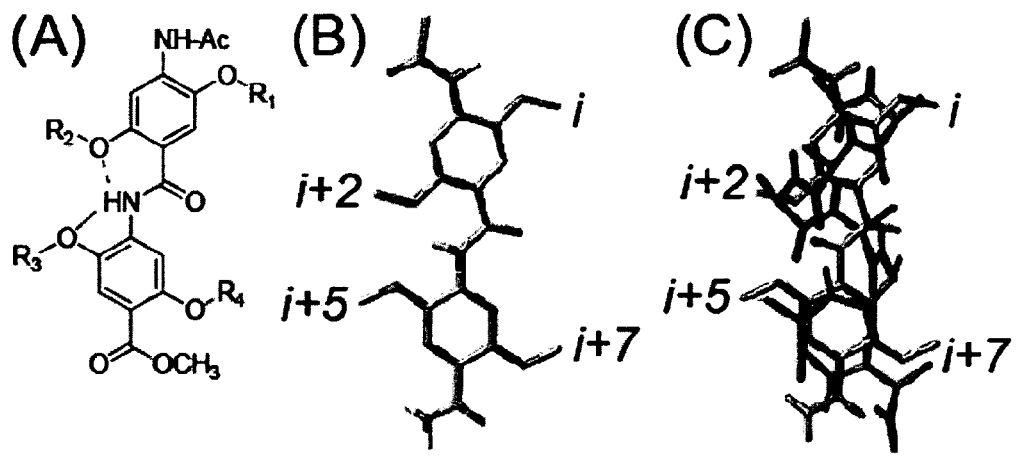
FIG. 7A is an image of a bis-benzamide structure that is used to generate α-helix peptidomimetic compounds of the present invention.
FIGS. 7B and 7C are images of the energy-minimized structure of an α-helix peptidomimetic compound.

The present invention also provides an amphiphilic α-helix mimetic using a different template. The template used to mimic an amphiphilic α-helix, is a bis-benzamide structure that constitutes two 4-amino-2,5-dihydroxybenzoic acid moieties as seen in FIGS. 7A and 7B. Analogous to the building block of the original amphiphilic α-helix mimetic (3,4-diamino-5-hydroxybenzoic acid), the building block of the alternative scaffold (4-amino-2,5-dihydroxybenzoic acid) also has two hydroxyl groups at the 2- and 5-positions to present two functional groups found on opposite faces of an α-helix. However, the structure of the alternative scaffold is quite different compared to the original one. Its structure was again analyzed by molecular modeling using MacroModel (a Monte Carlo conformational search).

FIG. 7C is an image of the energy minimized structure of the lowest energy conformation was analyzed by molecular modeling using MacroModel. The energy minimized structure of the lowest energy conformation showed significantly enhanced rigidity in the structure, resulting from two hydrogen bonds made by the benzamide proton and two nearby alkoxy groups (R2 and R3), one from the 2-position in the upper benzene ring and the other from the 5-position in the lower benzene ring. These hydrogen bonds tightly secure the relative orientation of two benzene rings, and direct two alkyl groups (R2 and R3) at the 2-position in the upper ring and the 5-position in the lower ring on the same side of the structure. This results in the remaining two alkyl groups (R1 and R4) at the 5-position in the upper ring and the 2-position in the lower ring being on the same side, opposite to the former two groups (R2 and R3). Superimposition of this alternative amphiphilic α-helix mimetic over an α-helix reveals that 4 alkyl groups (R1-4) in the mimetic represent 4 side chains of the helix extremely well as seen in FIG. 7C. The hydrogen bonds increase the distance between two alkyl groups (R1 and R4) at the 5-position in the upper ring and the 2-position in the lower ring, well representing the i and i+7 positions. On the other hand, the two alkyl groups (R2 and R3) being in close proximity due to the hydrogen bonds overlay well to the side chain groups at the i+2 and i+5 positions on the opposite face of a helix.

Figure 8:
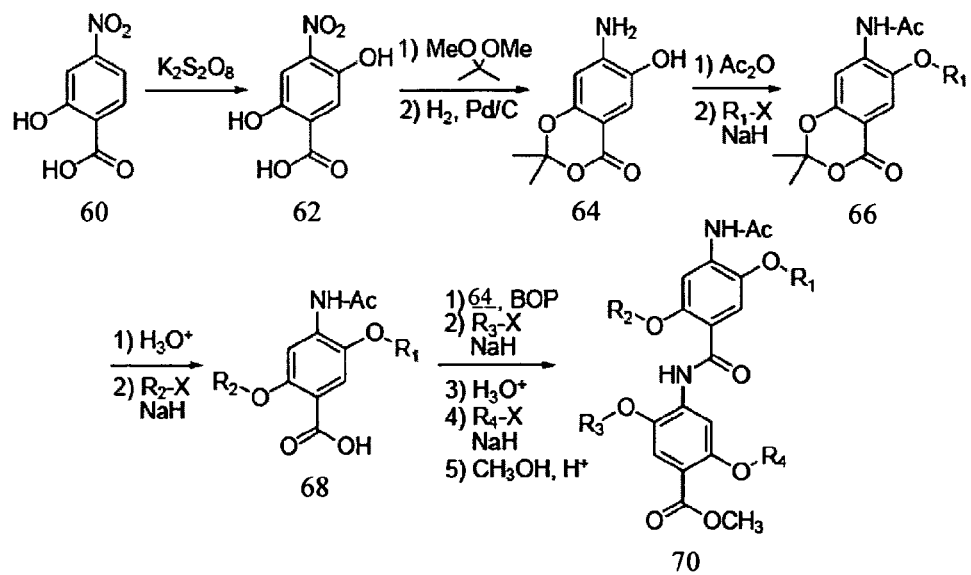
FIG. 8 is a scheme for the synthesis of another α-helix peptidomimetic compound of the present invention.

FIG. 8 is a scheme for the synthesis of the alternative amphiphilic α-helix mimetics of the present invention. The 4-aminosalicylic acid compound 60 was protected as N-Boc methyl ester compound 62, which was oxidized with persulfate. The Boyland-Sim oxidation reaction produced methyl N-Boc-4-amino-2,5-dihydroxybenzoate compound 62, and the N-Boc protecting group was removed by TFA. Then, the 4-amino and 5-hydroxyl groups were protected as a ketal by the treatment of 2,2-dimethoxypropane. After the 4-amino group of the building block compound was acetylated, an alkyl group (R1) was introduced to the free 5-hydroxyl group using various alkyl halides and a base (NaH or NaOMe) for the side chain functionality at the i position. Subsequently, the ketal was removed by an acidic treatment and a second alkylation reaction was carried out to place a functional group (R2) for the i+2 position. The second building block (compound 64) was coupled using BOP or PyBrOP to form a bis-benzamide. The steps (alkylation, deprotection, and another alkylation) were repeated to prepare the compounds 64, 66, 68 and 70.

For example, the present invention includes an oligo-benzamide peptidomimetic compound having the following formula:

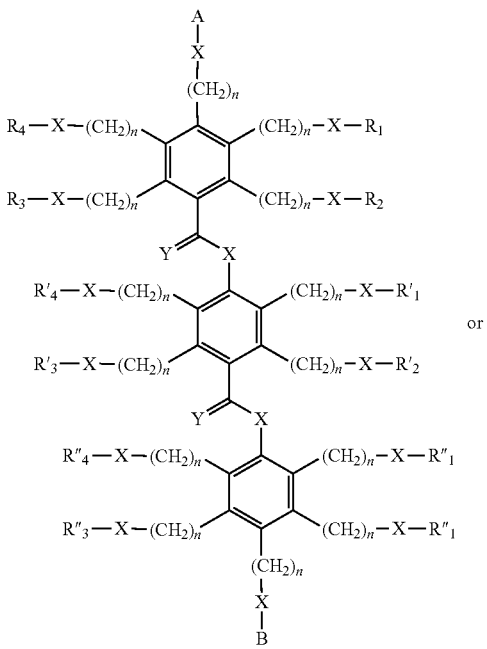

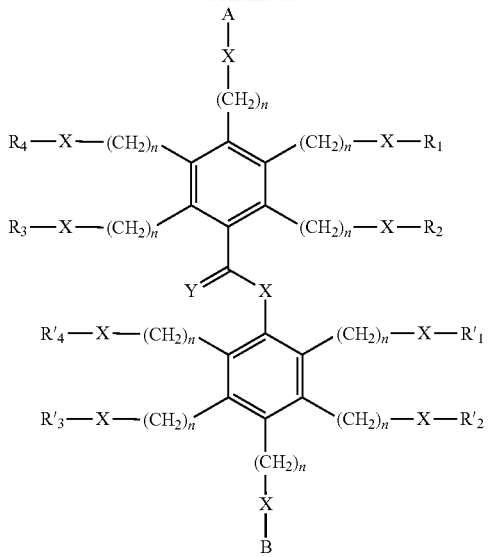

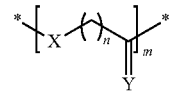

or a combination thereof.

"B" may be a substituent (R1, R2, R3, R4, R'1, R'2, R'3, R'4, R"1, R"2, R"3, or R"4), an optionally substituted alkyl, lower alkyl, an optionally substituted C1-C7 alkyl, an amino acid, an amino acid analogue, an artificial amino acid, a dipeptide, a tripeptide, a tetrapeptide, or a pentapeptide; a peptide sequence of between 2 and 30 amino acids; a linker of 1-20 amino acids, an optionally substituted C1-C7 alkyl or a linker as listed below:

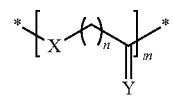

or a combination thereof, which may be optionally connected to one or more of the compounds M1-M12 listed in FIG. 10, or 14A to 14B of FIG. 14; or a combinations thereof.

Figures 9A, 9N:
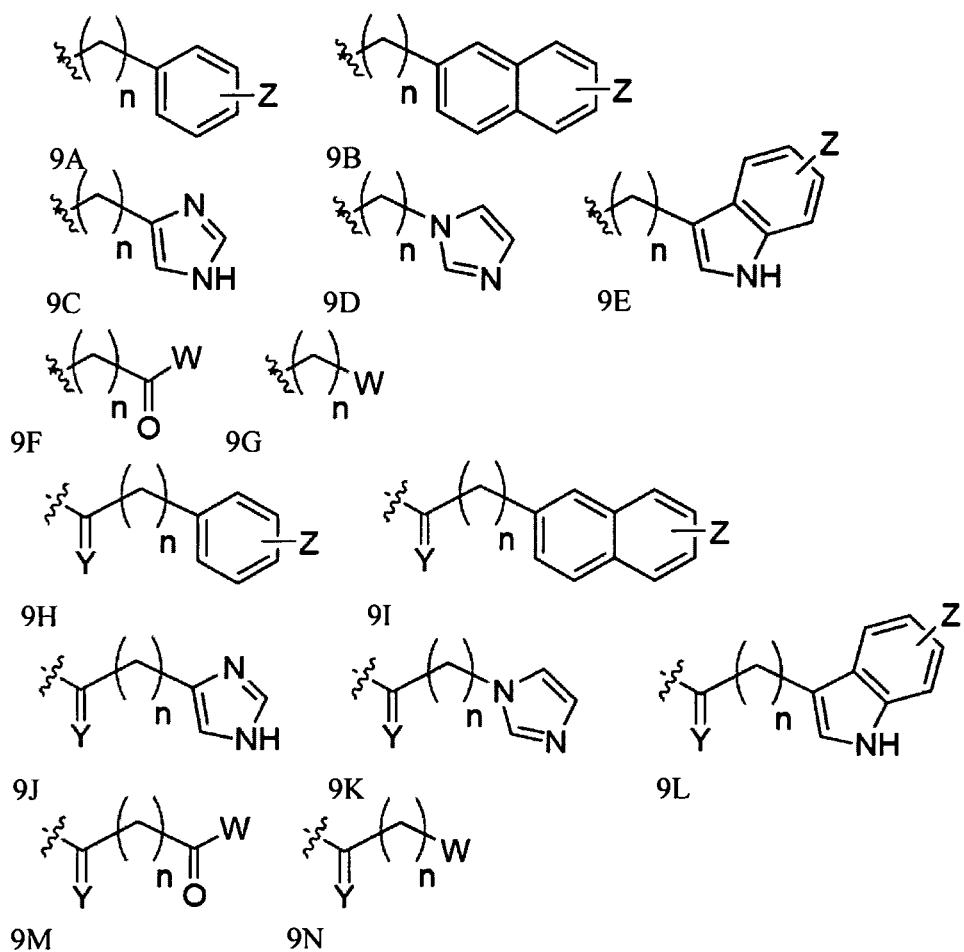
FIGS. 9A-9N are images of various structures of substituted groups that may be placed at the R positions of the α-helix peptidomimetic compounds.
Figure 11:
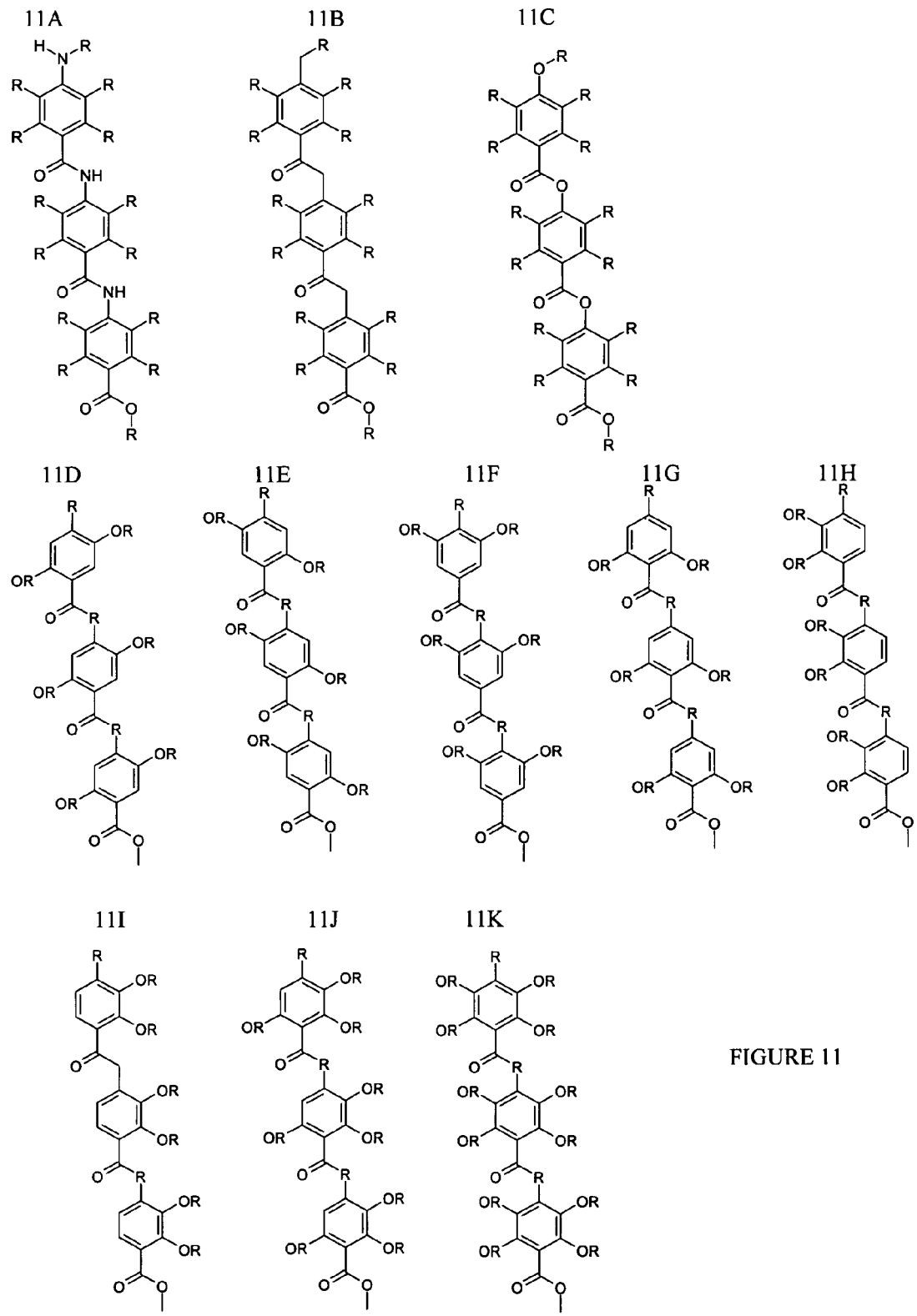
FIGS. 11A-11K are structures of various α-helix peptidomimetics compounds.

FIGS. 11A-11K are images that illustrate various α-helix mimetic compounds of the present invention. FIGS. 11A-11C provide general structures indicating examples of the modification to the bonds that link the individual benzamides. FIGS. 11D-11K are images that illustrate various α-helix mimetic compounds of the present invention. This provides the basic structure indicating examples of the locations on the rings that may be substituted with various groups to provide different characteristics. In addition, R may individually be substituted with various groups to provide different characteristics, e.g., optionally substituted alkyl, lower alkyl, C1-C7 alkyl, alkoxy groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, urea groups, carboxyl groups, carbonyl groups, alkoxycarbonyl groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or a combination thereof. For example, R may include independently one or more of the structures listed in FIG. 9, where Z is a OH, NH2, SH, F, Cl, Br or I; W is a OH, OR, NH2, NHR, NRR' or CN3H4; n is 0, 1, 2, 3, 4, 5, 6, 7 etc.; and Y is a N, a O, a S or 2Hs.

Figure 12:
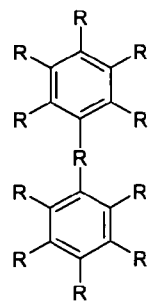
FIGS. 12A-12M are structures of another subset of the α-helix peptidomimetics compounds described in the current invention.
Figure 12:
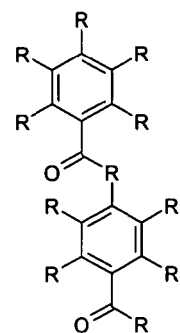
Figure 12:
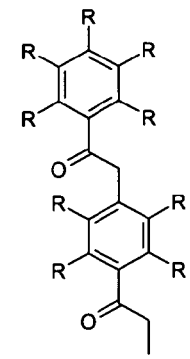
Figure 12:
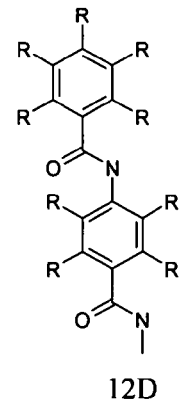
Figure 12:
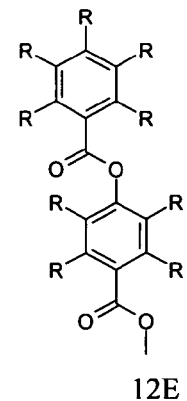
Figure 12:
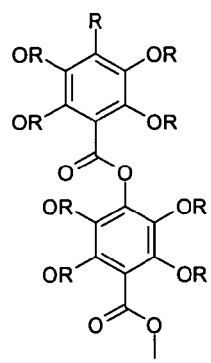
Figure 12:
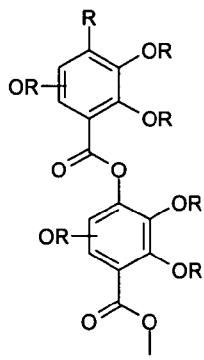
Figure 12:
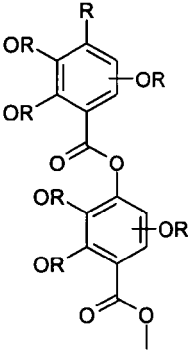
Figure 12:
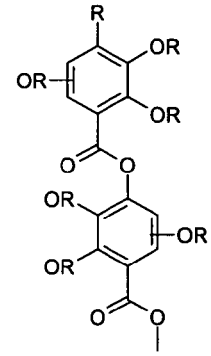
Figure 12:
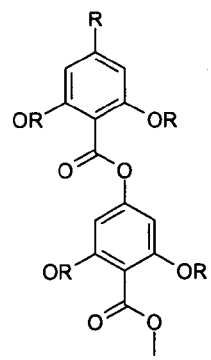
Figure 12:
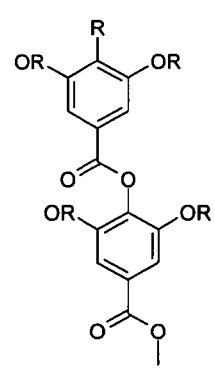
Figure 12:
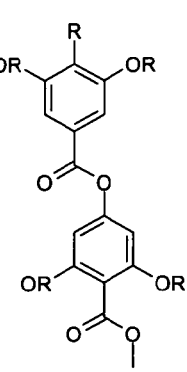
Figure 12:
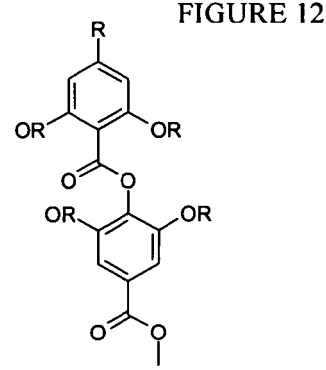
Figure 13A:
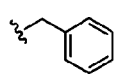
FIGS. 13A-13K are structures of additional subset of the α-helix peptidomimetics compounds described in the current invention.
Figure 13A:
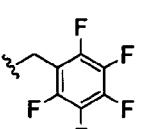
Figure 13A:
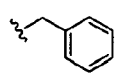
Figure 13A:
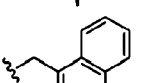
Figure 13A:
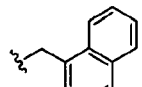
Figure 13A:
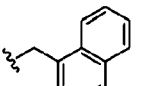
Figure 13A:
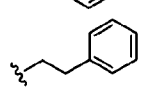
Figure 13A:
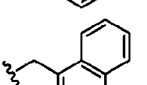
Figure 13A:
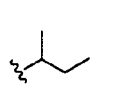
Figure 13A:
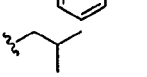
Figure 13A:
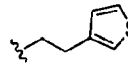
Figure 13A:
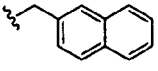
Figure 13A:
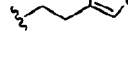
Figure 13A:
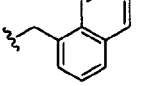
Figure 13A:
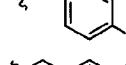
Figure 13A:
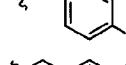
Figure 13A:
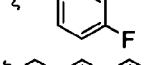
Figure 13A:
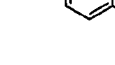
Figure 13A:
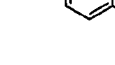
Figure 13A:
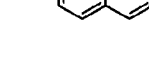
Figure 13B:
Figure 13B:
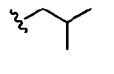
Figure 13B:
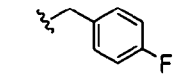
Figure 13B:
Figure 13B:
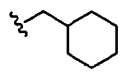
Figure 13B:
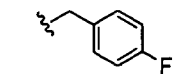
Figure 13B:
Figure 13B:
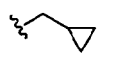
Figure 13B:
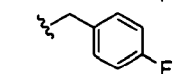
Figure 13B:
Figure 13B:
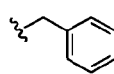
Figure 13B:
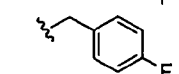
Figure 13B:
Figure 13B:
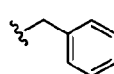
Figure 13B:
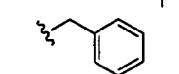
Figure 13B:
Figure 13B:
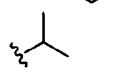
Figure 13B:
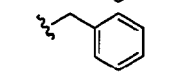
Figure 13B:
Figure 13B:
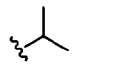
Figure 13B:
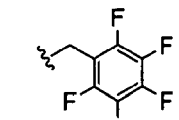
Figure 13B:
Figure 13B:
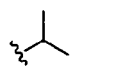
Figure 13B:
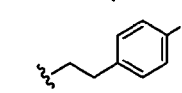
Figure 13B:
Figure 13B:
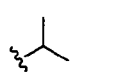
Figure 13B:
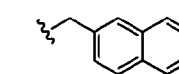
Figure 13B:
Figure 13B:
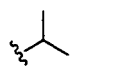
Figure 13B:
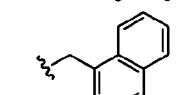
Figure 13B:
Figure 13B:
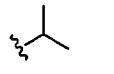
Figure 13B:
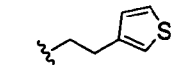
Figure 13B:
Figure 13B:
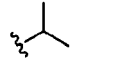
Figure 13B:
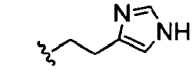
Figure 13B:
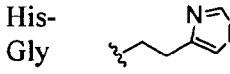
Figure 13B:
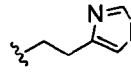
Figure 13B:
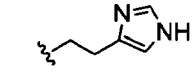
Figure 13B:
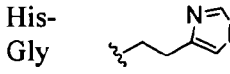
Figure 13B:
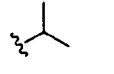
Figure 13B:
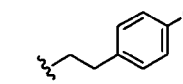
Figure 13B:
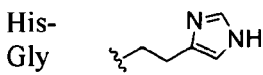
Figure 13B:
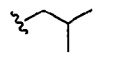
Figure 13B:
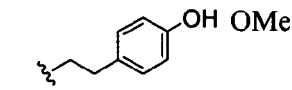
Figure 13B:
Figure 13B:
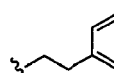
Figure 13B:
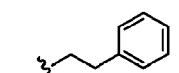
Figure 13B:
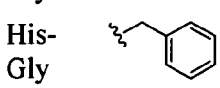
Figure 13B:
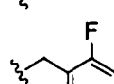
Figure 13B:
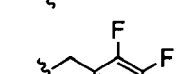
Figure 13C:
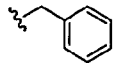
Figure 13C:
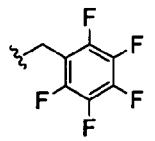
Figure 13C:
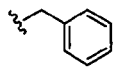
Figure 13C:
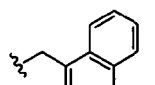
Figure 13C:
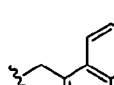
Figure 13C:
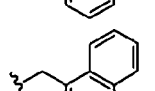
Figure 13C:
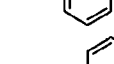
Figure 13C:
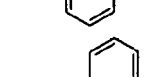
Figure 13C:
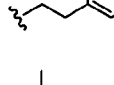
Figure 13C:
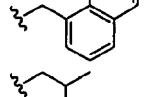
Figure 13C:
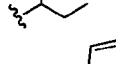
Figure 13C:
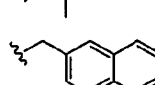
Figure 13C:
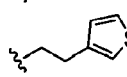
Figure 13C:
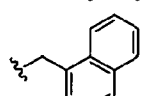
Figure 13C:
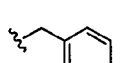
Figure 13C:
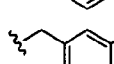
Figure 13C:
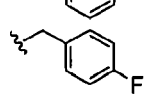
Figure 13C:
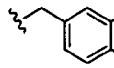
Figure 13C:
Figure 13C:
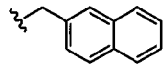
Figure 13D:
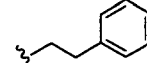
Figure 13D:
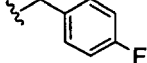
Figure 13D:
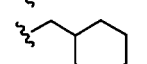
Figure 13D:
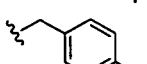
Figure 13D:
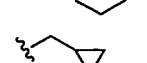
Figure 13D:
Figure 13D:
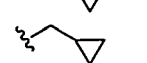
Figure 13D:
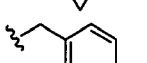
Figure 13D:
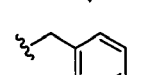
Figure 13D:
Figure 13D:
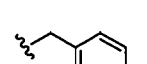
Figure 13D:
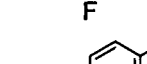
Figure 13D:
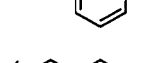
Figure 13D:
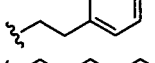
Figure 13D:
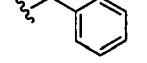
Figure 13D:
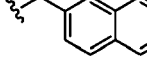
Figure 13D:
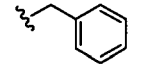
Figure 13D:
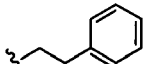
Figure 13D:
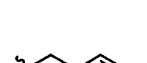
Figure 13D:
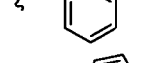
Figure 13D:
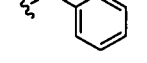
Figure 13D:
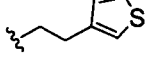
Figure 13D:
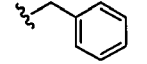
Figure 13D:
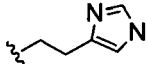
Figure 13D:
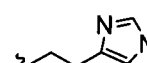
Figure 13D:
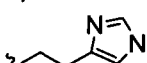
Figure 13D:
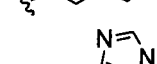
Figure 13D:
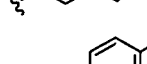
Figure 13D:
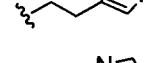
Figure 13D:
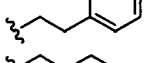
Figure 13D:
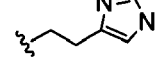
Figure 13D:
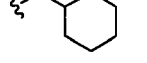
Figure 13D:
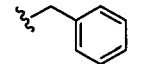
Figure 13D:
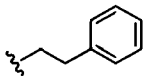
Figure 13D:
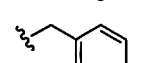
Figure 13D:
Figure 13D:
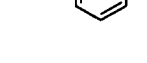
Figure 13D:
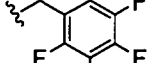
Figure 13D:
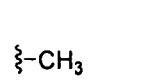
Figure 13D:
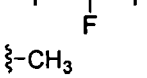
Figure 13D:
Figure 13D:
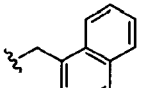
Figure 13D:
Figure 13D:
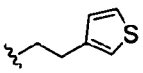
Figure 13D:
Figure 13D:
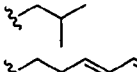
Figure 13D:
Figure 13D:
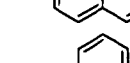
Figure 13D:
Figure 13D:
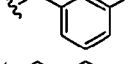
Figure 13D:
Figure 13D:
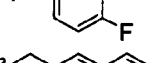
Figure 13E:
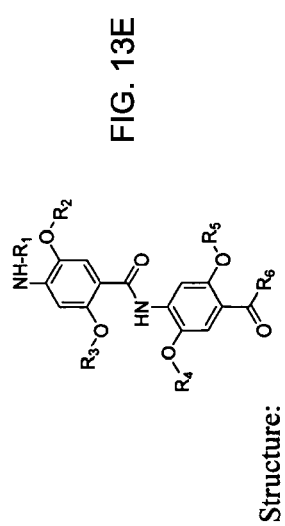
Figure 13E:
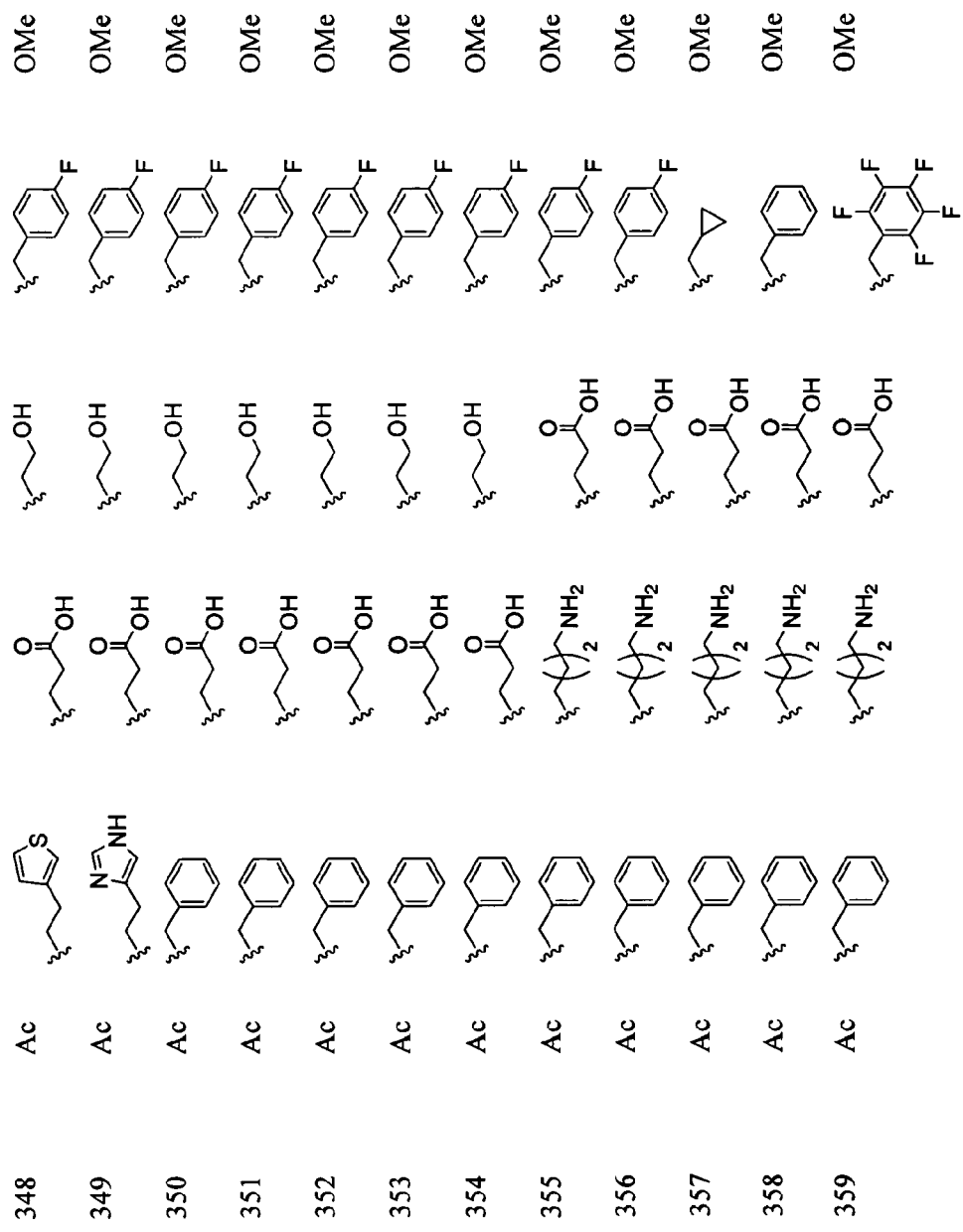
Figure 13E:
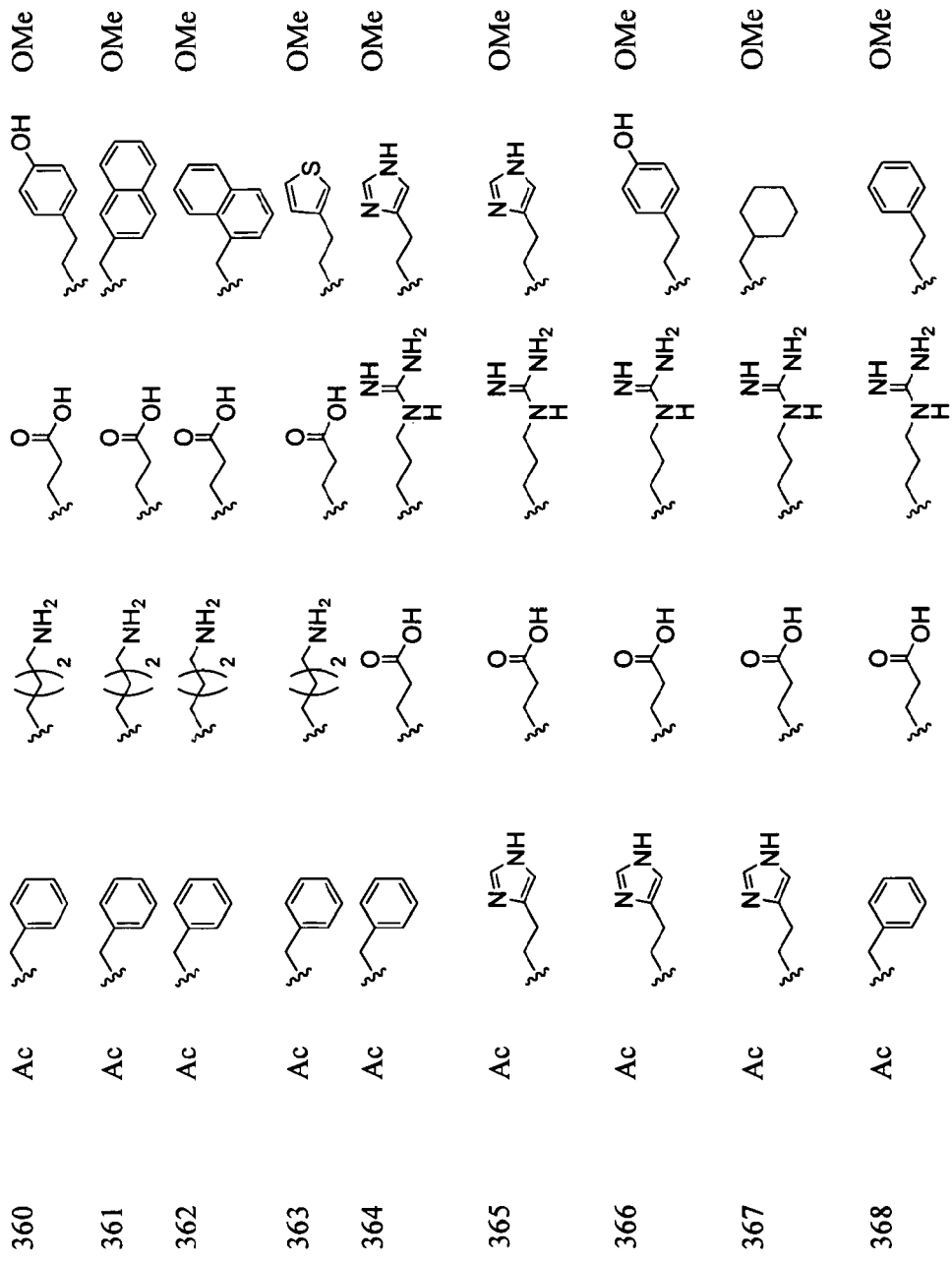
Figure 13E:
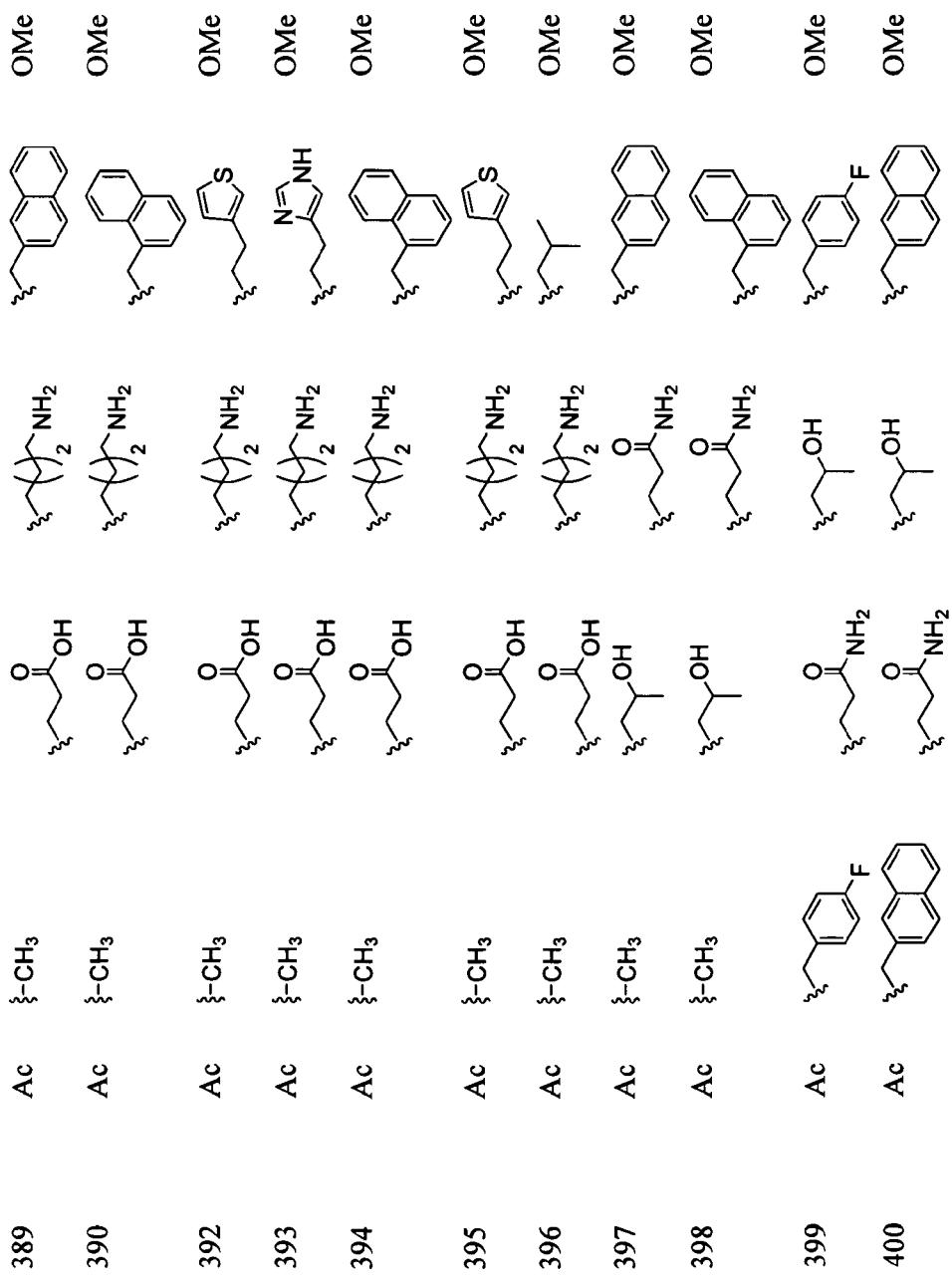
Figure 13F:
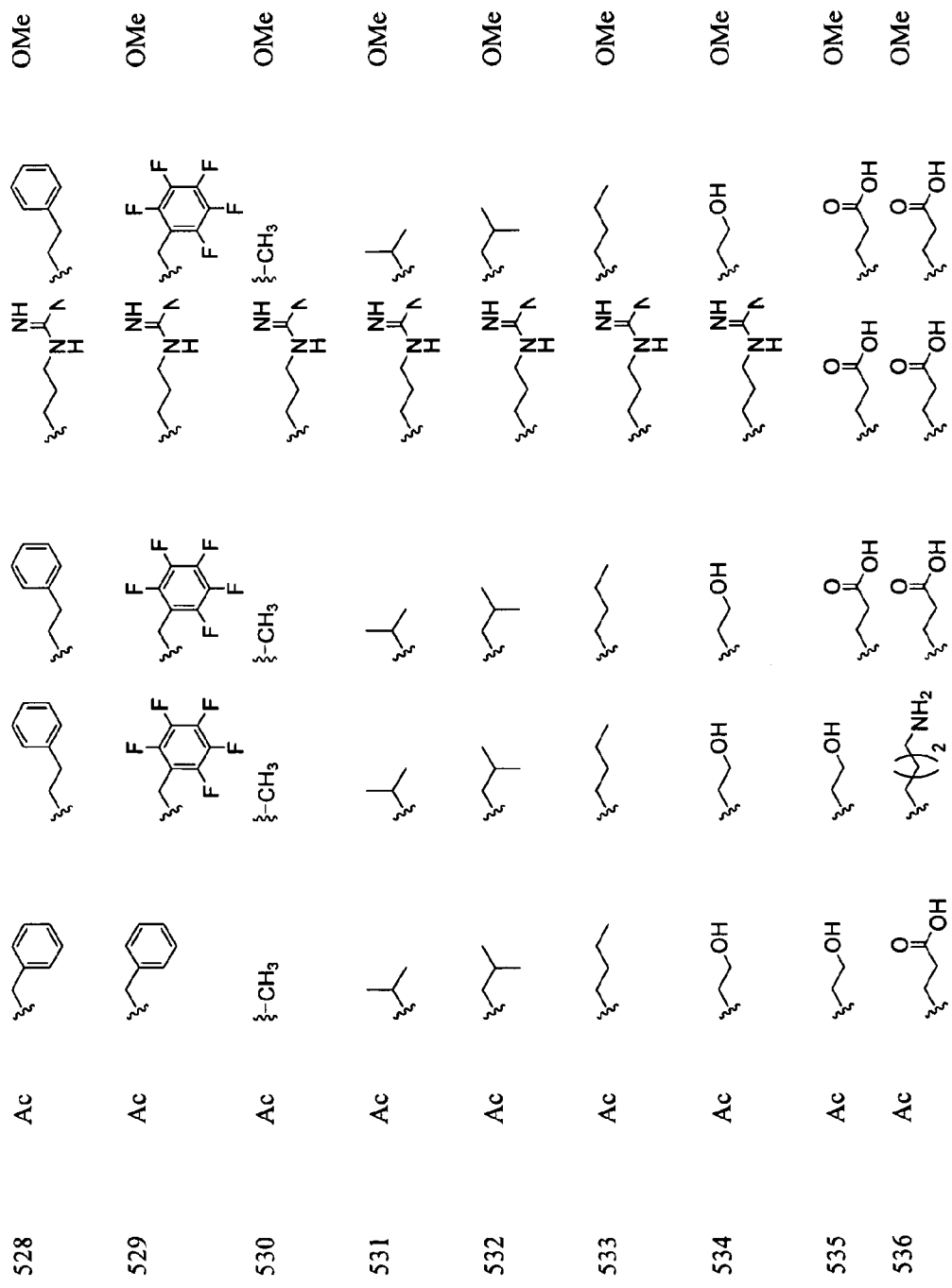
Figure 13G:
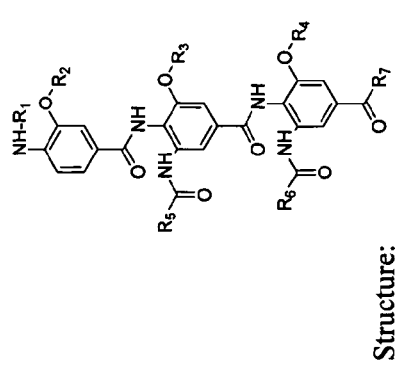
Figure 13G:
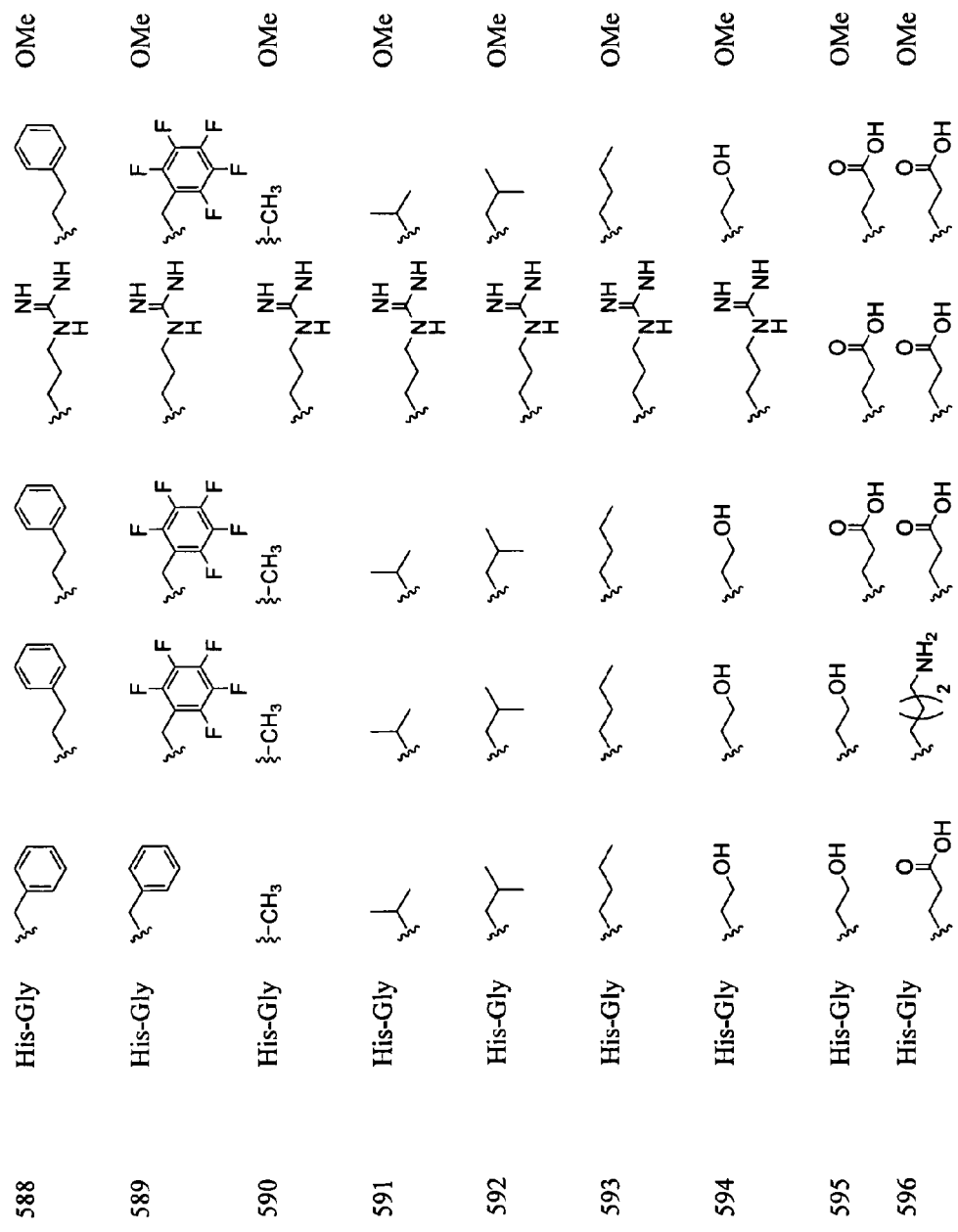
Figure 13G:
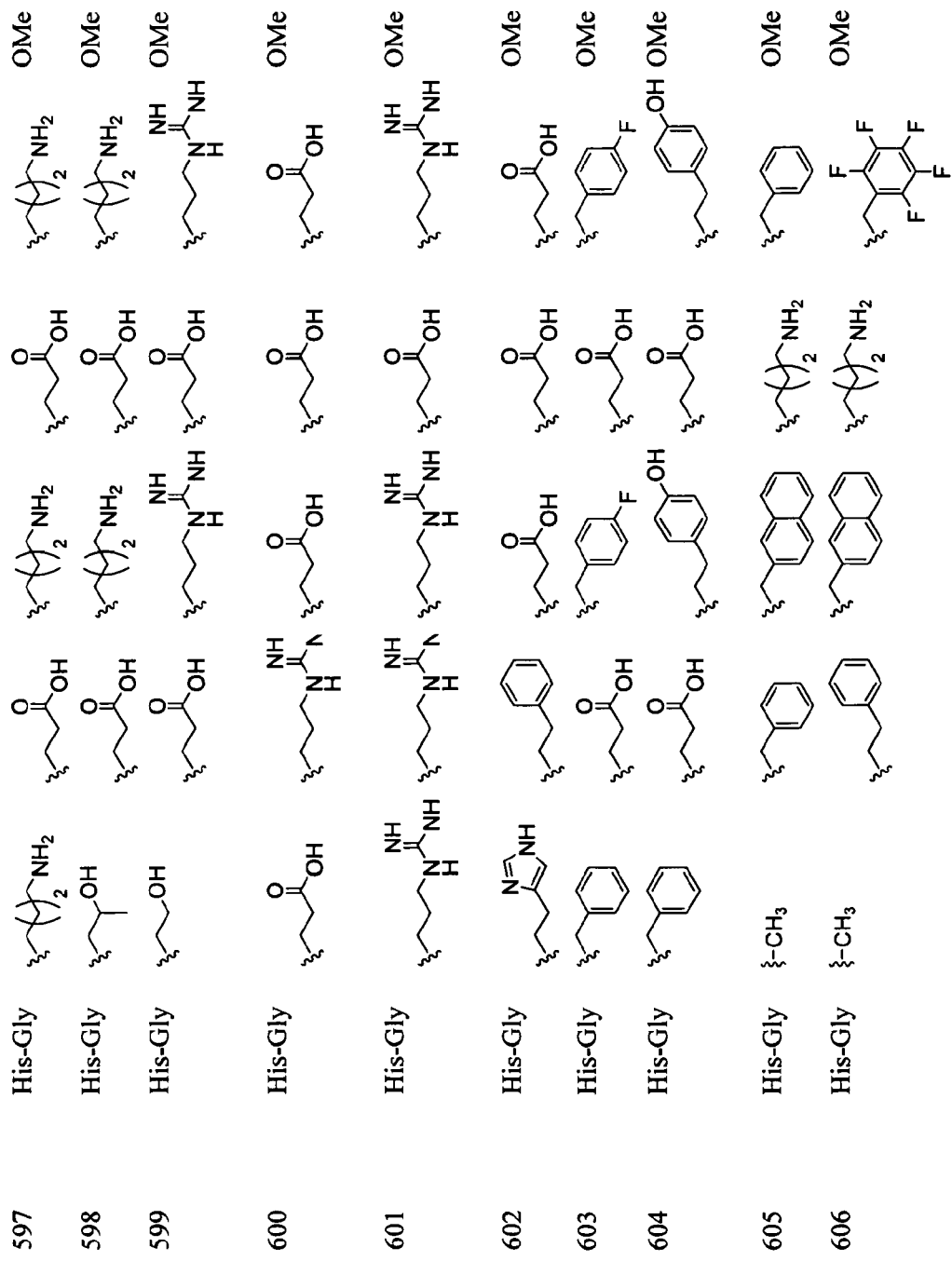
Figure 13H:
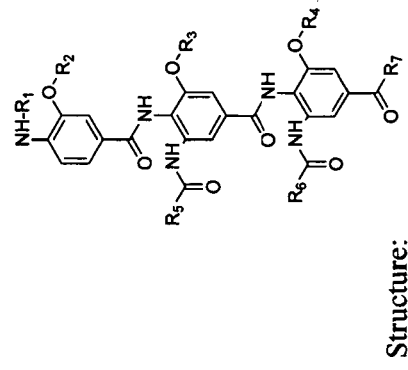
Figure 13H:
Figure 13H:
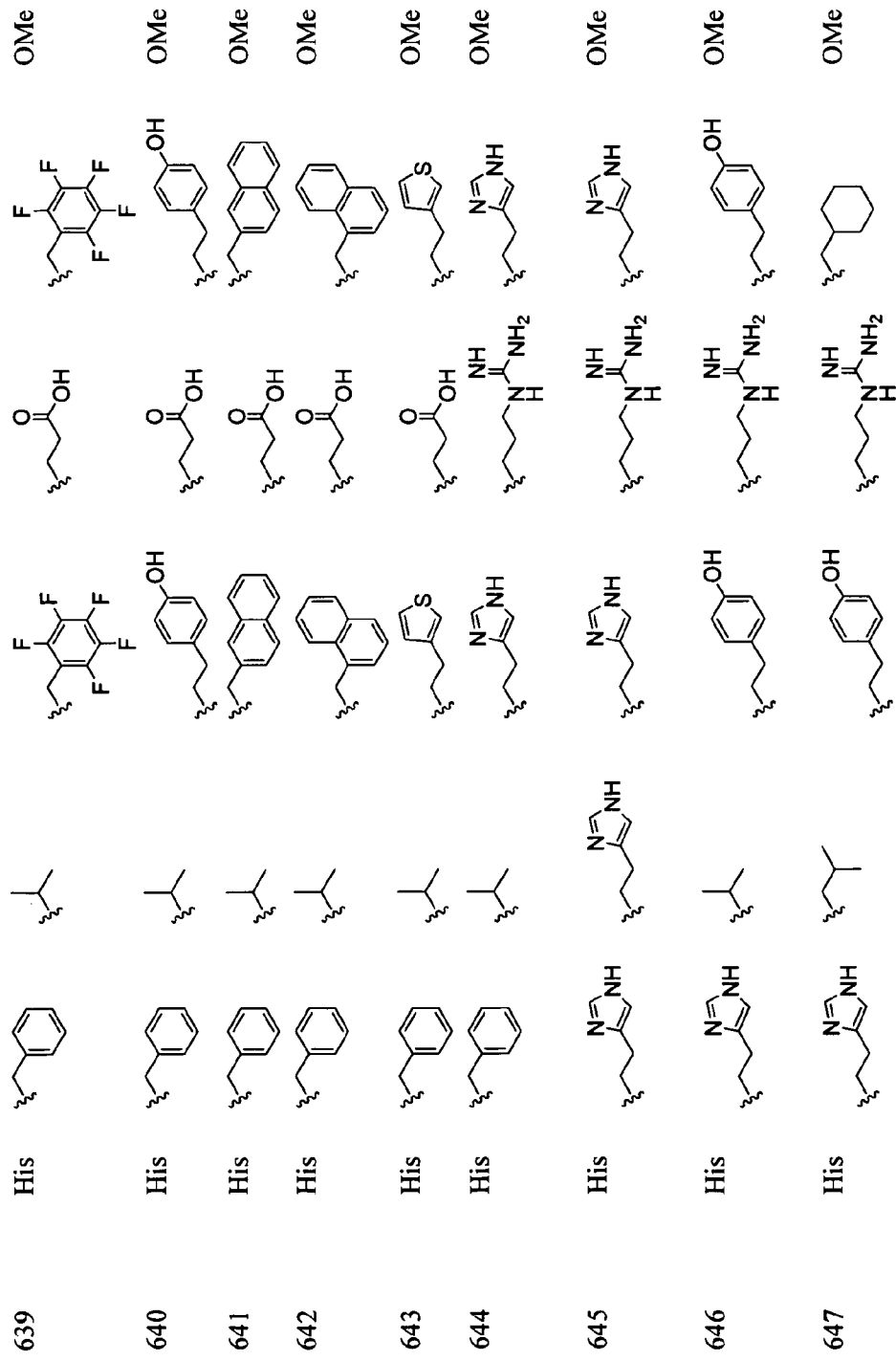
Figure 13I:
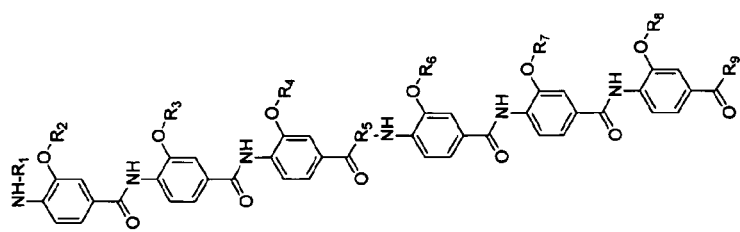
Figure 13I:
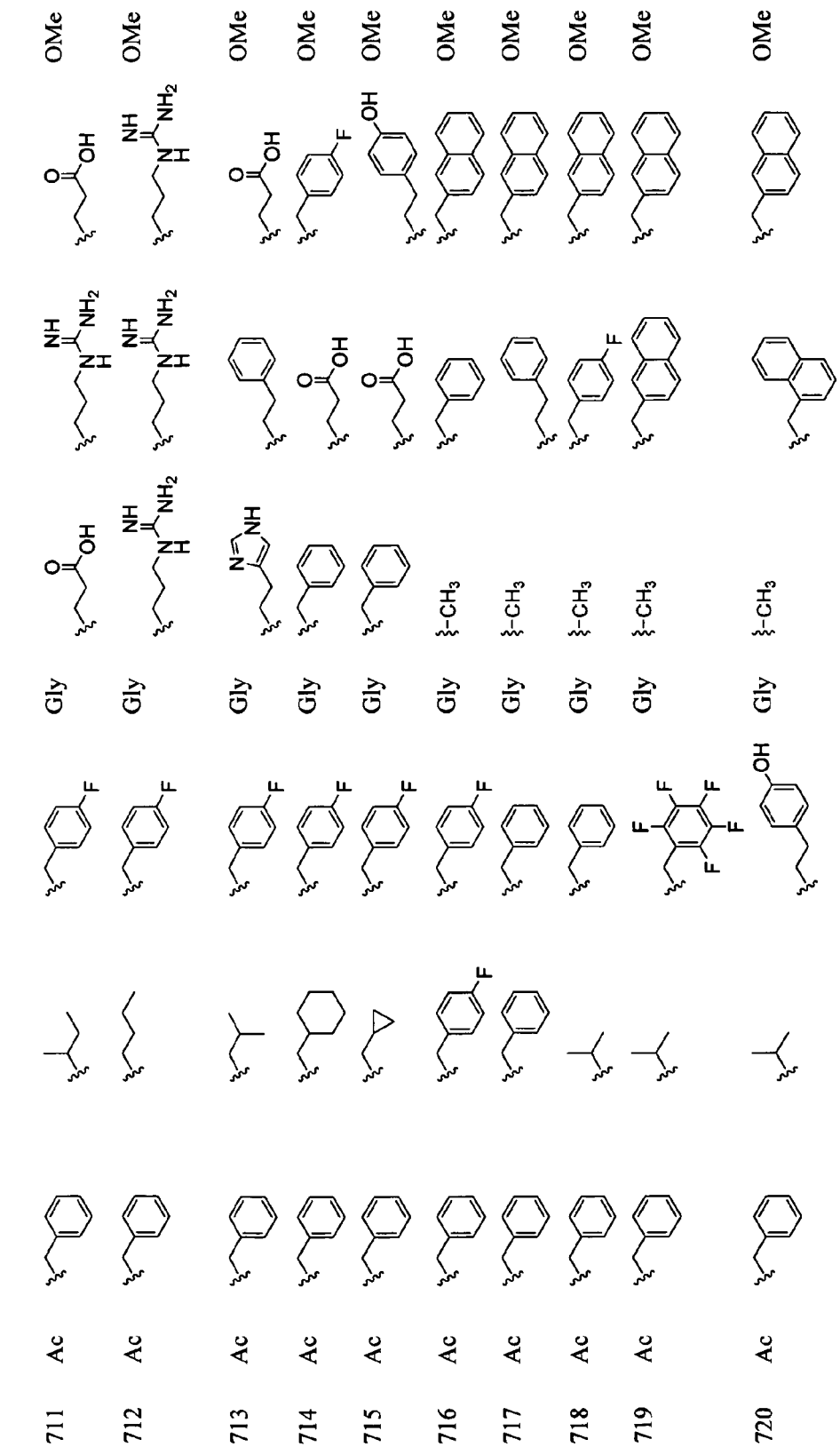
Figure 13I:
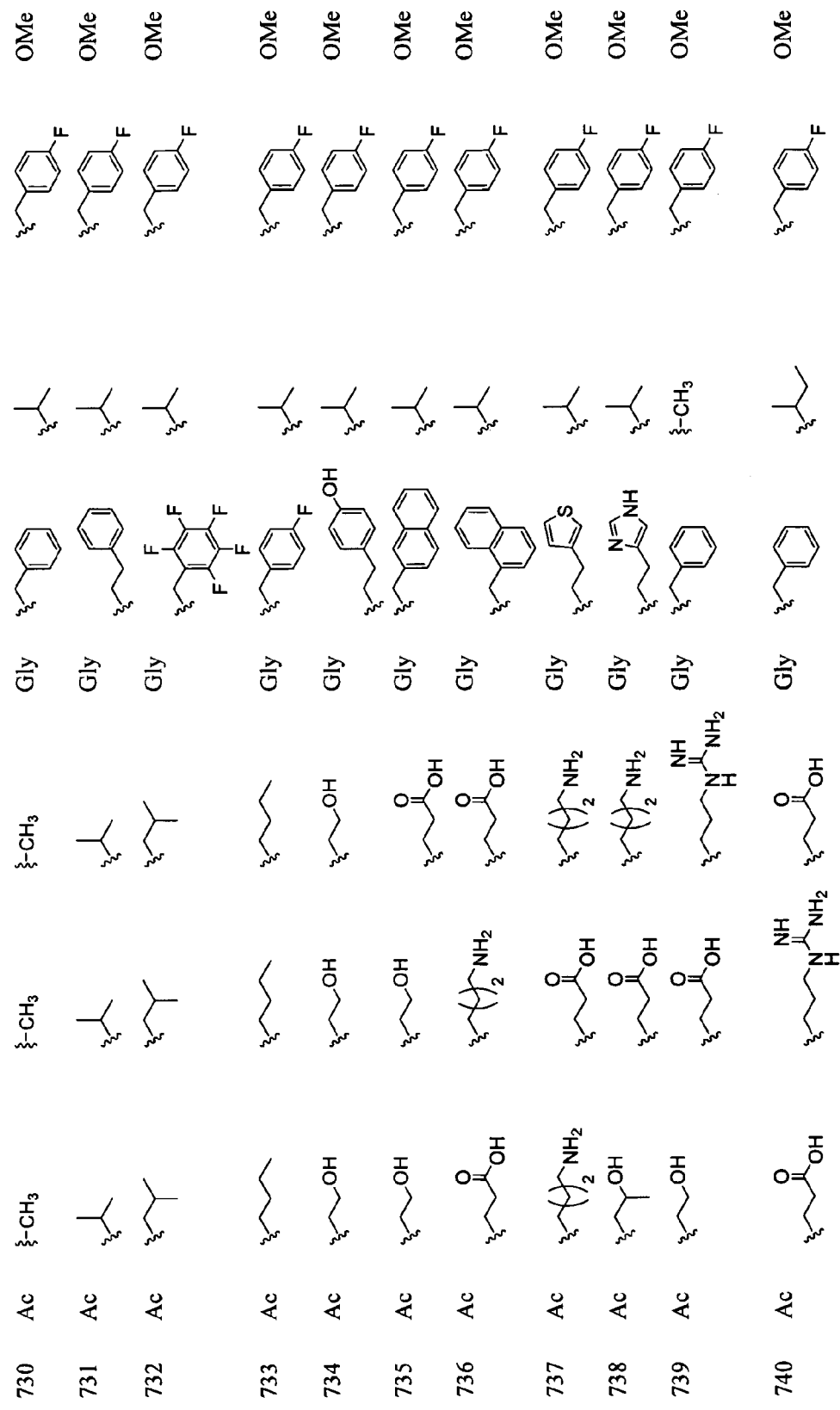
Figure 13I:
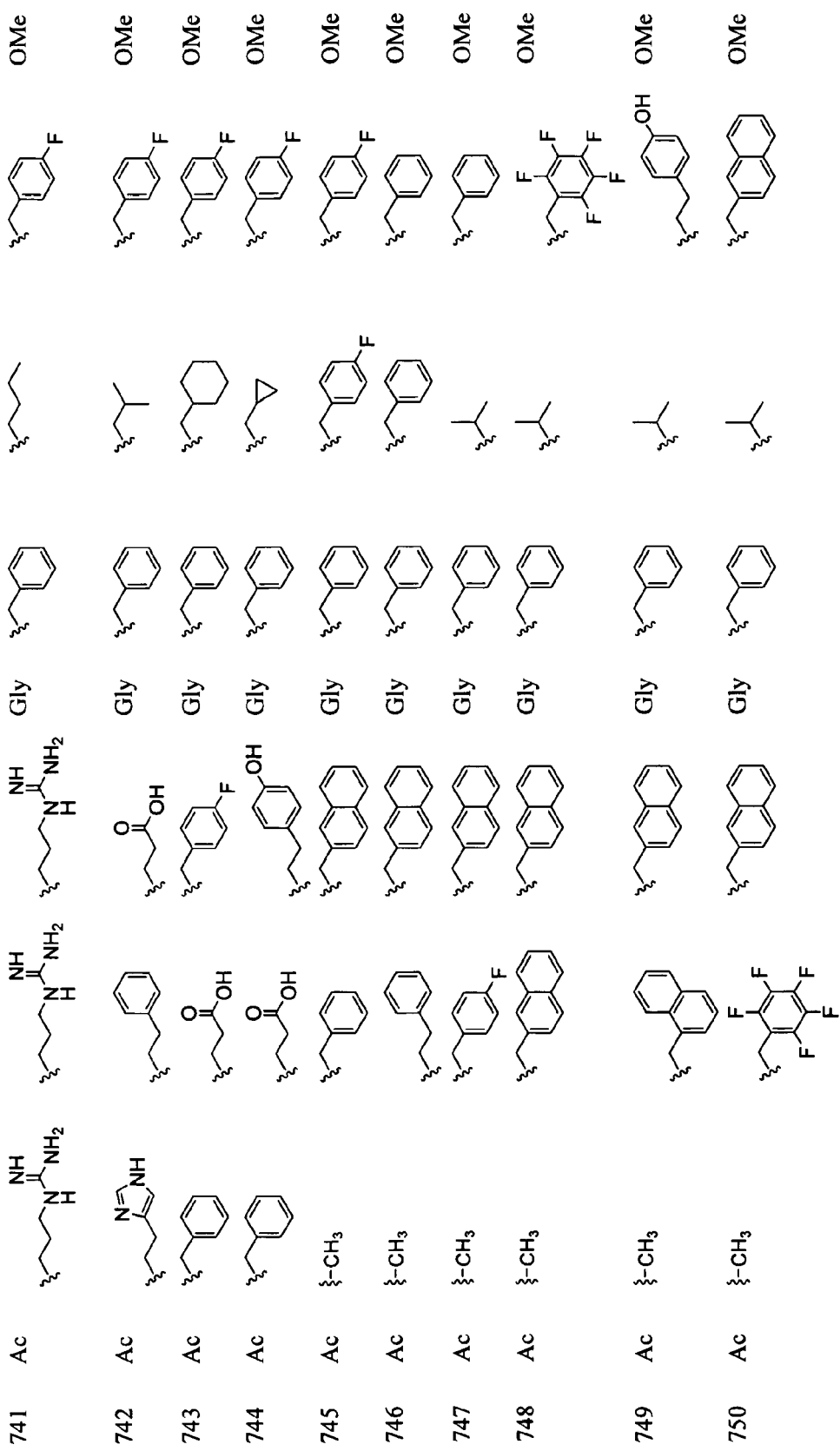
Figure 13I:
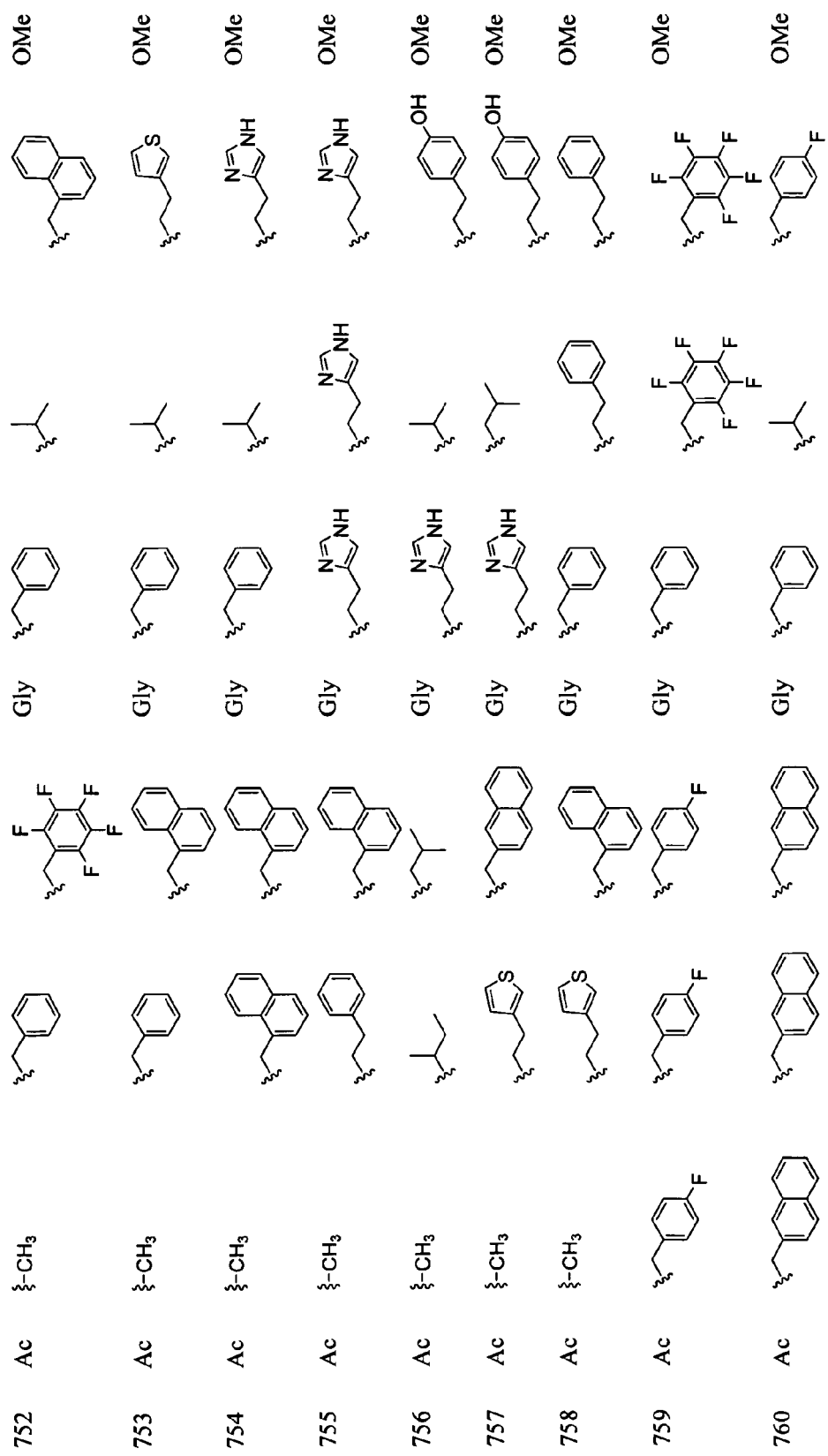
Figure 13J:
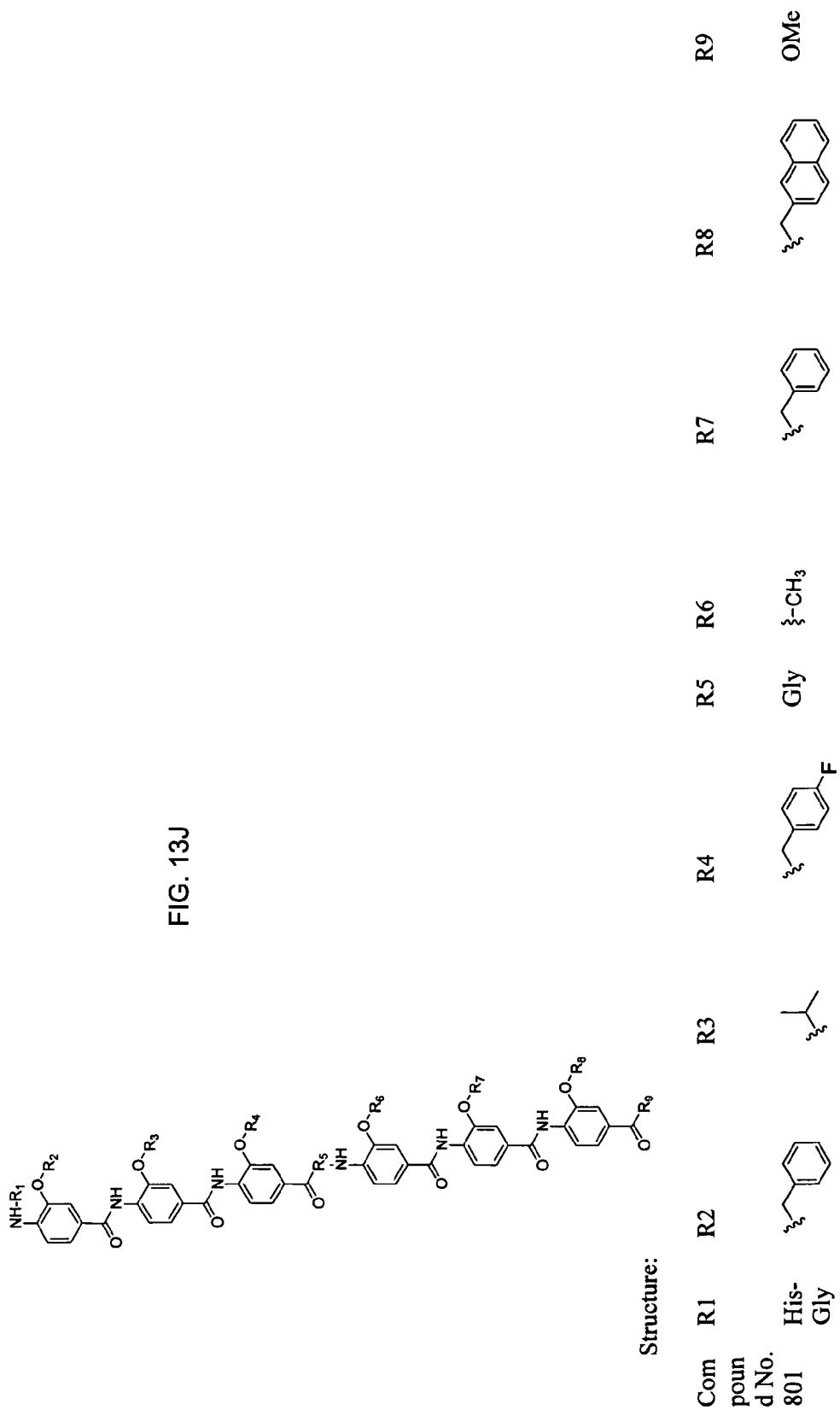
Figure 13J:
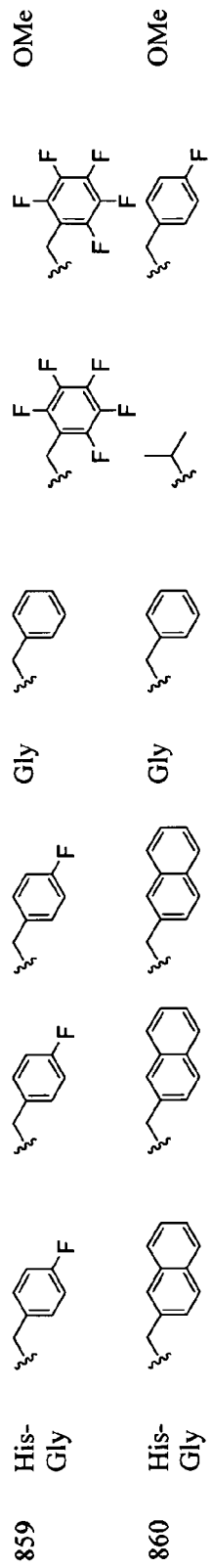
Figure 13K:
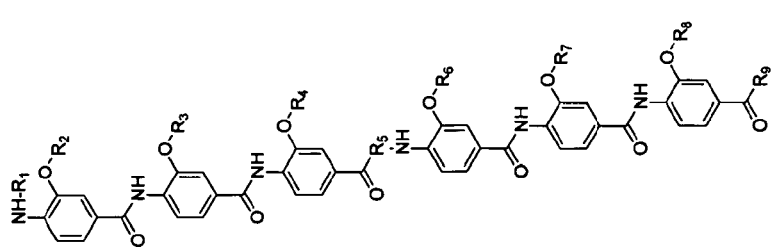
Figure 13K:
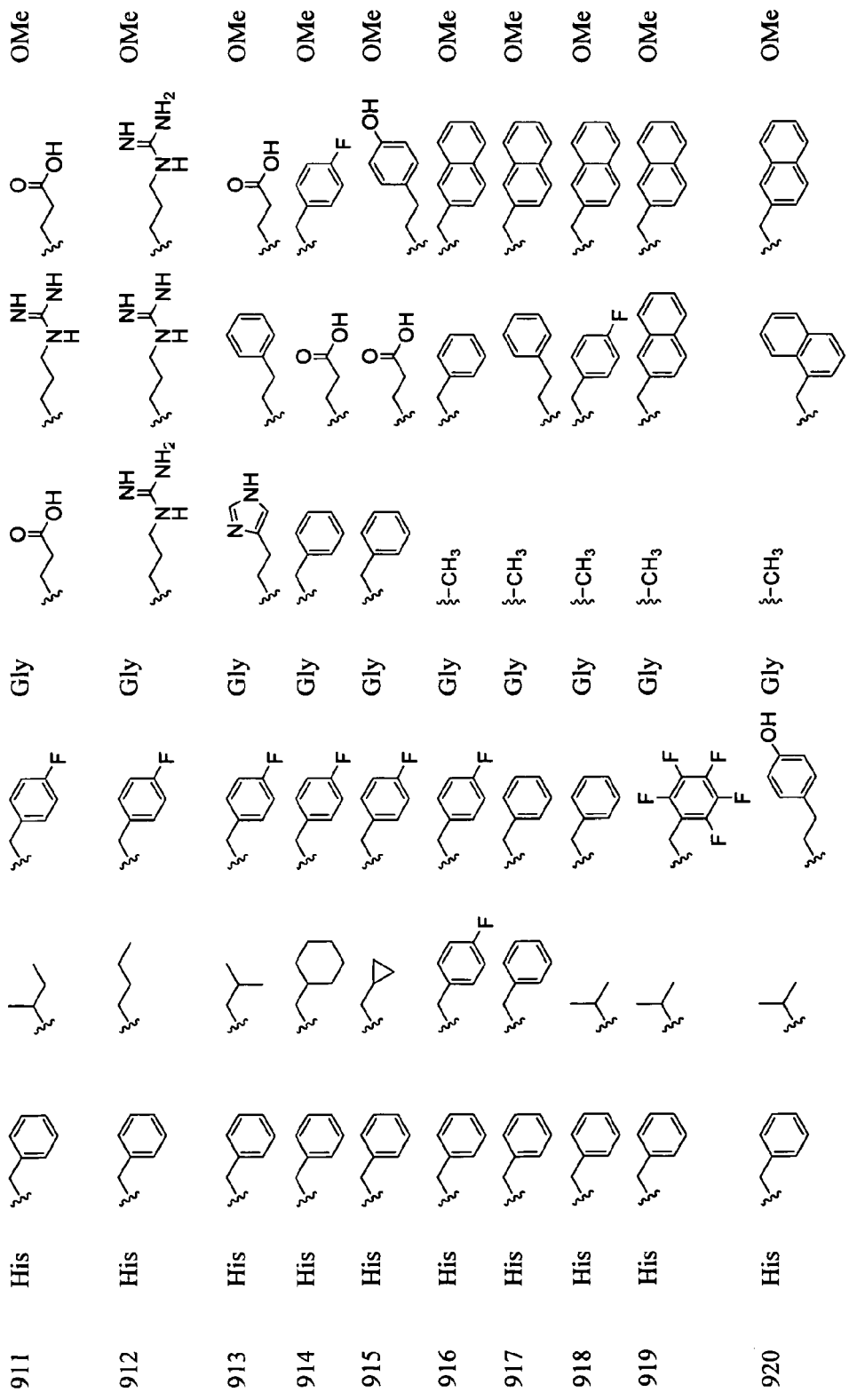
Figure 13K:
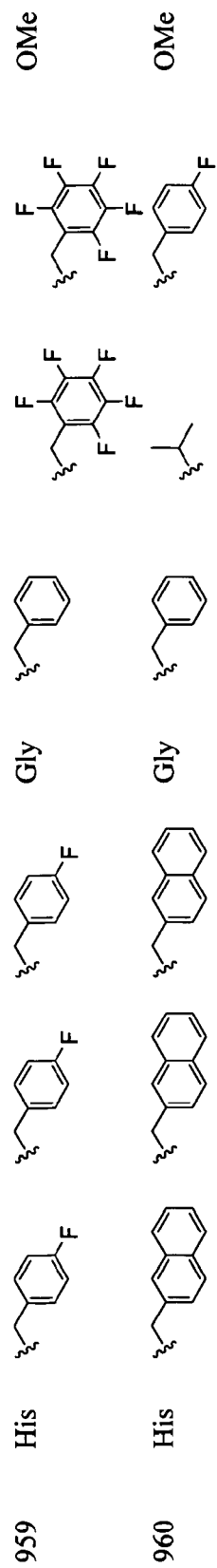

FIGS. 12A-12M are images that illustrate various α-helix mimetic compounds of the present invention. FIGS. 12A-12B provide the general structures indicating examples of the modification to the bonds that link the 2 individual benzamides. FIGS. 12C-12E provide specific examples of the general structure of the modification to the bonds that link the individual benzamides. FIGS. 12F-12M are images that illustrate various α-helix mimetic compounds of the present invention. This provides the basic structure indicating examples of the locations on the rings that may be substituted wherein X is independently a C, a N, a O, a S, a H, —CH$_2$CH$_2$—, —CH=CH—, —C≡C—, —NH—, —NR—, —NH—NH—, —NH(CH$_2$)$_n$NH, —NR(CH$_2$)$_n$NR'— —NR—NR'—, —NH—O—, —NR—O—, —NH(CH$_2$)$_n$O—, —NR(CH$_2$)$_n$O—, —NH(CH$_2$)$_n$S—, —NR(CH$_2$)$_n$S—, —O(CH$_2$)$_n$O—, —O(CH$_2$)$_n$S—, —S(CH$_2$)$_n$S—, —CO—, —CO$_2$—, —COS—, —CONH—, —CONR—, —OC(O)NH—, —NHCONH—, —CONHCO—, —CO(CH$_2$)$_n$CO—, or combination thereof, wherein Y is independently a N, a O, a S or 2Hs; wherein R1, R2, R3, R4, R'1, R'2, R'3, R'4, R"1, R"2, R"3, and R"4, comprise independently a H, optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkyl-alkyl, arylthio, alkylthio, alkylsulfinyl, alkylsulfonyl, arylsulfonyl, arylsulfinyl, caboxamido, carbamoyl, carboxyl, carbonyl, alkoxycarbonyl, halogen, haloalkyl, haloalkoxy, heteroayl, heterocyclic ring, arylheterocyclic ring, heterocyclic compounds, amido, imido, guanidino, hydrazido, aminoxy, alkoxyamino, alkylamido, urea, carboxylic ester, thioethers, carboxylic acids, phosphoryl groups, polycyclic aromatic substituted with a OH, NH$_2$, SH, F, Cl, Br, I, NHR, NRR', CN$_3$H$_4$, a N, a O, a S, a H, or combination thereof. And, n is 0, 1, 2, 3, 4, 5, 6, 7 etc. For example R1, R2, R3, R4, R'1, R'2, R'3, R'4, R"1, R"2, R"3, and R"4, may include independently one or more of the structures listed in FIG. 9, where Z is a OH, NH$_2$, SH, F, Cl, Br or I; W is a OH, OR, NH$_2$, NHR, NRR' or CN$_3$H$_4$; n is 0, 1, 2, 3, 4, 5, 6, 7 etc.; and Y is a N, a O, a S or 2Hs.

"A" may be a substituent (R1, R2, R3, R4, R'1, R'2, R'3, R'4, R"1, R"2, R"3, or R"4), an acetyl, Boc (t-butoxycarbonyl), a Fmoc (9-fluorenylmethoxycarbonyl), a Cbz (benzyloxycarbonyl), an Aloc (allyloxycarbonyl), an amino acid, an amino acid analogue, an artificial amino acid, a dipeptide, a tripeptide, a tetrapeptide, or a pentapeptide. "A" may be a peptide sequence of between 2 and 30 amino acids. "A" may be a linker of 1-20 amino acids, an optionally substituted lower alkyl, an optionally substituted C1-C7 alkyl, a linker as listed below:

with various groups to provide different characteristics. In addition, R may individually be substituted with various groups to provide different characteristics, e.g., R may be optionally substituted alkyl, lower alkyl, C1-C7 alkyl, alkoxy groups, lower alkyl groups, alkoxy groups, alkoxyalkyl groups, hydroxy groups, hydroxyalkyl groups, alkenyl groups, amino groups, imino groups, nitrate groups, alkylamino groups, nitroso groups, aryl groups, biaryl groups, bridged aryl groups, fused aryl groups, alkylaryl groups, arylalkyl groups, arylalkoxy groups, arylalkylamino groups, cycloalkyl groups, bridged cycloalkyl groups, cycloalkoxy groups, cycloalkyl-alkyl groups, arylthio groups, alkylthio groups, alkylsulfinyl groups, alkylsulfonyl groups, arylsulfonyl groups, arylsulfinyl groups, caboxamido groups, carbamoyl groups, carboxyl groups, carbonyl groups, alkoxycarbonyl groups, urea groups, halogen groups, haloalkyl groups, haloalkoxy groups, heteroayl, heterocyclic ring, arylheterocyclic ring, heterocyclic compounds, amido, imido, guanidino, hydrazido, aminoxy, alkoxyamino, alkylamido, carboxylic ester groups, thioethers groups, carboxylic acids, phosphoryl groups or combination thereof. For example, R may include independently one or more of the structures listed in FIG. 9, where Z is a OH, $NH_2$, SH, F, Cl, Br or I; W is a OH, OR, $NH_2$, NHR, NRR' or $CN_3H_4$; n is 0, 1, 2, 3, 4, 5, 6, 7 and so forth.; and Y is a N, a O, a S or 2Hs.

FIGS. 13A-13K provide specific examples of the structure of the various individual α-helix mimetic compounds of the present invention. FIGS. 13A-13K provide the general structure of the compound with the R group positions indicated. The table lists the compound numbers 100-960 and indicates the functional groups at each R group on the general structure of the α-helix mimetic compound to provide different characteristics.

FIGS. 14A-14F are images that illustrate various α-helix mimetic compounds of the present invention. FIGS. 14A and 14B provide the general structure of the α-helix mimetic compounds. X may independently be a C, a N, a O, a S, a H, —$CH_2CH_2$—, —CH═CH—, —C≡C—, —NH—, —NR—, —NH—NH—, —$NH(CH_2)_nNH$—, —$NR(CH_2)_nNR'$— —NR—NR'—, —NH—O—, —NR—O—, —$NH(CH_2)_nO$—, —$NR(CH_2)_nO$—, —$NH(CH_2)_nS$—, —$NR(CH_2)_nS$—, —$O(CH_2)_nO$—, —$O(CH_2)_nS$—, —$S(CH_2)_nS$—, —CO—, —$CO_2$—, —COS—, —CONH—, —CONR—, —OC(O)NH—, —NHCONH—, —CONHCO—, —$CO(CH_2)_nCO$—, or combination thereof, and Y may be independently a N, a O, a S or 2H's. And, n is 0, 1, 2, 3, 4, 5, 6, 7 etc. R1, R2, R3, R4, R'1, R'2, R'3, R'4, R"1, R"2, R"3, and R"4, comprise independently a H, optionally substituted alkyl, lower alkyl, alkoxy, alkoxyalkyl, hydroxy, hydroxyalkyl, alkenyl, amino, imino, nitrate, alkylamino, dialkylamino, nitro, nitroso, aryl, biaryl, polycyclic aromatic, alkylaryl, arylalkyl, arylalkoxy, arylalkylamino, cycloalkyl, bridged cycloalkyl, cycloalkoxy, cycloalkyl-alkyl, arylthio, alkylthio, alkylsulfinyl, alkylsulfonyl, arylsulfonyl, arylsulfinyl, caboxamido, carbamoyl, carboxyl, carbonyl, alkoxycarbonyl, halogen, haloalkyl, haloalkoxy, heteroayl, heterocyclic ring, arylheterocyclic ring, heterocyclic compounds, amido, imido, guanidino, hydrazido, aminoxy, alkoxyamino, alkylamido, urea, carboxylic ester, thioethers, carboxylic acids, phosphoryl groups, polycyclic aromatic substituted with a OH, $NH_2$, SH, F, Cl, Br, I, NHR, NRR', $CN_3H_4$, a N, a O, a S, a H, or combination thereof. FIGS. 14C-14F provide several specific examples of the general structure. The compositions of the present invention may be an agonist, an inverse agonist, an antagonist, a partial agonist, a partial antagonist, a co-agonist, an activator, an inhibitor, or a combination thereof depending on the protein and the functional groups of the composition.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention.

All such similar substitutes and modifications apparent to those skilled in the art are deemed to be within the spirit, scope and concept of the invention as defined by the appended claims.

REFERENCES

1. U.K. Prospective Diabetes Study Group, United Kingdom prospective diabetes study 16, Overview of 6 years' therapy of type II diabetes: A progressive disease. Diabetes 1995, 44, 1249-1258.
2. Zhang, B. B.; Moller, D. E., New approaches in the treatment of type 2 diabetes. Curr. Opin. Chem. Biol. 2000, 4, 461-467.
3. Kahn, B. B., Type 2 diabetes: when insulin secretion fails to compensate for insulin resistance. Cell 1998, 92, 593-596.
4. Cavaghan, M. K.; Ehrmann, D. A.; Polonsky, K. S., Interactions between insulin resistance and insulin secretion in the development of glucose intolerance. J. Clin. Invest. 2000, 106, 329-333.
5. Mojsov, S.; Heinrich, G.; Wilson, I. B.; Ravazzola, M.; Orci, L.; Habener, J. F., Preproglucagon gene expression in pancreas and intestine diversifies at the level of post-translational processing. J. Biol. Chem. 1986, 261, 11880-11889.
6. Nauck, M. A.; Kleine, N.; Orskov, C.; Holst, J. J.; Willms, B.; Creuzfeldt, W., Normalization of fasting hyperglycemia by exogenous glucagon-like peptide-1 (7-36 amide) in type-2 (non-insulindependent) diabetic patients. Diabetologia 1993, 36, 741-744.
7. Bell, G. I.; Sanchez-Pescadore, R.; Layboum, P. L.; Najarian, R. C., Exon duplication and divergence in the human preproglucagon gene. Nature 1983, 304, 368-371.
8. Kieffer, T. J.; Habener, J. F., The glucagon-like peptides. Endocr. Rev. 1999, 20, 876-913.
9. Gutniak, M.; Orskov, C.; Holst, J. J.; Ahren, B.; Efendc, S., Antidiabetogenic effect of glucagon-like peptide-1 (7-36) amide in normal subjects and patients with diabetes mellitus. N. Engl. J. Med. 1992, 326, 1316-1322.
10. Thorens, B., Expression cloning of the pancreatic beta cell receptor for the gluco-incretin hormone glucagon-like peptide 1. Proc. Natl. Acad. Sci. U.S.A. 1992, 89, 8641-8645.
11. Holst, J. J.; Orskov, C.; Knuhtsen, S.; Baldissera, F. A. G.; Poulsen, S. S.; Nielsen, O. V., Truncated glucagon-like peptide I, an insulin-releasing hormone from the distal gut. FEBS Lett. 1987, 211, 169-174.
12. Mojsov, S.; Weir, C. G.; Habener, J. F., Insulinotropin: glucagon-like peptide 1 (7-37) co-encoded in the glucagon gene is a potent stimulator of insulin release in the perfused rat pancreas. J. Clin. Invest. 1987, 79, 616-619.
13. Kreymann, B.; Ghatei, M. A.; Williams, G.; Bloom, S. R., Glucagon-like peptide-17-36: a physiological incretin in man. Lancet 1987, 2, 1300-1303.
14. Drucker, D. J.; Philippe, J.; Mosjov, S.; Chick, W. L.; Habener, J. F., Glucagon-like peptide I stimulates insulin gene expression and increases cyclic AMP levels in a rat islet cell line. Proc. Natl. Acad. Sci. U.S.A. 1987, 84, 3434-3438.
15. Holz, G. G.; Kuhtreiber, W. M.; Habener, J. F., Pancreatic beta-cells are rendered glucosecompetent by the insulinotropic hormone glucagon-like peptide-1(7-37). Nature 1993, 361, 362-365.
16. Bulotta, A.; Hui, H.; Anastasi, E.; Bertolotto, C.; Boros, L. G.; Di Mario, U.; Perfetti, R., Cultured pancreatic ductal cells undergo cell cycle re-distribution and beta-cell-like differentiation in response to glucagon-like peptide-1. J. Mol. Endocrinol. 2002, 29, 347-360.
17. Egan, J. M.; Bulotta, A.; Hui, H.; Perfetti, R., GLP-1 receptor agonists are growth and differentiation factors for pancreatic islet beta cells. Diabetes/Metab. Res. Rev. 2003, 19, 115-123.
18. Stoffers, D. A.; Kieffer, T. J.; Hussain, M. A.; Drucker, D. J.; Bonner-Weir, S.; Habener, J. F.; Egan, J. M., Insulinotropic glucagon-like peptide 1 agonists stimulate expression of homeodomain protein IDX-1 and increase islet size in mouse pancreas, Diabetes 2000, 49, 741-748.
19. Unger, R. H., Role of glucagon in the pathogenesis of diabetes: the status of the controversy. Metabolism 1978, 27, 1691-1709.
20. Ørskov, C.; Holst, J. J.; Neilsen, O. V., Effect of truncated glucagon-like peptide-1 [proglucagon(78-107) amide] on endocrine secretion from pig pancreas, antrum, and nonantral stomach. Endocrinology 1988, 123, 2009-2013.
21. Wettergren, A.; Schjoldager, B.; Mortensen, P. E.; Myhre, J.; Christiansen, J.; Holst, J. J., Truncated GLP-1 (proglucagon 78-107-amide) inhibits gastric and pancreatic functions in man. Dig. Dis. Sci. 1993, 38, 665-673.
22. Flint, A.; Raben, A.; Astrup, A.; Holst, J. J., Glucagon-like peptide 1 promotes satiety and suppresses energy intake in humans. J. Clin. Invest. 1998, 101, 515-520.
23. Zander, M.; Madsbad, S.; Madsen, J. L.; Holst, J. J., Effect of 6-week course of glucagon-like peptide 1 on glycaemic control, insulin sensitivity, and beta-cell function in type 2 diabetes: a parallel-group study. Lancet 2002, 359, 824-830.
24. Knudsen, L. B., Glucagon-like peptide-1: the basis of a new class of treatment for type 2 diabetes. J. Med. Chem. 2004, 47, 4128-4134.
25. Toft-Nielsen, M. B.; Madsbad, S.; Holst, J. J., Determinants of the effectiveness of glucagon-like peptide-1 in type 2 diabetes. J. Clin. Endocrinol. Metab. 2001, 86, 3853-3860.
26. Vilsboll, T.; Krarup, T.; Madsbad, S.; Holst, J. J., No reactive hypoglycaemia in type 2 diabetic patients after subcutaneous administration of GLP-1 and intravenous glucose. Diabetic Med. 2001, 18, 144-149.
27. Eng, J.; Kleinman, W. A.; Singh, L.; Singh, G.; Raufman, J. P., Isolation and characterization of exendin-4, an exendin-3 analogue, from Heloderma suspectum venom. Further evidence for an exendin receptor on dispersed acini from guinea pig pancreas. J. Biol. Chem. 1992, 267, 7402-7405.
28. Göke, R.; Fehmann, H. C.; Linn, T.; Schmidt, H.; Krause, M.; Eng, J.; Göke, B., Exendin-4 is a high potency agonist and truncated exendin-(9-39)-amide an antagonist at the glucagon-like peptide 1-(7-36)-amide receptor of insulin-secreting beta-cells. J. Biol. Chem. 1993, 268, 19650-19655.
29. Young, A. A.; Gedulin, B. R.; Bhavsar, S.; Bodkin, N.; Jodka, C.; Hansen, B.; Denaro, M., Glucose-lowering and insulin-sensitizing actions of exendin-4. Diabetes 1999, 48, 1026-1034.
30. Edwards, C. M. B.; Stanley, S. A.; Davis, R.; Brynes, A. E.; Frost, G. S.; Seal, L. J.; Ghatei, M. A.; Bloom, S. R., Exendin-4 reduces fasting and postprandial glucose and decreases energy intake in healthy volunteers. Am. J. Physiol. Endocrinol. Metab. 2001, 281, E155-E161.
31. DeFronzo, R. A.; Ratner, R. E.; Han, J.; Kim, D. D.; Fineman, M. S.; Baron, A. D., Effects of exenatide (exendin-4) on glycemic control and weight over 30 weeks in metformin-treated patients with type 2 diabetes. Diabetes Care 2005, 28, 1092-1100.
32. Elbronds, B.; Jakobsen, G.; Larsen, S.; Agerso, H.; Jensen, L. B.; Rolan, P.; Sturis, J.; Hatorp, V.; Zdravkovic, 32. M., Pharmacokinetics, pharmacodynamics, safety, and tolerability of a single-dose of NN2211, a long-acting glucagon-like peptide 1 derivative, in healthy male subjects. Diabetes Care 2002, 25, 1398-1404.
33. Deacon, C. F.; Johnsen, A. H.; Holst, J. J., Degradation of glucagon-like peptide-1 by human plasma in vitro yields an N-terminally truncated peptide that is a major endogenous metabolite in vivo. J. Clin. Endocrinol. Metab. 1995, 80, 952-957.
34. Kieffer, T. J.; McIntosh, C. H. S.; Pederson, R. A., Degradation of GIP and truncated GLP-1 in vitro and in vivo by dipeptidyl peptidase IV. Endocrinology 1995, 136, 3585-3596.
35. Perry, T. A.; Greig, N. H., The glucagon-like peptides: a double-edged therapeutic sword? Trends Pharmacol. Sci. 2003, 24, 377-383.
36. Knudsen, L. B.; Pridal, L., GLP-1(9-36)amide is major metabolite of GLP-1(7-36)amide after in vivo administration to dogs, and it acts as an antagonist on the pancreatic receptor. Eur. J. Pharmacol. 1996, 318, 429-435.
37. Drucker, D. J.; Nauck, M. A., The incretin system: glucagon-like peptide-1 receptor agonists and dipeptidyl peptidase-4 inhibitors in type 2 diabetes. Lancet 2006, 368, 1696-1705.
38. Murphy, K. G.; Bloom, S. R., Nonpeptidic glucagon-like peptide 1 receptor agonists: A magic bullet for diabetes? Proc. Natl. Acad. Sci. U.S.A. 2007, 104, 689-690.
39. Pauletti, G. M.; Gangwar, S.; Siahaan, T. J.; Aubé, J.; Borchardt, R. T., Improvement of oral peptide bioavailability: Peptidomimetics and prodrug strategies. Adv. Drug Delivery Rev. 1997, 27, (235-256).
40. Mahato, R. I.; Narang, A. S.; Thoma, L.; Miller, D. D., Emerging trends in oral delivery of peptide and protein drugs. Critical Reviews in Therapeutic Drug Carrier Systems 2003, 20, 153-214.
41. Kolterman, O. G.; Buse, J. B.; Fineman, M. S.; Gaines, E.; Heintz, S.; Bicsak, T. A.; Taylor, K.; Kim, D.; Aisporna, M.; Wang, Y.; Baron, A. D., Synthetic exendin-4 (exenatide) significantly reduces postprandial and fasting plasma glucose in subjects with type 2 diabetes. J. Clin. Endocrinol. Metab. 2003, 88, 3082-3089.
42. Collins, J. L.; Dambek, P. J.; Goldstein, S. W.; Faraci, W. S., CP-99, 711: A non-peptide glucagon receptor antagonist. Bioorg. Med. Chem. Lett. 1992, 2, 915-918.
43. Madsen, P.; Knudsen, L. B.; Wiberg, F. C.; Carr, R. D., Discovery and structure-activity relationship of the first non-peptide competitive human glucagon receptor antagonists. J. Med. Chem. 1998, 41, 5150-5157.
44. Cascieri, M. A.; Koch, G. E.; Ber, E.; Sandowski, S. J.; Louizides, D.; de Laszlo, S. E.; Hacker, C.; Hagmann, W. K.; MacCoss, M.; Chicchi, G. G.; Vicario, P. P., Characterization of a novel, nonpeptidyl antagonist of the human glucagon receptor. J. Biol. Chem. 1999, 271, 8694-8697.
45. Chang, L. L.; Sidler, K. L.; Cascieri, M. A.; De Laszlo, S. E.; Koch, G.; Li, B.; MacCoss, M.; Mantlo, N.; O'Keefe, S.; Pang, M.; Rolando, A.; Hagmann, W. K., Substituted imidazoles as glucagon receptor antagonists. Bioorg. Med. Chem. Lett. 2001, 11, 2549-2553.
46. Ling, A.; Hong, Y.; Gonzalez, J.; Gregor, V.; Polinsky, A.; Kuki, A.; Shi, S.; Teston, K.; Murphy, D.; Porter, J.; Kiel, D.; Lakis, J.; Anderes, K.; May, J., Identification of alkylidene hydrazides as glucagon receptor antagonists. J. Med. Chem. 2001, 44, 3141-3149.
47. Tibaduiza, E. C.; Chen, C.; Beinborn, M., A small molecule ligand of the glucagon-like peptide 1 receptor targets its amino-terminal hormone binding domain. J. Biol. Chem. 2001, 276, 37787-37793.
48. Madsen, P.; Ling, A.; Plewe, M.; Sams, C. K.; Knudsen, L. B.; Sidelmann, U. G.; Ynddal, L.; Brand, C. L.; Andersen, B.; Murphy, D.; Teng, M.; Truesdale, L.; Kiel, D.; May, J.; Kuki, A.; Shi, S.; Johnson, M. D.; Teston, K. A.; Feng, J.; Lakis, J.; Anderes, K.; Gregor, V.; Lau, J., Optimization of alkylidene hydrazide based human glucagon receptor antagonists. Discovery of the highly potent and orally available 3-cyano-4-hydroxybenzoic acid [1-(2,3,5,6-tetramethylbenzyl)-1H-indol-4-ylmethylene]hydrazide. J. Med. Chem. 2002, 45, 5755-5775.
49. Hoare, S. R. J., Mechanisms of peptide and nonpeptide ligand binding to class B G-proteincoupled receptors. Drug Discovery Today 2005, 10, 417-427.
50. Knudsen, L. B.; Kiel, D.; Teng, M.; Behrens, C.; Bhumralkar, D.; Kodra, J. T.; Holst, J. J.; Jeppesen, C. B.; Johnson, M. D.; de Jong, J. C.; Jorgensen, A. S.; Kercher, T.; Kostrowicki, J.; Madsen, P.; Olesen, P. H.; Petersen, J. S.; Poulsen, F.; Sidelmann, U. G.; Sturis, J.; Truesdale, L.; May, J.; Lau, J., Small-molecule agonists for the glucagon-like peptide 1 receptor. Proc. Natl. Acad. Sci. U.S.A. 2007, 104, 937-942.
51. Chen, D.; Liao, J.; Li, N.; Zhou, C.; Liu, Q.; Wang, G.; Zhang, R.; Zhang, S.; Lin, L.; Chen, K.; Xie, X.; Nan, F.; Young, A. A.; Wang, M.-W., A nonpeptidic agonist of glucagon-like peptide 1 receptors with efficacy in diabetic db/db mice. Proc. Natl. Acad. Sci. U.S.A. 2007, 104, 943-948.
52. Marshall, G. R., A hierarchical approach to peptidomimetic design. Tetrahedron 1993, 49, 3547-3558.
53. Ahn, J.-M.; Boyle, N. A.; MacDonald, M. T.; Janda, K. D., Peptidomimetics and peptide backbone modifications. Mini-Reviews in Medicinal Chemistry 2002, 2, 463-473.
54. Olson, G. L.; Bolin, D. R.; Bonner, M. P.; Bös, M.; Cook, C. M.; Fry, D. C.; Graves, B. J.; Hatada, M.; Hill, D. E.; Kahn, M.; Madison, V. S.; Rusiecki, V. K.; Sarabu, R.; Sepinwall, J.; Vincent, G. P.; Voss, M. E., Concepts and progress in the development of peptide mimetics. J. Med. Chem. 1993, 36, 3039-3049.
55. Gante, J., Peptidomimetics—tailored enzyme inhibitors. Angew. Chem. Int. Ed. 1994, 33, 1699-1720.
56. Hirschmann, R.; Nicolaou, K. C.; Pietranico, S.; Salvino, J.; Leahy, E. M.; Sprengeler, P. A.; Furst, G.; Smith, A. B.; Strader, C. D.; Cascieri, M. A.; Candelore, M. R.; Donaldson, C.; Vale, W.; Maechler, L., Nonpeptidal peptidomimetics with β-D-glucose scaffolding. A partial somatostatin agonist bearing a close structural relationship to a potent, selective substance P antagonist. J. Am. Chem. Soc. 1992, 114, 9217-9218.
57. Hirschmann, R.; Nicolaou, K. C.; Pietranico, S.; Leahy, E. M.; Salvino, J.; Arison, B.; Cichy, M. A.; Spoors, P. G.; Shakespeare, W. C.; Sprengeler, P. A.; Hamley, P.; Smith, A. B.; Reisine, T.; Raynor, K.; Maechler, L.; Donaldson, C.; Vale, W.; Freidinger, R. M.; Cascieri, M. R.; Strader, C. D., De novo design and synthesis of somatostatin nonpeptide peptidomimetics utilizing β-D-glucose as a novel scaffolding. J. Am. Chem. Soc. 1993, 115, 12550-12568.
58. Hruby, V. J., Design in topographical space of peptide and peptidomimetic ligands that affect behavior a chemist's glimpse at the mind-body problem. Acc. Chem. Res. 2001, 34, 389-397.
59. Peczuh, M. W.; Hamilton, A. D., Peptide and protein recognition by designed molecules. Chem. Rev. 2000, 100, 2479-2494.
60. Segre, G. V.; Goldring, S. R., Receptors for secretin, calcitonin, parathyroid hormone (PTH)/PTHrelated peptide, vasoactive intestinal peptide, glucagonlike peptide 1, growth hormone-releasing hormone, and glucagon belong to a newly discovered G-protein-linked receptor family. Trends in Endocrinology and Metabolism 1993, 4, 309-314.

61. Konig, W., Peptides and protein hormones. Pharmaceuticals 2000, 3, 1339-1492.
62. Ahn, J.-M.; Medeiros, M.; Trivedi, D.; Hruby, V. J., Development of potent truncated glucagon antagonists. J. Med. Chem. 2001, 44, 1372-1379.
63. Runge, S.; Wulff, B. S.; Madsen, K.; Bräuner-Osborne, H.; Knudsen, L. B., Different domains of the glucagon and glucagon-like peptide-1 receptors provide the critical determinants of ligand selectivity. Br. J. Pharmacol. 2003, 138, 787-794.
64. Ahn, J.-M.; Gitu, P. M.; Medeiros, M.; Swift, J.; Trivedi, D.; Hruby, V. J., A new approach to search for the bioactive conformation of glucagon: positional cyclization scanning. J. Med. Chem. 2001, 44, 3109-3116.
65. Thornton, K.; Gorenstein, D. G., Structure of glucagon-like peptide(7-36) amide in a dodecylphosphocholine micelle as determined by 2D NMR. Biochemistry 1994, 33, 3532-3539.
66. Neidigh, J. W.; Fesinmeyer, R. M.; Prickett, K. S.; Andersen, N. H., Exendin-4 and glucagon-likepeptide-1: NMR structural comparisons in the solution and micelle-associated states. Biochemistry 2001, 40, 13188-13200.
67. Rizo, J.; Gierasch, L. M., Constrained peptides: models of bioactive peptides and protein substructures. Annu. Rev. Biochem. 1992, 61, 387-418.
68. Widmer, H.; Widmer, A.; Braun, W., Extensive distance geometry calculations with different NOE calibrations: new criteria for structure selection applied to sandostatin and BPTI. J. Biomol. NMR 1993, 3, 307-324.
69. Marqusee, S.; Baldwin, R. L., Helix stabilization by Glu-. . . Lys+ salt bridges in short peptides of de novo design. Proc. Natl. Acad. Sci. U.S.A. 1987, 84, 8898-8902.
70. Ösapay, G.; Taylor, J. W., Multicyclic polypeptide model compounds. 1. Synthesis of a tricyclic amphiphilic α-helical peptide using an oxime resin, segment-condensation approach. J. Am. Chem. Soc. 1990, 112, 6046-6051.
71. Bogan, A. A.; Thorn, K. S., Anatomy of hot spots in protein interfaces. J. Mol. Biol. 1998, 280, 1-9.
72. Burgess, K., Solid-phase syntheses of β-turn analogues to mimic or disrupt protein-protein interactions. Acc. Chem. Res. 2001, 34, 826-835.
73. Souers, A. J.; Ellman, J. A., β-Turn mimetic library synthesis: scaffolds and applications. Tetrahedron 2001, 57, 7431-7448.
74. Figuera, N. D. L.; Martin-Martinez, M.; Herranz, R.; Garcia-López, M. T.; Latorre, M.; Cenarruzabeitia, E.; R10, J. D.; Gonzalez-Muñiz, R., Highly constrained dipeptoid analogues containing a type II' b-turn mimic as novel and selective CCK-A receptor ligands. Bioorg. Med. Chem. Lett. 1999, 9, 43-48.
75. Horwell, D. C.; Howson, W.; Ratcliffe, G. S.; Willems, H. M., The design of dipeptide helical mimetics: the synthesis, tachykinin receptor affinity and conformational analysis of 1,1,6-trisubstituted indanes. Bioorg. Med. Chem. 1996, 4, 33-42.
76. Jacoby, E., Biphenyls as potential mimetics of protein α-helix. Bioorg. Med. Chem. Lett. 2002, 12, 891-893.
77. Omer, B. P.; Ernst, J. T.; Hamilton, A. D., Toward proteomimetics: Terphenyl derivatives as structural and functional mimics of extended regions of an α-helix. J. Am. Chem. Soc. 2001, 123, 5382-5383.
78. Ernst, J. T.; Becerril, J.; Park, H. S.; Yin, H.; Hamilton, A. D., Design and application of an α-helixmimetic scaffold based on an oligoamide-foldamer strategy: antagonism of the Bak BH3/Bcl-xL complex. Angew. Chem. Int. Ed. 2003, 42, 535-539.
79. Oguri, H.; Oomura, A.; Tanabe, S.; Hirama, M., Design and synthesis of a trans-fused polycyclic ether skeleton as an α-helix mimetic scaffold. Tetrahedron Lett. 2005, 46, 2179-2183.
80. Mohamadi, F.; Richards, N. G. J.; Guida, W. C.; Liskamp, R.; Lipton, M.; Caufield, C.; Chang, G.; Hendrickson, T.; Still, W. C., MacroModel—An integrated software system for modeling organic and bioorganic molecules using molecular mechanics. J. Comput. Chem. 1990, 11, 440-467.
81. Allinger, N. L.; Yuh, Y. H.; Lii, J.-H., Molecular mechanics. The MM3 force field for hydrocarbones. 1. J. Am. Chem. Soc. 1989, 111, 8551-8565.
82. Ahn, J.-M.; Han, S.-Y., Facile synthesis of benzamides to mimic an α-helix. Tetrahedron Lett. Accepted.
83. Rickard, D. J.; Wang, F.-L.; Rodríguez-Rojas, A.-M.; Wu, Z.; Trice, W. J.; Hoffman, S. J.; Votta, B.; Stroup, G. B.; Kumar, S.; Nuttall, M. E., Intermittent treatment with parathyroid hormone (PTH) as well as a non-peptide small molecule agonist of the PTH1 receptor inhibits adipocyte differentiation in human bone marrow stromal cells. Bone 2006, 39, 1361-1372.
84. Chapuis, H.; Strazewski, P., Shorter puromycin analog synthesis by means of an efficient Staudinger-Vilarrasa coupling. Tetrahedron 2006, 62, 12108-12115.
85. Adelhorst, K.; Hedegaard, B. B.; Knudsen, L. B.; Kirk, O., Structure-activity studies of glucagonlike peptide-1. J. Biol. Chem. 1994, 269, 6275-6278.

What is claimed is:

1. A compound of the formula:

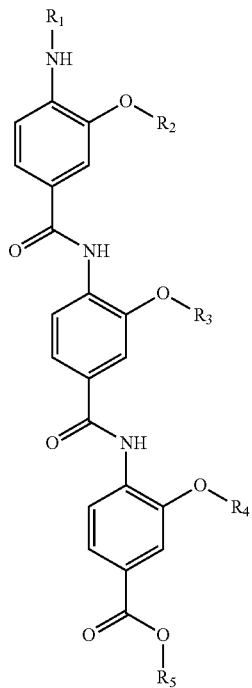

wherein $R_1$ is an acetyl group, R2 is a substituted or unsubstituted lower alkyl group or a substituted or unsubstituted benzyl group, $R_3$ is substituted or unsubstituted lower alkyl group or a substituted or unsubstituted benzyl group, $R_4$ is a substituted or unsubstituted alkyl group or a substituted or unsubstituted benzyl group and $R_5$ is H, a substituted or unsubsitutued alkyl group, a substituted or unsubstituted benzyl group, or $CH_2CH{=}CH_2$.

2. The compound of claim 1, wherein, $R_2$ is n-butyl, sec-butyl or iso-butyl.

3. The compound of claim 1, wherein $R_3$ is n-butyl, sec-butyl or iso-butyl.

4. The compound of claim 1, wherein $R_4$ is n-butyl, sec-butyl or iso-butyl.

5. The compound of claim 1, wherein $R_4$ is $CH_2C_6H_5$.

6. The compound of claim 1, wherein $R_5$ is H.

7. The compound of claim 1, wherein $R_5$ is $CH_2CH{=}CH_2$.

8. The compound of claim 1, wherein $R_5$ is a substituted or substituted henzyl group.

9. The compound of claim 1, wherein $R_5$ is a substituted or unsubstituted lower alkyl group.

10. A composition comprising the compound of claim 1, dispersed in a carrier.

* * * * *

UNITED STATES PATENT AND TRADEMARK OFFICE
CERTIFICATE OF CORRECTION

PATENT NO. : 8,618,324 B2
APPLICATION NO. : 12/048197
DATED : December 31, 2013
INVENTOR(S) : Ahn Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 573 days.

Signed and Sealed this
Twenty-first Day of April, 2015

Michelle K. Lee
*Director of the United States Patent and Trademark Office*